(12) United States Patent
Bennett et al.

(10) Patent No.: US 10,654,916 B2
(45) Date of Patent: May 19, 2020

(54) COMPOSITIONS AND METHODS FOR THE TREATMENT OF NEUROMYELITIS OPTICA

(75) Inventors: Jeffrey L. Bennett, Aurora, CO (US);
Gregory P. Owens, Aurora, CO (US);
Alan S. Verkman, San Francisco, CA (US)

(73) Assignees: THE REGENTS OF THE UNIVERSITY OF CALIFORNIA, A CALIFORNIA CORPORATION, Oakland, CA (US); THE REGENTS OF THE UNIVERSITY OF COLORADO A BODY CORPORATE, Denver, CO (US)

( * ) Notice: Subject to any disclaimer, the term of this patent is extended or adjusted under 35 U.S.C. 154(b) by 0 days.

(21) Appl. No.: 14/113,061

(22) PCT Filed: Apr. 23, 2012

(86) PCT No.: PCT/US2012/034662
§ 371 (c)(1),
(2), (4) Date: Feb. 3, 2014

(87) PCT Pub. No.: WO2012/145746
PCT Pub. Date: Oct. 26, 2012

(65) Prior Publication Data
US 2014/0170140 A1    Jun. 19, 2014

Related U.S. Application Data

(60) Provisional application No. 61/477,955, filed on Apr. 21, 2011.

(51) Int. Cl.
*C07K 16/18* (2006.01)
*C07K 16/28* (2006.01)
(Continued)

(52) U.S. Cl.
CPC .......... *C07K 16/18* (2013.01); *A61K 39/3955* (2013.01); *A61K 45/06* (2013.01);
(Continued)

(58) Field of Classification Search
None
See application file for complete search history.

(56) References Cited

U.S. PATENT DOCUMENTS

| 4,196,265 A | 1/1980 | Koprowski et al. |
| 4,554,101 A | 11/1985 | Hopp |
| (Continued) | | |

FOREIGN PATENT DOCUMENTS

| EP | 0125023 A1 | 11/1984 |
| EP | 0171496 A2 | 2/1986 |
| (Continued) | | |

OTHER PUBLICATIONS

Bennett et al., Intrathecal Pathogenic Anti-Aquaporin-4 Antibodies in Early Neuromyelitis Optica. Annals of Neurology vol. 66 No. 5 Nov. 2009, 617-629.*

(Continued)

*Primary Examiner* — Aurora M Fontainhas
(74) *Attorney, Agent, or Firm* — Mintz Levin Cohn Ferris Glovsky and Popeo PC; Terri Shieh-Newton; David Dang

(57) ABSTRACT

The present invention is directed to antibodies binding to aquaporin 4 (AQP4) and methods of using such antibodies to treat neuromyelitis optica (NMO) either as a monotherapy or in combination with standard NMO therapies such as immunosuppressives or plasmaphersis.

24 Claims, 18 Drawing Sheets
Specification includes a Sequence Listing.

(51) Int. Cl.
*A61K 39/395* (2006.01)
*A61K 45/06* (2006.01)

(52) U.S. Cl.
CPC .......... *C07K 16/28* (2013.01); *C07K 2317/21* (2013.01); *C07K 2317/71* (2013.01); *C07K 2317/732* (2013.01); *C07K 2317/734* (2013.01); *C07K 2317/76* (2013.01); *C07K 2317/92* (2013.01)

(56) References Cited

U.S. PATENT DOCUMENTS

| | | | |
|---|---|---|---|
| 4,680,338 | A | 7/1987 | Sundoro |
| 4,816,567 | A | 3/1989 | Cabilly et al. |
| 4,867,973 | A | 11/1989 | Goers et al. |
| 5,196,066 | A | 3/1993 | Kusuda et al. |
| 5,565,332 | A | 10/1996 | Hoogenboom et al. |
| 5,624,821 | A | 4/1997 | Winter et al. |
| 5,648,260 | A | 7/1997 | Winter et al. |
| 5,834,597 | A | 11/1998 | Tso et al. |
| 6,194,551 | B1 | 2/2001 | Idusogie et al. |
| 6,528,624 | B1 | 3/2003 | Idusogie et al. |
| 6,538,124 | B1 | 3/2003 | Idusogie et al. |
| 6,569,431 | B2 | 5/2003 | von Büdingen et al. |
| 6,737,056 | B1 | 5/2004 | Presta |
| 7,101,679 | B2 | 9/2006 | Lennon et al. |
| 7,122,637 | B2 | 10/2006 | Presta |
| 7,183,387 | B1 | 2/2007 | Presta |
| 7,297,775 | B2 | 11/2007 | Idusogie et al. |
| 7,332,581 | B2 | 2/2008 | Presta |
| 7,335,742 | B2 | 2/2008 | Presta |
| 7,364,731 | B2 | 4/2008 | Idusogie et al. |
| 7,371,826 | B2 | 5/2008 | Presta |
| 7,416,727 | B2 | 8/2008 | Presta |
| 7,608,260 | B2 | 10/2009 | Schenerman et al. |
| 7,632,497 | B2 | 12/2009 | Stavenhagen |
| 7,659,312 | B2 | 2/2010 | Nakada et al. |
| 7,662,925 | B2 | 2/2010 | Lazar et al. |
| 7,670,600 | B2 | 3/2010 | Dall'Acqua et al. |
| 7,700,099 | B2 | 4/2010 | Strohl |
| 7,704,497 | B2 | 4/2010 | Dall'Acqua et al. |
| 7,750,127 | B2 | 7/2010 | Gegg et al. |
| 7,863,419 | B2 | 1/2011 | Taylor et al. |
| 8,012,476 | B2 | 9/2011 | Dall'Acqua et al. |
| 8,093,357 | B2 | 1/2012 | Lazar et al. |
| 8,106,161 | B2 | 1/2012 | Ledbetter et al. |
| 8,192,737 | B2 | 6/2012 | Stavenhagen et al. |
| 8,197,810 | B2 | 6/2012 | Ledbetter et al. |
| 8,216,574 | B2 | 7/2012 | Stavenhagen et al. |
| 8,318,917 | B2 | 11/2012 | Taylor et al. |
| 8,323,962 | B2 | 12/2012 | Dall'Acqua et al. |
| 8,409,568 | B2 | 4/2013 | Gao et al. |
| 8,445,645 | B2 | 5/2013 | Stavenhagen et al. |
| 8,475,792 | B2 | 7/2013 | Dall'Acqua et al. |
| 2002/0072588 | A1* | 6/2002 | Budingen et al. ......... 530/387.2 |
| 2003/0166868 | A1 | 9/2003 | Presta et al. |
| 2003/0211100 | A1 | 11/2003 | Bedian et al. |
| 2004/0132101 | A1 | 7/2004 | Lazar et al. |
| 2004/0265321 | A1 | 12/2004 | Johnson et al. |
| 2005/0049402 | A1 | 3/2005 | Babcook et al. |
| 2005/0196754 | A1 | 9/2005 | Drmanac et al. |
| 2005/0215768 | A1 | 9/2005 | Armour et al. |
| 2005/0249723 | A1 | 11/2005 | Lazar |
| 2006/0039904 | A1 | 2/2006 | Wu et al. |
| 2006/0067930 | A1 | 3/2006 | Adams et al. |
| 2006/0134105 | A1 | 6/2006 | Lazar et al. |
| 2006/0194290 | A1 | 8/2006 | Presta |
| 2006/0235208 | A1 | 10/2006 | Lazar et al. |
| 2006/0275283 | A1 | 12/2006 | van Vlijmen et al. |
| 2007/0009523 | A1 | 1/2007 | Presta |
| 2007/0148170 | A1 | 6/2007 | Desjarlais et al. |
| 2007/0237765 | A1 | 10/2007 | Lazar et al. |
| 2007/0237766 | A1 | 10/2007 | Lazar et al. |
| 2007/0248602 | A1 | 10/2007 | Lazar et al. |
| 2007/0248603 | A1 | 10/2007 | Lazar et al. |
| 2007/0275460 | A1 | 11/2007 | Desjarlais et al. |
| 2008/0051563 | A1 | 2/2008 | Lazar et al. |
| 2008/0112961 | A1 | 5/2008 | Stavenhagen et al. |
| 2008/0138349 | A1 | 6/2008 | Stavenhagen et al. |
| 2008/0154025 | A1 | 6/2008 | Lazar et al. |
| 2008/0161541 | A1 | 7/2008 | Lazar et al. |
| 2008/0181890 | A1 | 7/2008 | Lazar et al. |
| 2008/0206867 | A1 | 8/2008 | Desjarlais et al. |
| 2008/0221120 | A1 | 9/2008 | Verkman |
| 2008/0242845 | A1 | 10/2008 | Lazar et al. |
| 2008/0248028 | A1 | 10/2008 | Lazar et al. |
| 2008/0292621 | A1 | 11/2008 | Lazar et al. |
| 2008/0317758 | A9 | 12/2008 | Presta |
| 2009/0042291 | A1 | 2/2009 | Chu et al. |
| 2009/0081208 | A1 | 3/2009 | Lazar et al. |
| 2009/0136513 | A1 | 5/2009 | Pereira et al. |
| 2009/0142340 | A1 | 6/2009 | Lazar et al. |
| 2009/0142806 | A1 | 6/2009 | Carreno et al. |
| 2009/0175851 | A1 | 7/2009 | Klein et al. |
| 2009/0214526 | A1 | 8/2009 | Lazar et al. |
| 2009/0215991 | A1 | 8/2009 | Lazar et al. |
| 2009/0311253 | A1 | 12/2009 | Ghayur et al. |
| 2010/0092478 | A1 | 4/2010 | Lennon et al. |
| 2010/0112080 | A1 | 5/2010 | Hogarth et al. |
| 2010/0184959 | A1 | 7/2010 | Guler-Gane et al. |
| 2010/0203046 | A1 | 8/2010 | van Vlijmen et al. |
| 2010/0226860 | A1 | 9/2010 | Lennon et al. |
| 2010/0254985 | A1 | 10/2010 | Allan et al. |
| 2010/0266505 | A1* | 10/2010 | Black et al. .................. 424/9.3 |
| 2010/0330076 | A1 | 12/2010 | Georgiou et al. |
| 2011/0064727 | A9 | 3/2011 | Lazar et al. |
| 2011/0077383 | A1 | 3/2011 | Dall'Acqua et al. |
| 2011/0086026 | A1 | 4/2011 | Endl et al. |
| 2011/0196662 | A1 | 8/2011 | Kjellbom et al. |
| 2011/0212087 | A1 | 9/2011 | Strohl et al. |
| 2011/0293632 | A1 | 12/2011 | Presta |
| 2012/0039907 | A1 | 2/2012 | Armour et al. |
| 2012/0065379 | A1 | 3/2012 | Igawa et al. |
| 2012/0071634 | A1 | 3/2012 | Igawa et al. |
| 2012/0087927 | A1 | 4/2012 | Matsushima et al. |
| 2012/0100140 | A1 | 4/2012 | Reyes et al. |
| 2012/0219969 | A1 | 8/2012 | Lennon et al. |
| 2012/0251531 | A1 | 10/2012 | Baehner et al. |
| 2013/0053318 | A1 | 2/2013 | Laura et al. |
| 2013/0058919 | A1 | 3/2013 | Lazar et al. |
| 2013/0089539 | A1 | 4/2013 | Rennert et al. |
| 2013/0089541 | A1 | 4/2013 | D'Angelo et al. |
| 2013/0101581 | A1 | 4/2013 | Kuramochi et al. |

FOREIGN PATENT DOCUMENTS

| | | |
|---|---|---|
| EP | 173494 A2 | 3/1986 |
| EP | 184187 A2 | 6/1986 |
| EP | 1700120 B1 | 4/2009 |
| WO | 86/01533 A1 | 3/1986 |
| WO | 87/02671 A1 | 5/1987 |
| WO | 2005/051178 A2 | 6/2005 |
| WO | WO-2010/046716 A1 | 4/2010 |
| WO | 2012/145746 A1 | 10/2012 |
| WO | 2013/177116 A1 | 11/2013 |

OTHER PUBLICATIONS

Misu et al., Intractable hiccup and nausea with periaqueductal lesions in neuromyelitis optica. Neurology 2005;65:1479-1482.*
NINDS webpage dowloaded on Sep. 17, 2014 http://www.ninds.nih.gov/disorders/neuromyelitis_optica/neuromyelitis_optica.htm.*
Chen "Enhancement and destruction of antibody function U by somatic mutation: unequal occurrence is controlled by V gene combinatorial associations" The EMBO Journal vol. 14 No. 1 2 pp. 2784-2794 (Year: 1995) (Year: 1995).*
Kussie "A Single Engineered Amino Acid Substitution Changes Antibody Fine Specificity" J immunol 152(1): 146-52 (Year: 1994) (Year: 1994).*
Edwards et al., The remarkable flexibility of the human antibody repertoire; isolation of over one thousand different antibodies to a single protein, BLyS.J Mol Biol. Nov. 14, 2003;334(1): 103-18. (Year: 2003).*

(56) References Cited

OTHER PUBLICATIONS

Paul, Fundamental Immunology, (textbook), 1993, pp. 292-295 (Year: 1993).*
Rudikoff et al. (Proc Natl Acad Sci USA, 1982; 79(6):1979-1983 (Year: 1982).*
Morrison, SL, "Transfectomas provide novel chimeric antibodies," Science 229(4719):1202-1207 (1985).
Neely et al., "Heterotetrameric composition of aquaporin-4 water channels," Biochemistry 38(34):11156-11163 (1999).
Nicchia et al., "Aquaporin-4 orthogonal arrays of particles are the target for neuromyelitis optica autoantibodies," Glia 57(13):1363-1373 (2009).
Nieri et al., "Antibodies for therapeutic uses and the evolution of biotechniques," Curr. Med. Chem. 16(6):753-779 (2009).
O'Shannessy et al., "Labeling of the oligosaccharide moieties of immunoglobulins," J. Immunol. Methods 99(2):153-161 (1987).
Padmawar et al., "K+ waves in brain cortex visualized using a long-wavelength K+-sensing fluorescent indicator," Nat. Methods 2(11):825-827 (2005).
Papadopoulos and Verkman, "Aquaporin 4 and neuromyelitis optica," Lancet Neurol. 11(6):535-544 (2012).
Papadopoulos et al., "Aquaporin-4 facilitates reabsorption of excess fluid in vasogenic brain edema," FASEB J. 18(11):1291-1293 (2004) (Epub Jun. 18, 2004).
Phuan et al., "A Small-molecule Screen Yields Idiotype-specific Blockers of Neuromyelitis Optica Immunoglobulin G Binding to Aquaporin-4," J. Biol. Chem. 287:36837-36844 (2012).
Ponten and MacIntyre, "Long term culture of normal and neoplastic human glia," Acta Pathol. Microbiol. Scand. 74(4):465-486 (1968).
Posner et al., "The construction and use of a human-mouse myeloma analogue suitable for the routine production of hybridomas secreting human monoclonal antibodies," Hybridoma 16(6):611-625 (1987).
Ratelade et al., "Evidence against cellular internalization in vivo of NMO-IgG, aquaporin-4, and excitatory amino acid transporter 2 in neuromyelitis optica," J. Biol. Chem. 286(52):45156-45164 (2011) (Epub Nov. 8, 2011).
Saadoun et al., "Greatly improved neurological outcome after spinal cord compression injury in AQP4-deficient mice," Brain 131(Pt 4):1087-1098 (2008) (Epub Feb. 11, 2008).
Saadoun et al., "Intra-cerebral injection of neuromyelitis optica immunoglobulin G and human complement produces neuromyelitis optica lesions in mice," Brain 133(Pt 2):349-361 (2010) (Epub Jan. 4, 2010).
Saadoun et al., "Involvement of aquaporin-4 in astroglial cell migration and glial scar formation," J. Cell Sci. 118(Pt 24):5691-5698 (2005) (Epub Nov. 22, 2005).
Shaw et al., "Mouse/human chimeric antibodies to a tumor-associated antigen: biologic activity of the four human IgG subclasses," J. Natl. Cancer Inst. 80(19):1553-1559 (1988).
Sosnick et al., "Distances between the antigen-binding sites of three murine antibody subclasses measured using neutron and X-ray scattering," Biochemistry 31(6):1779-1786 (1992).
Sun et al., "Interactions between glucocorticoid receptor-bearing chromatin and antireceptor antibody preparations," J. Steroid Biochem. 26(1):83-92 (1987).
Tajima et al., "Aquaporin-4 (AQP4) associations and array dynamics probed by photobleaching and single-molecule analysis of green fluorescent protein-AQP4 chimeras," J. Biol. Chem. 285(11):8163-8170 (2010) (Epub Jan. 13, 2010).
Takahashi et al., "Anti-aquaporin-4 antibody is involved in the pathogenesis of NMO: A study on antibody titre," Brain 130:1235-1243 (2007).
Tang et al., "Selection of linkers for a catalytic single-chain antibody using phage display technology," J. Biol. Chem. 271(26):15682-15686 (1996).
Tradtrantip et al., "Anti—Aquaporin-4 Monoclonal Antibody Blocker Therapy for Neuromyelitis Optica," Ann. Neurol. 71:314-322 (2012).
Tradtrantip et al., "Enzymatic Deglycosylation Converts Pathogenic Neuromyelitis Optica Anti—Aquaporin-4 Immunoglobulin G into Therapeutic Antibody," Ann. Neurol. 73:77-85 (2013).
Tradtrantip et al., "Small-molecule inhibitors of NMO-IgG binding to aquaporin-4 reduce astrocyte cytotoxicity in neuromyelitis optica," FASEB J. 26:2197-2208 (2012).
Verhoeyen et al., "Reshaping human antibodies: grafting an antilysozyme activity," Science 239(4847):1534-1536 (1988).
Verkman, A.S., "Mammalian aquaporins: diverse physiological roles and potential clinical significance," Expert Rev. Mol. Med. 10:e13 (2008).
Weinshenker, "Neuromyelitis Optica is Distinct From Multiple Sclerosis," Arch. Neurol. 64:899-901 (2007).
Wingerchuk et al., "Revised diagnostic criteria for neuromyelitis optica," Neurology 66(10):1485-1489 (2006).
Wingerchuk et al., "The spectrum of neuromyelitis optica," Lancet Neurol. 6:805-815 (2007).
Wolburg, "Orthogonal arrays of intramembranous particles: a review with special reference to astrocytes," J. Hirnforsch. 36(2):239-258 (1995).
Wood et al., "The detection of IgG anti-hepatocyte antibodies by ELISA in sera of patients with chronic active hepatitis: correlation with disease activity," J. Clin. Lab. Immunol. 17(4):167-171 (1985).
Yang et al., "cDNA cloning, gene organization, and chromosomal localization of a human mercurial insensitive water channel. Evidence for distinct transcriptional units," J. Biol. Chem. 270(39):22907-22913 (1995).
Yu et al., "Identification of peptide targets in neuromyelitis optica," J. Neuroimmunol. 236(1-2):65-71 (2011).
Auguste et al., "Greatly impaired migration of implanted aquaporin-4-deficient astroglial cells in mouse brain toward site of injury," FASEB J. 21(1)108-116 (2007).
Baudino et al., "Impact of a three amino acid deletion in the CH2 domain of murine IgG1 on Fc-associated effector functions," J. Immunol. 181(6):4107-4112 (2008).
Beidler et al., "Cloning and high level expression of a chimeric antibody with specificity for human carcinoembryonic antigen," J. Immunol. 141(11):4053-4060 (1988).
Binder et al., "Increased seizure duration and slowed potassium kinetics in mice lacking aquaporin-4 water channels," Glia 53(6):631-636 (2006).
Binder et al., "Increased seizure duration in mice lacking aquaporin-4 water channels," Acta. Neurochir. Suppl. 96:389-392 (2006).
Bradl et al., "Neuromyelitis optica: pathogenicity of patient immunoglobulin in vivo," Ann. Neurol. 66(5):630-643 (2009).
Canfield and Morrison, "The Binding Affinity of Human IgG for its High Affinity Fc Receptor is Determined by Multiple Amino Acids in the CH2 Domain and is Modulated by the Hinge Region," J. Exp. Med. 173:1483-1491 (1991).
Capaldi et al., "Changes in order of migration of polypeptides in complex III and cytochrome C oxidase under different conditions of SDS polyacrylamide gel electrophoresis," Biochem. Biophys. Res. Commun. 74(2):425-433 (1977).
Collongues and De Seze, "Current and future treatment approaches for neuromyelitis optica," Ther. Adv. Neurol. Disord. 4(2):111-121 (2011).
Crane and Verkman, "Determinants of aquaporin-4 assembly in orthogonal arrays revealed by live-cell single-molecule fluorescence imaging," J. Cell. Sci. 122(Pt 6):813-821 (2009).
Crane et al., "Aquaporin-4 dynamics in orthogonal arrays in live cells visualized by quantum dot single particle tracking," Mol. Biol. Cell. 19(8):3369-3378 (2008).
Crane et al., "Binding affinity and specificity of neuromyelitis optica autoantibodies to aquaporin-4 M1/M23 isoforms and orthogonal arrays," J. Biol. Chem. 286(18):16516-16524 (2011) ( Epub Mar. 21, 2011).
Crane et al., "Live cell analysis of aquaporin-4 m1/m23 interactions and regulated orthogonal array assembly in glial cells," J. Biol. Chem. 284(51):35850-35860 (2009).
Duncan and Winter, "The binding site for C1q on IgG," Nature 332(6166):738-740 (1988).
Furman et al., "Aquaporin-4 square array assembly: opposing actions of M1 and M23 isoforms," Proc. Natl. Acad. Sci. U.S.A. 100(23):13609-13614 (2003).

(56) References Cited

OTHER PUBLICATIONS

Gefter et al., "A simple method for polyethylene glycol-promoted hybridization of mouse myeloma cells," Somatic Cell Genet. 3(2):231-236 (1977).
GenBank Accession No. EU599327.1; GI: 194173392 (Jul. 15, 2009), downloaded Jul. 18, 2012.
Hagenmeyer et al., "Single-chain antibodies as diagnostic tools and therapeutic agents," Thromb. Haemost. 101(6):1012-1019 (2009).
Harris et al., "Crystallographic structure of an intact IgG1 monoclonal antibody," J. Mol. Biol. 275(5):861-872 (1998).
Hasegawa et al., "Molecular cloning of a mercurial-insensitive water channel expressed in selected water-transporting tissues," J. Biol. Chem. 269(8):5497-5500 (1994).
Hezareh et al., "Effector function activities of a panel of mutants of a broadly neutralizing antibody against human immunodeficiency virus type 1," J. Virol. 75(24):12161-12168 (2001).
Hinson et al., "Aquaporin-4-binding autoantibodies in patients with neuromyelitis optica impair glutamate transport by down-regulating EAAT2," J. Exp. Med. 205(11):2473-2481 (2008).
Hinson et al., "Pathogenic potential of IgG binding to water channel extracellular domain in neuromyelitis optica," Neurology 69(24):2221-2231 (2007).
Hinson et al., "Prediction of neuromyelitis optica attack severity by quantitation of complement-mediated injury to aquaporin-4-expressing cells," Arch. Neurol. 66(9):1164-1167 (2009).
Ho et al., "Crystal structure of human aquaporin 4 at 1.8 A and its mechanism of conductance," Proc. Natl. Acad. Sci. U.S.A. 106(18):7437-7442 (2009).
Idusogie et al., "Engineered antibodies with increased activity to recruit complement," J. Immunol. 66(4):2571-2575 (2001).
Igawa et al., "Engineering the variable region of therapeutic IgG antibodies," MAbs. May-Jun. 2011;3(3):243-252 (2011), (Epub May 1, 2011).
Jarius et al., "Antibody to aquaporin-4 in the long-term course of neuromyelitis optica," Brain 131(Pt 11):3072-3080 (2008).
Jarius et al., "Immunoglobulin M antibodies to aquaporin-4 in neuromyelitis optica and related disorders," Clin. Chem. Lab. Med. 48(5):659-663 (2010).
Jefferis et al., "IgG-Fc-mediated effector functions: molecular definition of interaction sites for effector ligands and the role of glycosylation," Immunological Reviews 163:59-76 (1998).
Jones et al., "Replacing the complementarity-determining regions in a human antibody with those from a mouse," Nature 321(6069):522-525 (1986).
Jung et al., "Molecular characterization of an aquaporin cDNA from brain: candidate osmoreceptor and regulator of water balance," Proc. Natl. Acad. Sci. U.S.A. 91(26):13052-13056 (1994).
Kaneko and Niwa, "Optimizing therapeutic antibody function: progress with Fc domain engineering," BioDrugs 25(1):1-11 (2011).
Kinoshita et al., "Anti-aquaporin-4 antibody induces astrocytic cytotoxicity in the absence of CNS antigen-specific T cells," Biochem. Biophys. Res. Commun. 394(1):205-210 (2010).
Köhler and Milstein, "Continuous cultures of fused cells secreting antibody of predefined specificity," Nature 256 (5517):495-497 (1975).
Köhler and Milstein, "Derivation of specific antibody-producing tissue culture and tumor lines by cell fusion," Eur. J. Immunol. 6(7):511-519 (1976).
Kontermann, RE, "Strategies to extend plasma half-lives of recombinant antibodies," BioDrugs 23(2):93-109 (2009).
Kyte and Doolittle, "A simple method for displaying the hydropathic character of a protein," J. Mol. Biol. 157(1):105-132 (1982).
Landis and Reese, "Arrays of particles in freeze-fractured astrocytic membranes," J. Cell. Biol. 60(1):316-320 (1974).
Lennon et al., "IgG marker of optic-spinal multiple sclerosis binds to the aquaporin-4 water channel," J. Exp. Med. 202(4):473-477 (2005).
Li and Verkman, "Impaired hearing in mice lacking aquaporin-4 water channels," J. Biol. Chem. 276 (33):31233-31237 (2001).
Li et al., "Proinflammatory role of aquaporin-4 in autoimmune neuroinflammation," FASEB J. 25(5):1556-1566 (2011) (Epub Jan. 21, 2011).
Lu et al., "Impaired olfaction in mice lacking aquaporin-4 water channels," FASEB J. 22(9):3216-3223 (2008).
Lu et al., "The human AQP4 gene: definition of the locus encoding two water channel polypeptides in brain," Proc. Natl. Acad. Sci. U. S. A. 93(20):10908-10912 (1996).
Mader et al., "Patterns of antibody binding to aquaporin-4 isoforms in neuromyelitis optica," PLoS One 5(5):e10455 (2010).
Manley et al., "Aquaporin-4 deletion in mice reduces brain edema after acute water intoxication and ischemic stroke," Nat. Med. 6(2):159-163 (2000).
Marignier et al., "Oligodendrocytes are damaged by neuromyelitis optica immunoglobulin G via astrocyte injury," Brain 133(9):2578-2591 (2010).
Martinez and Cossart, "Early signaling events involved in the entry of Rickettsia conorii into mammalian cells," J. Cell Sci. 117(Pt 21):5097-5106 (2004).
Martinez et al., "Ku70, a component of DNA-dependent protein kinase, is a mammalian receptor for Rickettsia conorii," Cell Dec. 16, 2005;123(6):1013-1023 (2005).
Matiello et al., "NMO-IgG predicts the outcome of recurrent optic neuritis," Neurology 70(23):2197-2200 (2008).
O'Connor et al., "Self-antigen tetramers discriminate between myelin autoantibodies to native or denatured protein," Nat. Med. 13(2):211-217 (2007) (Epub Jan. 12, 2007).
Owens et al., "Antibodies produced by clonally expanded plasma cells in multiple sclerosis cerebrospinal fluid," Ann. Neurol. 65(6):639-649 (2009).
Saadoun et al., "Neuromyelitis optica MOG-IgG causes reversible lesions in mouse brain," Acta Neuropathol. Commun. 2:35 (2014).
Chan, A. et al. (Oct. 2010, e-published Aug. 4, 2010). "Serum antibodies to conformational and linear epitopes of myelin oligodendrocyte glycoprotein are not elevated in the preclinical phase of multiple sclerosis," Mult Scler 16(10):1189-1192.
O'Connor, K.C. et al. (Feb. 2007, e-published Jan. 12, 2007). "Self-antigen tetramers discriminate between myelin autoantibodies to native or denatured protein," Nat Med 13(2):211-217.
Sriram, S. et al. (Dec. 2005). "Experimental allergic encephalomyelitis: a misleading model of multiple sclerosis," Ann Neurol 58(6):939-945.
GenBank Accession AB135584.1 (May 10, 2008). "Homo sapiens DNA STS on chromosome X., DXS1005i, sequence tagged site," 2 pages.
GenBank Accession BAF64542.1 (Jul. 23, 2016), Immunoglobulin light chain, partial [Homo sapiens], 2 pages.

* cited by examiner

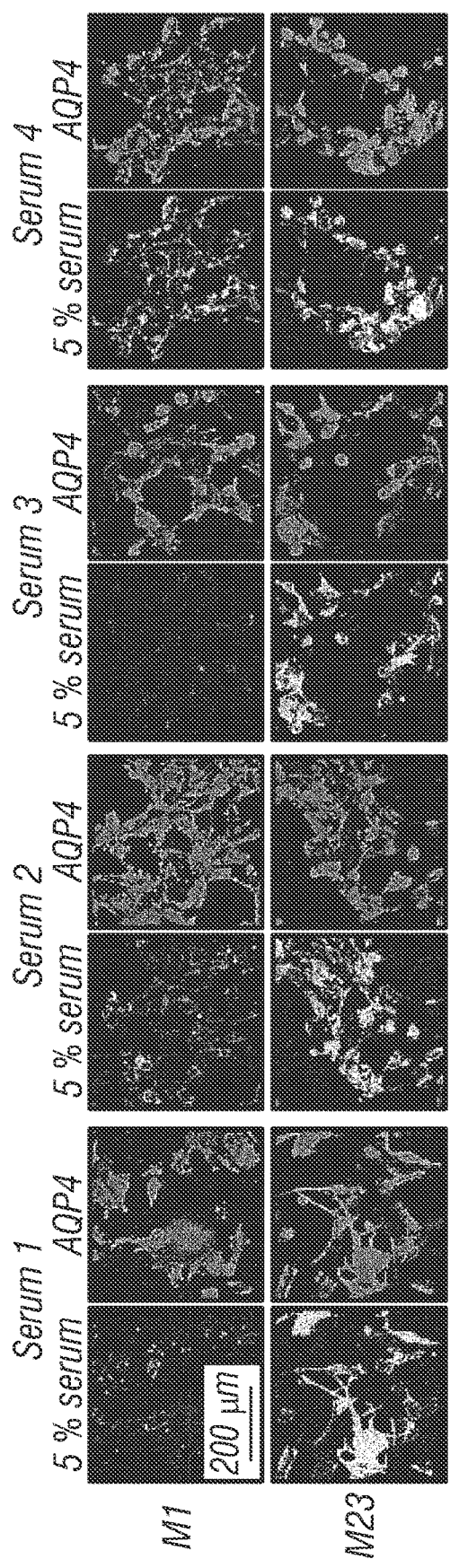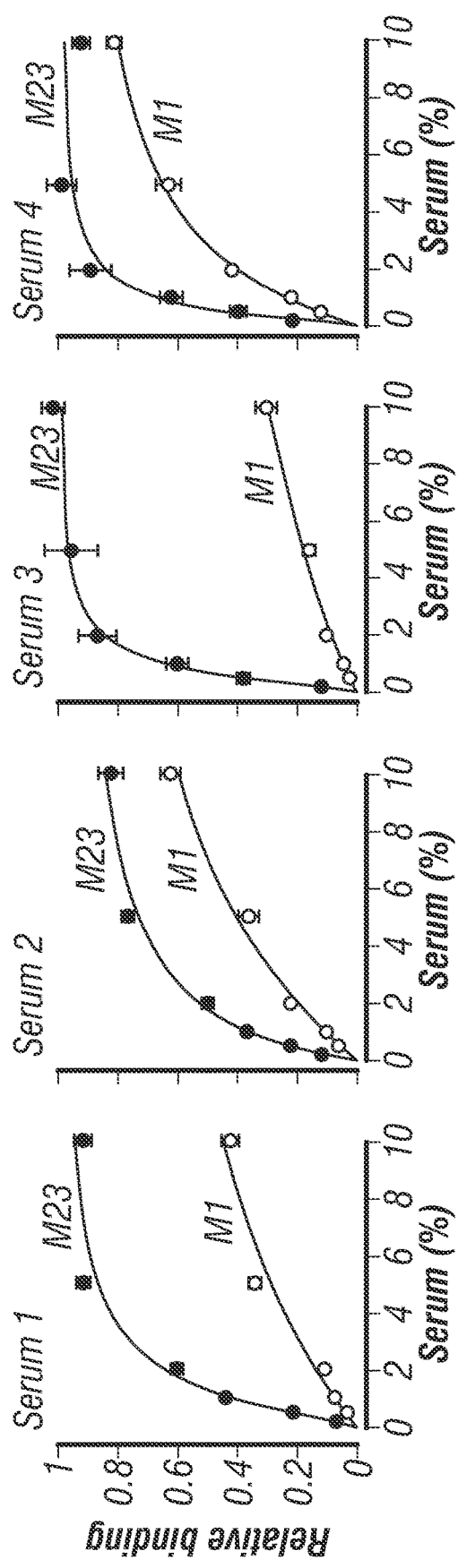
FIG. 3A
FIG. 3B

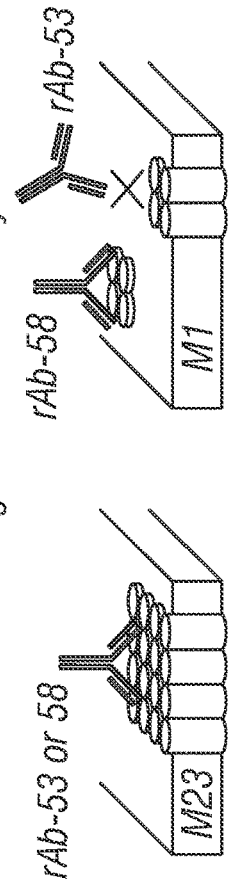
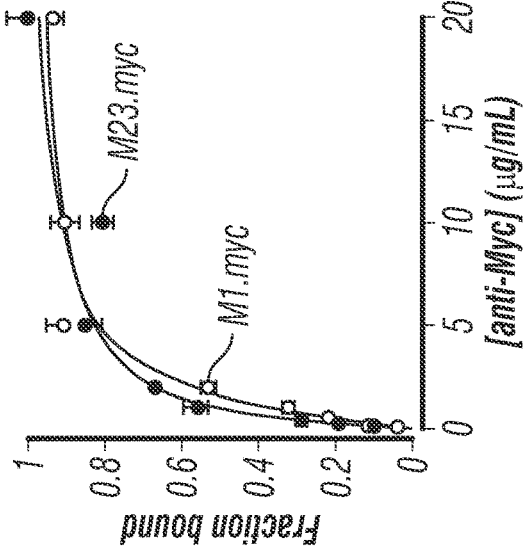
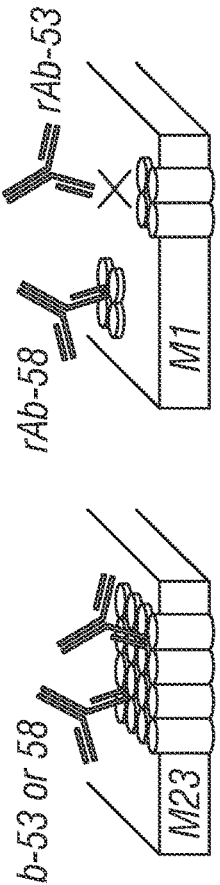
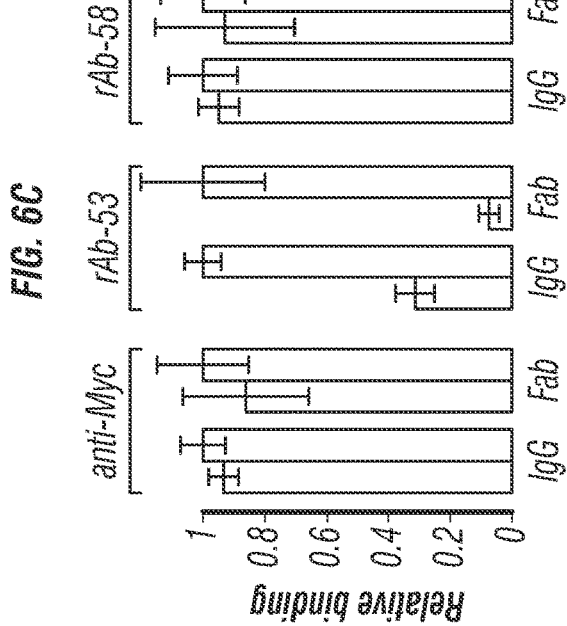
FIG. 6B
FIG. 6C
FIG. 6D

United States Patent

COMPOSITIONS AND METHODS FOR THE TREATMENT OF NEUROMYELITIS OPTICA

This application is a national phase application under 35 U.S.C. S 371 of International Application No. PCT/US2012/034662, filed Apr. 23, 2012, which claims benefit of priority to U.S. Provisional Application Ser. No. 61/477,955 filed Apr. 21, 2011, the entire contents of which are hereby incorporated by reference.

This invention was made with government support under grant numbers EY13574, EB00415, DK35124, HL73856, DK86125 and DK72517 awarded by the National Institutes of Health (NIH). The government has certain rights in the invention.

BACKGROUND OF THE INVENTION

1. Field of the Invention

The present invention relates generally to the fields of medicine, immunology, neurology and pathology. More particularly, it concerns the development of immunoreagents for use in treating neuromyelitis optica (NMO).

2. Background of the Invention

AQP4 (aquaporin-4) is a water channel expressed in astrocytes throughout the central nervous system (Lennon et al., 2005) which is involved in water balance in brain (Manley et al., 2000; Papadopoulos et al., 2004) and spinal cord (Saadoun et al., 2008), sensory signal transduction (Li and Verkman, 2001; Lu et al., 2008) and neuroexcitatory phenomena including seizure activity (Binder et al., 2006) and cortical spreading depression (Padmawar et al., 2005) and astrocyte migration and glial scarring (Saadoun et al., 2005; Auguste et al., 2007). AQP4 is expressed in astrocytes as two major isoforms: a long (M1) isoform with translation initiation at Met-1, and a shorter (M23) isoform with translation initiation at Met-23 (Hasegawa et al., 1994; Jung et al., 1994; Yang et al., 1995; Lu et al., 1996). M23 AQP4 assembles in membranes as regular square arrays called orthogonal arrays of particles (OAPs), which were originally seen by freeze-fracture electron microscopy (Landis and Reese, 1974; Wolburg, 1995). OAP formation by M23 results from tetramer-tetramer interactions involving residues just downstream of Met-23 at its cytoplasmic N-terminus, while residues in M1 AQP4 just upstream of Met-23 disrupt this interaction (Crane and Verkman, 2009). While M1 does not form OAPs on its own, it can co-assemble with M23 in heterotetramers that limit OAP size (Neely et al., 1999; Furman et al., 2003; Crane et al. (2009); Tajima et al., 2010). The biological significance of OAP formation by AQP4 remains unknown, with speculated functions including cell-cell adhesion, enhanced AQP4 water permeability, and AQP4 polarization to astrocyte end-feet.

A defining feature of the neuroinflammatory demyelinating disease neuromyelitis optica (NMO) is the presence of serum autoantibodies (NMO-IgG) against AQP4. The presence of NMO-IgG is specific for NMO, and in some reports serum NMO-IgG titers correlate with NMO disease activity (Matiello et al., 2008; Jujus et al., 2008). Studies in rodents suggest that NMO-IgG is pathogenic in NMO. Human NMO-IgG produces many features of NMO disease in rats with pre-existing experimental autoimmune encephalomyelitis (Bennett et al., 2009; Bradl et al., 2009) or pre-treated with complete Freund's adjuvant (Kinoshita et al., 2010), and in naïve mice when injected together with human complement (Saadoun et al., 2010). These animals develop characteristic NMO lesions with neuroinflammation, perivascular deposition of activated complement, demyelination, and loss of astrocyte GFAP and AQP4 immunoreactivity. At present, there remain limited treatments for symptoms of NMO with no known therapies that prevent the underlying inflammatory event.

SUMMARY OF THE INVENTION

Thus, in accordance with the present invention, there is provided a method of treating a subject with neuromyelitis optica (NMO) spectrum disease comprising administering to the subject an reagent comprising an anti-aquaporin-4 (AQP4) antibody or an antigen binding fragment thereof, wherein the reagent lacks effector functions of an intact antibody. The subject may be a human subject. Administering may comprise intraocular, intra-arterial, subcutaneous, intravenous administration or intrathecal route of administration. The reagent may comprise a mutated Fc region lacking effector functions, such as an IgG1 sequence that contains L234A/L235A amino acid substitutions, a L234A/L235A/G237A amino acid substitution, and/or a K322A amino acid substitution in the Fc region. The reagent may also comprises IgG2 or IgG3 sequences with substitutions in the Fc region that abrogate effector functions such as complement activation. Alternatively, the reagent may be an IgG4 antibody. The reagent may comprise a chemically modified Fc region. The reagent may also comprise an antibody Fab fragment and lacks an Fc region, or an antibody Fab fragment fused to a non-antibody protein segment. The reagent may also comprise a single chain antibody or F(ab')$_2$. The antibody may be optimized for AQP4 binding by mutating certain residues in the antigen-binding region.

Treating may comprise reducing one or more of retinal ganglion cell death, optic nerve injury, spinal cord injury, or axonal transection. Treating may comprise reducing one or more of optic nerve demyelination, spinal cord demyelination, astrocyte death or oligodendrocyte death. The reagent may be administered more than once, including chronically and daily. The reagent may be administered upon onset of or following an NMO attack, such as within about 1 hour, 6 hours, 12 hours, 24 hours or two days of an NMO attack. The method may further comprise administering to the subject a second agent that treats one or more aspect of NMO. The second agent may be administered at the same time as the reagent, or either before or after the reagent. The method may further comprise assessing the patient for positive NMO-IgG (AQP4) serology. The subject may exhibit positive NMO-IgG (AQP4) serology. The subject may exhibit one or more of transverse myelitis, optic neuritis or other unrelated neurologic dysfunction (e.g., protracted nausea or vomiting).

Other embodiments include a method of chronically treating a subject to prevent or reduce exacerbations of neuromyelitis optica (NMO) spectrum disease in a subject comprising administering to said subject an reagent comprising an anti-aquaporin-4 (AQP4) antibody or an antigen binding fragment thereof, wherein said reagent lacks effector functions of an intact antibody, and a method of preventing or inhibiting the progression of neuromyelitis optica (NMO) spectrum disease in a subject comprising administering to said subject an reagent comprising an anti-aquaporin-4 (AQP4) antibody or an antigen binding fragment thereof, wherein said reagent lacks effector functions of an intact antibody.

In another embodiment, there is provided a reagent comprising an anti-aquaporin-4 (AQP4) antibody or an antigen binding fragment thereof, wherein said reagent lacks effector functions of an intact antibody. The reagent may comprise a mutated Fc region lacking effector functions, such as one comprising an IgG1 sequence that contains L234A/L235A amino acid substitutions, a L234A/L235A/G237A amino acid substitution, and/or comprising an IgG1 sequence having a K322A substitution, or even a mutated IgG2 or IgG3 Fc region. The may be reagent an IgG4 antibody. The reagent may comprise a chemically-modified Fc region. The reagent may comprise an antibody Fab fragment and lacks an Fc region. The reagent may comprise an antibody Fab fragment fused to a non-antibody protein segment. The reagent may comprise a single chain antibody or F(ab)$_2$. It is contemplated that any method or composition described herein can be implemented with respect to any other method or composition described herein.

The antibody or antigen binding fragment of the antibodies set forth above may comprise a light chain variable sequence according to SEQ ID NO:6 or a sequence having 95%, 90%, 85%, or 80% identity to SEQ ID NO:6, and a heavy chain sequence according to SEQ ID NO:8, or a sequence having 95%, 90%, 85%, or 80% identity to SEQ ID NO:8; or a light chain variable sequence according to SEQ ID NO:10 or a sequence having 95%, 90%, 85%, or 80% identity to SEQ ID NO:10, and a heavy chain sequence according to SEQ ID NO:12 or a sequence having 95%, 90%, 85%, or 80% identity to SEQ ID NO:12; or a light chain variable sequence according to SEQ ID NO:19 or a sequence having 95%, 90%, 85%, or 80% identity to SEQ ID NO:19, and a heavy chain variable sequences SEQ ID NO:17 or a sequence having 95%, 90%, 85%, or 80% identity to SEQ ID NO:17. The antibody antigen binding fragment may be encoded by a light chain variable sequence according to SEQ ID NO:5 or a sequence having 85%, 80%, 75% or 70% identity to SEQ ID NO:5, and a heavy chain sequence according to SEQ ID NO:7, or a sequence having 85%, 80%, 75% or 70% identity to SEQ ID NO:7; or encoded by a light chain variable sequence according to SEQ ID NO:9 or a sequence having 85%, 80%, 75% or 70% identity to SEQ ID NO:9, and a heavy chain sequence according to SEQ ID NO:11 or a sequence having 85%, 80%, 75% or 70% identity to SEQ ID NO:11; or encoded by a light chain variable sequence according to SEQ ID NO:20 or a sequence having 85%, 80%, 75% or 70% identity to SEQ ID NO:20, and a heavy chain sequence according to SEQ ID NO:18 or a sequence having 85%, 80%, 75% or 70% identity to SEQ ID NO:18. The antibody antigen binding fragment may comprise the antigen binding fragment of an antibody having laboratory designation rAb-53, rAb09-3-33 or rAb-58.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1A) AQP4 monomers (cylinders) shown as assembling into tetramers (top) or OAPs (bottom). NMO-IgG (green) binds AQP4 at an extracellular domain, and a reference AQP4 antibody (red) binds on the cytoplasmic side. (FIG. 1B) The reference AQP4 antibody binds to the C-terminus of AQP4, independent of the AQP4 N-terminal isoform and OAP formation.

(FIG. 2A) Confocal fluorescence images show U87MG cells stably expressing M1 (top) or M23 (bottom) and labeled with NMO-IgG (green) and C-terminal anti-AQP4 antibody (red). (FIG. 2B) Total internal reflection fluorescence images show distinct OAPs in M23-expressing cells (bottom), and a smooth fluorescence staining pattern in M1-expressing cells (top). (FIG. 2C) AQP4 immunoblot following blue-native gel electrophoresis (top) and Tricine SDS-PAGE (bottom) of stable AQP4-expressing U87MG cell lysates. (FIG. 2D) Measured green-to-red fluorescence ratios (G/R) in U87MG cells after stable (grey) or transient (white) transfection with M1 or M23 AQP4, and labeled with the indicated recombinant monoclonal NMO-IgG.

FIGS. 3A-B. Differential binding of NMO-IgG in NMO patient serum to M1 vs. M23 AQP4. (FIG. 3A) M1 and M23 expressing U87MG cells stained with 5% NMO serum (green) from four patients, and with reference AQP4 antibody (red). (FIG. 3B) Binding curves for the NMO patient sera to M1 vs. M23 AQP4 (mean±S.E., n=5). Curves represent fit to single-site binding model.

(FIG. 4A) Representative fluorescence micrographs for binding of rAb-53 and rAb-58 (green) as a function of concentration, together with reference AQP4 antibody (red). (FIG. 4B) Binding curves for rAb-53 (left), rAb-58 (middle) and rAb-186 (right) to M1 vs. M23 AQP4 (mean±S.E., n=5). Curves represent fit to a single-site binding model.

(FIG. 5A) Binding of rAb-53 (left) and cumulative distributions of diffusion range (right), measured by quantum dot single-particle tracking, for M1 and M23 AQP4 mixtures at indicated ratios (mean±S.E., n=5). (FIG. 5B) Binding of rAb-53 (left) and diffusion range (right) for M23 AQP4 with M1 mutant CCA at indicated ratios (mean±S.E., n=5). (FIG. 5C) Binding of rAb-53 (left) and diffusion range (right) for AQP4 mutants M23-F26Q (red) and M23-G28P (green) (mean±S.E., n=5).

FIG. 6A-D. Mechanism of increased NMO-IgG binding affinity to array-assembled AQP4. (FIG. 6A) Human IgG and AQP4 crystal structures (Harris et al., 1998; Ho et al., 2009) showing relative size of the AQP4 tetramer compared with spacing between Fab binding sites in whole IgG. (FIG. 6B) Predictions of bivalent vs. monovalent binding mechanisms. AQP4 monomers (cylinders) are shown as assembled in tetramers (M1) or OAPs (M23). NMO-IgG (green) binds either mono- or bivalently to (unknown) extracellular domains on AQP4. (FIG. 6C) Binding of monoclonal mouse anti-Myc to cells expressing Myc-tagged M1 vs. M23 AQP4. (FIG. 6D) Relative M1-to-M23 binding of whole IgG or purified Fab fragments of mouse anti-Myc (left), rAb-53 (middle) and rAb-58 (right) at a fixed concentration (mean±S.E., n=5).

(FIG. 7A) Crystal structure of AQP4 tetramer shown on the same scale with that of an IgG1 antibody. (FIG. 7B) Surface plasmon resonance measurement of recombinant antibody binding to AQP4-reconstituted proteoliposomes showing binding/unbinding kinetics of rAb-53 (left) at different concentrations, and different NMO rAbs (right) at fixed concentration. (FIG. 7C) Binding and unbinding kinetics rAb-53 (25 µg/ml) to AQP4-expressing U87MG cells. Binding measured by incubation with rAb-53 for specified times followed by rinsing, fixation and fluorescent secondary antibody addition. Washout measured after 60 min incubation with rAb-53 followed by washout with antibody-free buffer for specified times. Top: Representative micrographs showing cell surface staining by rAb-53 (red). Bottom: Averaged binding data (mean±S.E., n=4).

(FIG. 8A) Schematic of rAb-53 showing heavy (VH) and light (VL) chain variable regions, light chain constant region (CL), and IgG1 heavy chain constant regions (CH1-CH3). Locations of amino acid mutations introduced in the CH2 domain to reduce CDC (K322A), ADCC (K326W/E333S) or both (L234A/L235A). (FIG. 8B) Surface plasmon resonance measurements of binding and washout of a mutated rAb-53 (L234A/L235A) to AQP4-reconstituted proteoliposomes. (FIG. 8C) Mutated rAb-53 block binding of Cy3-labeled (non-mutated)rAb-53 to AQP4-expressing cells. Cy3 fluorescence imaged in AQP4-null (left-most panel) or AQP4-expressing (other panels) cells incubated with 20 µg/ml Cy3-rAb-53 for 1 h in the absence or presence of indicated (unlabeled) antibodies at 100 µg/ml. (FIG. 8D) Unrelated monoclonal NMO antibodies and human NMO serum blocks AQP4 binding of Cy3-labeled rAb-53. Cy3 fluorescence imaged in cells incubated with 20 µg/ml Cy3-rAb-53 for 1 h in the absence or presence of 10% control (non-NMO) or NMO patient serum, or 100 µg/ml recombinant NMO monoclonal antibody rAb-186.

(FIG. 9A) Live/dead cell assay after 90 min exposure of AQP4-expressing CHO cells to human complement together with control (non-NMO) mAb or rAb-53 (2.5 µg/ml, non-mutated or mutated). Percentage dead cells summarized at the right (mean±S.E., n=4-6, * P<0.001 compared to rAb-53 alone). (FIG. 9B) Assay as in A done with complement+rAb-53, in the presence of 12.5 µg/ml of the indicated aquaporumabs. (FIG. 9C) Live/dead cell assay after 60 min exposure to control (non-NMO) serum or NMO patient sera in the presence of complement, and the absence or presence of indicated aquaporumabs. (FIG. 9D) ADCC assay done using AQP4-expressing CHO cells incubated with NK-cells together with control (non-NMO) mAb or rAb-53 or aquaporumab (individually), or rAb-53 and aquaporumab together.

(FIG. 10A) Panel of mouse brain sections at 24 h after intracerebral injection, stained with hematoxylin and eosin (H&E) and Luxol fast blue (myelin), and immunostained brown for AQP4 (AQP4) and C5b-9 (activated complement). Intracerebral injections were made of NMO-IgG (purified IgG from NMO serum) and human complement, without or with aquaporumab (Aqmab), with controls (control IgG, AQP4 knockout mice, Aqmab alone). Pink line indicates areas of absent Luxol fast blue staining or AQP4 immunoreactivity. Black line outlines the injected hemisphere and shows needle tract. Arrows, neutrophils; arrowheads, perivascular C5b-9 immunoreactivity; V, vessel. Bar, 50 µm. (FIG. 10B) AQP4 and myelin loss quantified as % area outlined with pink/area outlined with black (S.E.M., 5 mice per group, * P<0.01). (FIG. 10C) % myelin and AQP4 loss shown for five pairs of mice, each pair injected with NMO-IgG from a different NMO patient with human complement, without or with aquaporumab.

(FIG. 11A) Ex vivo spinal cord slice culture model in which slices were cultured for 7 days, followed by 3 days in the presence of NMO-IgG (purified IgG from NMO serum) and human complement, without or with aquaporumab (Aqmab). Immunostaining shown for AQP4, GFAP and myelin. Controls include non-NMO IgG, NMO-IgG or Aqmab alone, Aqmab with complement, and slice cultures from AQP4 null mice. (FIG. 11B) NMO lesion scores (see Methods) (S.E.M., n=4-5, P<0.001)

DESCRIPTION OF ILLUSTRATIVE EMBODIMENTS

Figure 1B:
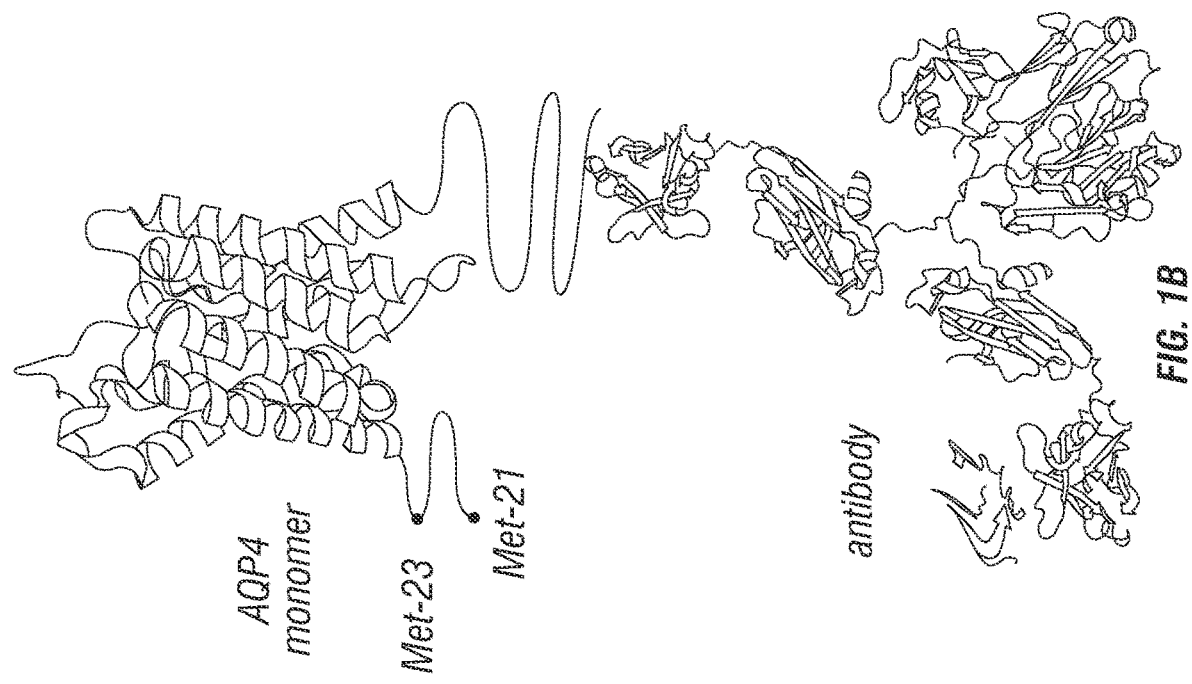
FIGS. 1A-B. Schematic of the two-color ratio imaging method for quantitative measurement of NMO-IgG binding to AQP4 isoforms.

The inventors previously showed that NMO patient serum and a recombinant monoclonal NMO-IgG were each able to bind to both the M23 and M1 isoforms of AQP4 (Crane et al., 2009), which contradicted an earlier study reporting undetectable binding to M1 AQP4 of serum from one NMO patient (Nicchia et al., 2009). A prior report that analyzed a single NMO serum specimen concluded that OAPs are the sole target of NMO-IgG (Nicchia et al., 2009). However, this conclusion cannot be correct because the clinical serum assay for serum anti-AQP4 autoantibody uses M1 AQP4 (Wingerchuk et al., 2006), and the inventors (Bennett et al., 2009; Crane et al., 2009) and others (Hinson et al., 2007) reported strong binding of some NMO autoantibodies to cells expressing only M1 AQP4. While a recent study showed that clinical sensitivity of the NMO-IgG binding assay could be improved by using M23-expressing cells (Mader et al., 2010), there have been no quantitative studies of NMO-IgG AQP4 specificity, nor has the affinity of NMO-IgG binding to AQP4 isoforms been measured.

The inventors used quantitative ratio imaging to measure NMO autoantibody binding to AQP4 in which NMO-IgG binding, as revealed by a fluorescent secondary antibody, was normalized to total AQP4 protein using an antibody directed against the AQP4 C-terminus. For these studies, the inventors identified a human astrocyte-derived cell line that expressed AQP4 in a plasma membrane pattern after transfection. The strategy to assess independently the AQP4 isoform and OAP specificities of NMO-IgG binding was to express M1 and M23 AQP4 in different ratios, or an M23 mutant containing an OAP-disrupting, single amino acid substitution in its N-terminus. Measurements were made on serum samples from NMO patients, as well as purified monoclonal antibodies generated by recombinant technology from cloned sequences derived from plasma cells in the cerebrospinal fluid of an NMO patient. Studies using monoclonal NMO antibodies allowed, for the first time, the measurement of absolute binding affinities of NMO-IgG to AQP4. Studies using OAP-deficient mutants of M23 AQP4 and various heterotetramer-forming mixed AQP4 isoforms indicated enhanced NMO-IgG binding to AQP4 in OAPs.

Studies comparing whole NMO-IgG to purified Fab fragments suggested a molecular basis for the enhanced NMO-IgG binding to array-assembled AQP4.

In addition, the inventors generated non-pathogenic human recombinant monoclonal anti-AQP4 antibodies, which they call "aquaporumab," that selectively block NMO-IgG binding to AQP4 and prevent NMO-IgG-induced cell killing and lesion formation. Aquaporumab comprises a tight-binding anti-AQP4 Fab and a mutated Fc that lacks functionality for complement- and cell-mediated cytotoxicity. In AQP4-expressing cell cultures, aquaporumab blocked binding of NMO-IgG in human sera, reducing to near zero complement- and cell-mediated cytotoxicity. Aquaporumab prevented the development of NMO-like lesions in an ex vivo spinal cord slice model of NMO and in an in vivo mouse model of NMO produced by intracerebral injection of NMO-IgG and complement. Aquaporumab alone did not cause pathology. The broad efficacy of aquaporumab inhibition is likely due to steric competition because of its large physical size compared to the extracellular domain of AQP4. These results provide support for aquaporumab therapy of NMO.

These and other aspects of the invention are described in greater detail below.

I. Neuromyelitis Optica (NMO)

Neuromyelitis optica (NMO), also known as Devic's disease or Devic's syndrome, is an autoimmune, inflammatory disorder in which a person's own immune system attacks the optic nerves and spinal cord. This produces an inflammation of the optic nerve (optic neuritis) and the spinal cord (myelitis). Although inflammation may also affect the brain, the lesions are different from those observed in the related condition multiple sclerosis (MS). Spinal cord lesions lead to varying degrees of weakness or paralysis in the legs or arms, loss of sensation (including blindness), and/or bladder and bowel dysfunction.

NMO is a rare disorder which resembles MS in several ways, but requires a different course of treatment for optimal results. NMO has also been suggested to be a variant form of acute disseminated encephalomyelitis. The target of the autoimmune attack in at least some patients with NMO has been identified—it is a protein of the nervous system cells called aquaporin 4 or AQP4.

The main symptoms of NMO are loss of vision and spinal cord function. As for other etiologies of optic neuritis, the visual impairment usually manifests as decreased visual acuity, although visual field defects, or loss of color vision may occur in isolation or prior to formal loss of acuity. Spinal cord dysfunction can lead to muscle weakness, reduced sensation, or loss of bladder and bowel control. The typical patient has an acute and severe spastic weakness of the legs (paraparesis) or all four limbs (tetraparesis) with sensory signs, often accompanied by loss of bladder control.

NMO is similar to MS in that there is immune-mediated destruction of the myelin surrounding nerve cells. Unlike standard MS, the attacks are not targeted against the myelin producing cells (oligodendrocytes) or primarily mediated by the immune system's T cells but rather by antibodies called NMO-IgG, or simply NMO antibodies. These antibodies target AQP4 in the cell membranes of astrocytes which acts as a channel for the transport of water across the cell membrane. AQP4 is found in the processes of the astrocytes that surround the blood-brain barrier, a system responsible for preventing substances in the blood from crossing into the brain. The blood-brain barrier is weakened in NMO, but it is currently unknown how the NMO-IgG immune response leads to oligodendrocyte death and demyelination.

Most research into the pathology of NMO has focused on the spinal cord. The damage in the spinal cord can range from inflammatory demyelination to necrotic damage of the white and grey matter. The inflammatory lesions in NMO have been classified as type II lesions (complement mediated demyelination), but they differ from MS pattern II lesions in their prominent perivascular distribution. Therefore, the pattern of inflammation is often quite distinct from that seen in MS.

The Mayo Clinic proposed a revised set of criteria for diagnosis of NMO in 2006. The new guidelines for diagnosis require two absolute criteria plus at least two of three supportive criteria being:
  1. Absolute criteria:
  Optic neuritis
  Acute myelitis
  2. Supportive criteria:
  Brain MRI not meeting criteria for MS at disease onset
  Spinal cord MRI with contiguous T2-weighted signal abnormality extending over 3 or more vertebral segments, indicating a relatively large lesion in the spinal cord
  NMO-IgG seropositive status. The NMO-IgG test checks the existence of antibodies against the aquaporin 4 antigen.

After the development of the NMO-IgG test, the spectrum of disorders that comprise NMO was expanded. The NMO spectrum is now believed to consist of:
  Standard NMO, according to the diagnostic criteria described above
  Limited forms of NMO, such as single or recurrent events of longitudinally extensive myelitis, and bilateral simultaneous or recurrent optic neuritis
  Asian optic-spinal MS. This variant can present CNS involvement like MS
  Longitudinally extensive myelitis or optic neuritis associated with systemic autoimmune disease
  Optic neuritis or myelitis associated with lesions in specific brain areas such as the hypothalamus, periventricular nucleus, and brainstem Whether NMO is a distinct disease or part of the wide spectrum of multiple sclerosis is debated. In general, NMO is now considered to be a distinct neuro-inflammatory disorder. NMO differs in that it usually has more severe sequelae after an acute episode than in MS, MS infrequently presents as transverse myelitis, and oligoclonal bands in the CSF, as well as white matter lesions on brain MRI, are uncommon in Devic's disease but occur in over 90% of MS patients. Recently, it has been found that antiviral immune response distinguishes multiple sclerosis and neuromyelitis optica.

NMO has been associated with many systemic diseases, based on anecdotal evidence of some NMO patients with a comorbid condition. Such conditions include: collagen vascular diseases, autoantibody syndromes, infections with varicella-zoster virus, Epstein-Barr virus, and HIV, and exposure to clioquinol and antituberculosis drugs.

Currently, there is no cure for NMO, but symptoms can be treated. Some patients recover, but many are left with impairment of vision and limbs, which can be severe. Attacks are treated with short courses of high dosage intravenous corticosteroids such as methylprednisolone IV. When attacks progress or do not respond to corticosteroid treatment, plasmapheresis can be an effective treatment.

Clinical trials for these treatments contain very small numbers, and most are uncontrolled.

No controlled trials have established the effectiveness of treatments for the prevention of attacks. Many clinicians agree that long term immunosuppression is required to reduce the frequency and severity of attacks, while others argue the exact opposite. Commonly used immunosuppressant treatments include azathioprine (Imuran) plus prednisone, mycophenolate mofetil plus prednisone, Rituximab, Mitoxantrone, intravenous immunoglobulin (IVIG), and Cyclophosphamide. In 2007, NMO was reported to be responsive to glatiramer acetate and to low-dose corticosteroids. Normally, there is some measure of improvement in a few weeks, but residual signs and disability may persist, sometimes severely.

The disease can be monophasic, i.e., a single episode with permanent remission. However, at least 85% of patients have a relapsing form of the disease with repeated attacks of transverse myelitis and/or optic neuritis. In patients with the monophasic form the transverse myelitis and optic neuritis occur simultaneously or within days of each other. On the other hand, patients with the relapsing form are more likely to have weeks or months between the initial attacks and to have better motor recovery after the initial transverse myelitis event. Relapses usually occur early with about 55% of patients having a relapse in the first year and 90% in the first 5 years. Unlike multiple sclerosis, NMO rarely has a secondary progressive phase in which patients have increasing neurologic decline between attacks without remission. Instead, disabilities arise from the acute attacks.

Approximately 20% of patients with monophasic NMO have permanent visual loss and 30% have permanent paralysis in one or more legs. Among patients with relapsing NMO, 50% have paralysis or blindness within 5 years. In some patients (33% in one study), transverse myelitis in the cervical spinal cord resulted in respiratory failure and subsequent death. However, the spectrum of NMO has widened due to improved diagnostic criteria, and the options for treatment have improved; as a result, researchers believe that these estimates will be lowered.

The prevalence and incidence of NMO has not been established partly because the disease is underrecognized and often confused with MS. NMO is more common in women than men, with women comprising over ⅔ of patients and more than 80% of those with the relapsing form of the disease. According to the Walton Centre in England, "NMO seems to be present across the world unlike MS, which has a higher incidence in temperate climates and white races. Africans and Asians especially in Far East may have a higher risk of NMO, although the exact incidence of this disease is unknown, making specific conclusions difficult." Although many people who have NMO were initially mis-diagnosed with MS, 35% of African Americans are often mis-diagnosed with MS when they really have NMO. NMO is more common in Asiatic people than Caucasians. In fact, Asian optic-spinal MS (which constitutes 30% of the cases of MS in Japan) has been suggested to be identical to NMO (differences between optic-spinal and classic MS in Japanese patients). In the indigenous populations of tropical and subtropical regions, MS is rare, but when it appears it often takes the form of optic-spinal MS. The majority of NMO patients have no affected relatives, and it is generally regarded as a non-familial condition.

II. Producing Monoclonal Antibodies

A. General Methods

It will be understood that monoclonal antibodies binding to AQP4 will have utilities in several applications. These include the production of diagnostic kits for use in detecting and diagnosing NMO, as well as for treating NMO. In these contexts, one may link such antibodies to diagnostic or therapeutic agents, use them as capture agents or competitors in competitive assays, or use them individually without additional agents being attached thereto. The antibodies may be mutated or modified, as discussed further below. Methods for preparing and characterizing antibodies are well known in the art (see, e.g., Antibodies: A Laboratory Manual, Cold Spring Harbor Laboratory, 1988; U.S. Pat. No. 4,196,265).

The methods for generating monoclonal antibodies (MAbs) generally begin along the same lines as those for preparing polyclonal antibodies. The first step for both these methods is immunization of an appropriate host or identification of subjects who are immune due to prior natural infection. As is well known in the art, a given composition for immunization may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine. As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

The recombinant antibodies of the present invention are producing using single plasmablasts or b cells isolated from the CSF of affected individuals. Blood can also be used, although plasmablasts are somewhat less prevalent in that fluid. The antibody heavy and light chain sequences are identified by RT-PCR. The identified pair of heavy and light chain are then reengineered using standard cloning techniques into expression vectors and transfected into mammalian cell lines to produce antibody.

MAbs produced by either means may be further purified, if desired, using filtration, centrifugation and various chromatographic methods such as FPLC or affinity chromatography. Fragments of the monoclonal antibodies of the invention can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

It also is contemplated that a molecular cloning approach may be used to generate monoclonals. For this, RNA can be isolated from the hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately $10^4$ times as many antibodies can be produced and screened in a single round, and that new specificities are generated by H and L chain combination which further increases the chance of finding appropriate antibodies.

Other U.S. patents, each incorporated herein by reference, that teach the production of antibodies useful in the present invention include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

B. Antibodies of the Present Invention

Antibodies according to the present invention may be defined, in the first instance, by their binding specificity, which in this case is for AQP4. Those of skill in the art, by assessing the binding specificity/affinity of a given antibody using techniques well known to those of skill in the art, can determine whether such antibodies fall within the scope of the instant claims.

In one aspect, there is provided a monoclonal antibody that binds to AQP4. A particular type of antibody that is one that lacks Fc-related effector functions. Indeed, since antibodies to AQP4 are disease-causing, one must modify such AQP4 antibodies in order to render them not only safe, but protective. Such antibodies may be produced by mutating the Fc region of antibodies that exhibit such functions (e.g., IgG1 or IgG2 or IgG3), by using antibodies that naturally lack such functions (IgG4), or by chemically modifying any of such antibodies so as to render them ineffective at complement activation and immune cell recruitment.

In a second aspect, the antibodies may be defined by virtue of the region of the structures to which they bind. For example, the extracellar surface and orthogonal arrays of AQP4 provide a unique platform for antibody binding.

In a third aspect, the antibodies may be defined by their variable sequence that determine their binding specificity. Examples are provided below:

rAb53 Heavy Chain Sequence (Variable Region)
Nucleic Acid (SEQ ID NO: 7):
CAGGTGCAGCTGCAGGAGTCGGGCGCAGGACTGGTGAAGCCTTCGGAGAC

CCTGTCCCTCACCTGCACTGTCTCTGGTGGCTCCATCAGTGGTCACTACT

GGAACTGGATCCGGCAGCCCCCAGGGAAGGGACTGGAGTGGATTGGGTAC

ATCCATTACAGTGGGAGCACCAACTACAACCCCTCCCTCAAGAGTCGAGT

CACCATATCAGTGGACACGTCCAAGAACCAGTTCTCCCTGAAGCTGAGCT

CTGTGACCGCTGCGGACACGGCCGTGTATTACTGTGCGAGAGCAGAGGGG

AGAGGATGGAGTGCTTTCTACTACTACTACATGGAAGTCTGGGGCAAAGG

GTCCACGGTCTCCGTCTCCTCA rAb53 Heavy Chain Sequence (Variable Region)
Protein (SEQ ID NO: 8):
QVQLQESGAGLVKPSETLSLTCTVSGGSISGHYWNWIRQPPGKGLEWIGY

IHYSGSTNYNPSLKSRVTISVDTSKNQFSLKLSSVTAADTAVYYCARAEG

RGWSAFYYYYMEVWGKGSTVSVSS rAb53 Light Chain Sequence (Variable Region + IgK
Constant Region) Nucleic Acid (SEQ ID NO: 5):
GAAATTGTGTTGACACAGTCTCCAGGCACCCTGTCTTTGTCTCCAGGGGA

AAGAGCCACCCTCTCCTGCAGGGCCAGTCAGACTGTTCGCACCAACTACT

TAGCCTGGTTCCAGCAGAAACCTGGCCAGGCTCCCAGGCTCCTCATCTTT

GGTGCATCCAGCAGGGCCACTGGCATCCCAGACAGGTTCAGTGGCAGTGG

GTCTGGGACAGACTTCACTCTCACCATCAGCAGACTGGAGCCTGAAGATT

TTGCAGTGTATTACTGTCAGCAGTATGGTAGCTCACCGTGGACGTTCGGC

CAAGGGACCAAGGTGGAAATCAAACGAaCTGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGTTCGCCCGTCACAAAGAGCTTCAACAGGGGAGAGTGT rAb53 Light Chain Sequence (Variable Region + IgK
Constant Region) Protein (SEQ ID NO: 6):
EIVLTQSPGTLSLSPGERATLSCRASQTVRTNYLAWFQQKPGQAPRLLIF

GASSRATGIPDRFSGSGSGTDFTLTISRLEPEDFAVYYCQQYGSSPWTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The following sequences, described as "Mutant," are the exact sequences used in the Fc mutant constructs. rAb-53 was originally an IgG2 molecule, and the cloning steps used to construct the mutant IgG1 Fc regions retained some portion of the 5' IgG2 Fc sequence. At the amino acid level, the sequences are distinct from IgG1 at 4 amino acids in the first 35 aa. At the end of the IgG1 sequence, the inventors added a FLAG tag (LEDYKDDDDK; SEQ ID NO: 16). Therefore, the sequence is not technically human IgG1; it is different by 14/340 residues, or 4%. The final product is a mutated human IgG1.

Mutant Human IgG1 Fc K322 mutation Nucleic Acid (SEQ ID NO:3):
GCCTCCACCAAGGGCCCATCGGTCTTCCCCCTGGCGCCCTGCTCCAGGAGCACCT

CCGAGAGCACAGCGGCCCTGGGCTGCCTGGTCAAGGACTACTTCCCCGAACCGG

-continued

TGACGGTGTCGTGGAACTCAGGCGCCCTGACCAGCGGCGTGCACACCTTCCCGG

CTGTCCTACAGTCCTCAGGACTCTACTCCCTCAGCAGCGTGGTGACCGTGCCCTC

CAGCAGCTTGGGCACCCAGACCTACATCTGCAACGTGAATCACAAGCCCAGCAA

CACCAAGGTGGACAAGAAAGTTGAGCCCAAATCTTGTGACAAAACTCACACATG

CCCACCGTGCCCAGCACCTGAACTCCTGGGGGACCGTCAGTCTTCCTCTTCCCC

CCAAAACCCAAGGACACCCTCATGATCTCCCGGACCCCTGAGGTCACATGCGTG

GTGGTGGACGTGAGCCACGAAGACCCTGAGGTCAAGTTCAACTGGTACGTGGAC

GGCGTGGAGGTGCATAATGCCAAGACAAAGCCGCGGGAGGAGCAGTACAACAG

CACGTACCGTGTGGTCAGCGTCCTCACCGTCCTGCACCAGGACTGGCTGAATGGC

AAGGAGTACAAGTGCGCGGTCTCCAACAAAGCCCTCCCAGCCCCCATCGAGAAA

ACCATCTCCAAAGCCAAAGGGCAGCCCCGAGAACCACAGGTGTACACCCTGCCC

CCATCCCGGGATGAGCTGACCAAGAACCAGGTCAGCCTGACCTGCCTGGTCAAA

GGCTTCTATCCCAGCGACATCGCCGTGGAGTGGGAGAGCAATGGGCAGCCGGAG

AACAACTACAAGACCACGCCTCCCGTGCTGGACTCCGACGGCTCCTTCTTCCTCT

ACAGCAAGCTCACCGTGGACAAGAGCAGGTGGCAGCAGGGGAACGTCTTCTCAT

GCTCCGTGATGCATGAGGCTCTGCACAACCACTACACGCAGAAGAGCCTCTCCCT

GTCTCCGGGTAAACTCGAGGACTACAAGGACGATGACGATAAGTGA

Mutant Human IgG1 Fc K322 mutation Protein (SEQ ID NO: 4):
ASTKGPSVFPLAPCSRSTSESTAALGCLVKDYFPEPVTVSWNSGALTSGVHTFPAVLQ

SSGLYSLSSVVTVPSSSLGTQTYICNVNHKPSNTKVDKKVEPKSCDKTHTCPPCPAPE

LLGGPSVFLFPPKPKDTLMISRTPEVTCVVVDVSHEDPEVKFNWYVDGVEVHNAKT

KPREEQYNSTYRVVSVLTVLHQDWLNGKEYKCAVSNKALPAPIEKTISKAKGQPREP

QVYTLPPSRDELTKNQVSLTCLVKGFYPSDIAVEWESNGQPENNYKTTPPVLDSDGS

FFLYSKLTVDKSRWQQGNVFSCSVMHEALHNHYTQKSLSLSPGKLEDYKDDDDK*

Mutant Human IgG1 Fc L234A/L235A mutation Nucleic Acid (SEQ ID NO: 1):
GCCTCCACCAAGGGCCCATCGGTCTTCCCCCTGGCGCCCTGCTCCAGGAGCACCT

CCGAGAGCACAGCGGCCCTGGGCTGCCTGGTCAAGGACTACTTCCCCGAACCGG

TGACGGTGTCGTGGAACTCAGGCGCCCTGACCAGCGGCGTGCACACCTTCCCGG

CTGTCCTACAGTCCTCAGGACTCTACTCCCTCAGCAGCGTGGTGACCGTGCCCTC

CAGCAGCTTGGGCACCCAGACCTACATCTGCAACGTGAATCACAAGCCCAGCAA

CACCAAGGTGGACAAGAAAGTTGAGCCCAAATCTTGTGACAAAACTCACACATG

CCCACCGTGCCCAGCACCTGAAGCCGCGGGGGGACCGTCAGTCTTCCTCTTCCCC

CCAAAACCCAAGGACACCCTCATGATCTCCCGGACCCCTGAGGTCACATGCGTG

GTGGTGGACGTGAGCCACGAAGACCCTGAGGTCAAGTTCAACTGGTACGTGGAC

GGCGTGGAGGTGCATAATGCCAAGACAAAGCCGCGGGAGGAGCAGTACAACAG

CACGTACCGTGTGGTCAGCGTCCTCACCGTCCTGCACCAGGACTGGCTGAATGGC

AAGGAGTACAAGTGCAAGGTCTCCAACAAAGCCCTCCCAGCCCCCATCGAGAAA

ACCATCTCCAAAGCCAAAGGGCAGCCCCGAGAACCACAGGTGTACACCCTGCCC

CCATCCCGGGATGAGCTGACCAAGAACCAGGTCAGCCTGACCTGCCTGGTCAAA

GGCTTCTATCCCAGCGACATCGCCGTGGAGTGGGAGAGCAATGGGCAGCCGGAG

AACAACTACAAGACCACGCCTCCCGTGCTGGACTCCGACGGCTCCTTCTTCCTCT

ACAGCAAGCTCACCGTGGACAAGAGCAGGTGGCAGCAGGGGAACGTCTTCTCAT

GCTCCGTGATGCATGAGGCTCTGCACAACCACTACACGCAGAAGAGCCTCTCCCT

GTCTCCGGGTAAACTCGAGGACTACAAGGACGATGACGATAAGTGA

Mutant Human IgG1 Fc L234A/L235A mutation Protein (SEQ ID NO:2):
ASTKGPSVFPLAPCSRSTSESTAALGCLVKDYFPEPVTVSWNSGALTSGVHTFPAVLQ

SSGLYSLSSVVTVPSSSLGTQTYICNVNHKPSNTKVDKKVEPKSCDKTHTCPPCPAPE

AAGGPSVFLFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTISKAKGQPREP

QVYTLPPSRDELTKNQVSLTCLVKGFYPSDIAVEWESNGQPENNYKTTPPVLDSDGS

FFLYSKLTVDKSRWQQGNVFSCSVMHEALHNHYTQKSLSLSPGKLEDYKDDDDK* rAb58 Heavy Chain Sequence (Variable Region) Nucleic Acid (SEQ ID NO: 11):
GTGCAGCTGGTGGAGTCTGGGGGTGGCTTGGTTCAGCCGGGGGGGTCCCTGAGA

CTCTCCTGTGCAGCCTCTGGATTCACCTTTAGAGGTTATGCCATGAACTGGGTCC

GCCAGGCCCCAGGGAAGGGGCTGGAGTGGGTCGCAAGTATCAGTGGCAGTGGTA

GTATCACACAGTACGCAGACTCCGCGAAGGGCCGCTTCACCATCACCAGAGACA

ACTCCAAGAGCACGCTCTATGCGCATGTGAGTAGCCTGAGAGCCGATGACACGG

CCGTATATTACTGTGCGAAAGGGGACTACGTCTTTGACTACGGGGACAGGGAA

CCCTGGTCACCGTCTCCTCA rAb58 Heavy Chain Sequence (Variable Region) Protein (SEQ ID NO: 12):
VQLVESGGGLVQPGGSLRLSCAASGFTFRGYAMNWVRQAPGKGLEWVASISGSGSI

TQYADSAKGRFTITRDNSKSTLYAHVSSLRADDTAVYYCAKGDYVFDYWGQGTLV

TVSS rAb58 Light Chain Sequence (Variable Region + IgK Constant Region) Nucleic Acid (SEQ ID NO: 9):
GACATCCAGATGACCCAGTCTCCATCCGCCCTGTCTGCATCTGTAGGAGACACAG

TCACCATCACTTGCCGGGCCAGTCAGAGTATTAGGAGCTGGTTGGCCTGGTATCA

GCAGAAACCAGGGAAAGCCCCTAAACTCCTGATCTATAAGGCGTCTGATTTACA

AAGTGGGGTCCCATCAAGATTCAGCGGCAGTGGATCTGGGACAGACTTCACTCTC

ACCATCAGCGGCCTGCAGCCTGATGATTTTGCAACTTATTACTGCCAACACTATA

ATAGTTACCCGTACACTTTTGGCCAGGGGACCAAGGTGGAGATCAGACGAACTG

TGGCTGCACCATCTGTCTTCATCTTCCCGCCATCTGATGAGCAGTTGAAATCTGG

AACTGCCTCTGTTGTGTGCCTGCTGAATAACTTCTATCCCAGAGAGGCCAAAGTA

CAGTGGAAGGTGGATAACGCCCTCCAATCGGGTAACTCCCAGGAGAGTGTCACA

GAGCAGGACAGCAAGGACAGCACCTACAGCCTCAGCAGCACCCTGACGCTGAGC

AAAGCAGACTACGAGAAACACAAAGTCTACGCCTGCGAAGTCACCCATCAGGGC

CTGAGTTCGCCCGTCACAAAGAGCTTCAACAGGGGAGAGTGT rAb58 Light Chain Sequence (Variable Region + IgK Constant Region) Protein (SEQ ID NO: 10):
DIQMTQSPSALSASVGDTVTITCRASQSIRSWLAWYQQKPGKAPKLLIYKASDLQSG

VPSRFSGSGSGTDFTLTISGLQPDDFATYYCQHYNSYPYTFGQGTKVEIRRTVAAPSV

FIFPPSDEQLKSGTASVVCLLNNFYPREAKVQWKVDNALQSGNSQESVTEQDSKDST

YSLSSTLTLSKADYEKHKVYACEVTHQGLSSPVTKSFNRGEC

Mutant Human IgG1 Fc L234A/L235A/G237A mutation Nucleic Acid (SEQ ID NO: 14):
GCCTCCACCAAGGGCCCATCGGTCTTCCCCCTGGCGCCCTGCTCCAGGAGCACCT

CCGAGAGCACAGCGGCCCTGGGCTGCCTGGTCAAGGACTACTTCCCCGAACCGG

-continued

```
TGACGGTGTCGTGGAACTCAGGCGCCCTGACCAGCGGCGTGCACACCTTCCCGG

CTGTCCTACAGTCCTCAGGACTCTACTCCCTCAGCAGCGTGGTGACCGTGCCCTC

CAGCAGCTTGGGCACCCAGACCTACATCTGCAACGTGAATCACAAGCCCAGCAA

CACCAAGGTGGACAAGAAAGTTGAGCCCAAATCTTGTGACAAAACTCACACATG

CCCACCGTGCCCAGCACCTGAAGCCGCGGGGGCACCGTCAGTCTTCCTCTTCCCC

CCAAAACCCAAGGACACCCTCATGATCTCCCGGACCCCTGAGGTCACATGCGTG

GTGGTGGACGTGAGCCACGAAGACCCTGAGGTCAAGTTCAACTGGTACGTGGAC

GGCGTGGAGGTGCATAATGCCAAGACAAAGCCGCGGGAGGAGCAGTACAACAG

CACGTACCGTGTGGTCAGCGTCCTCACCGTCCTGCACCAGGACTGGCTGAATGGC

AAGGAGTACAAGTGCAAGGTCTCCAACAAAGCCCTCCCAGCCCCCATCGAGAAA

ACCATCTCCAAAGCCAAAGGGCAGCCCCGAGAACCACAGGTGTACACCCTGCCC

CCATCCCGGGATGAGCTGACCAAGAACCAGGTCAGCCTGACCTGCCTGGTCAAA

GGCTTCTATCCCAGCGACATCGCCGTGGAGTGGGAGAGCAATGGGCAGCCGGAG

AACAACTACAAGACCACGCCTCCCGTGCTGGACTCCGACGGCTCCTTCTTCCTCT

ACAGCAAGCTCACCGTGGACAAGAGCAGGTGGCAGCAGGGGAACGTCTTCTCAT

GCTCCGTGATGCATGAGGCTCTGCACAACCACTACACGCAGAAGAGCCTCTCCCT

GTCTCCGGGTAAACTCGAGGACTACAAGGACGATGACGATAAGTGA
```

Mutant Human IgG1 Fc L234A/L235A/G237A mutation Protein (SEQ ID NO: 15):
ASTKGPSVFPLAPCSRSTSESTAALGCLVKDYFPEPVTVSWNSGALTSGVHTFPAVLQ

SSGLYSLSSVVTVPSSSLGTQTYICNVNHKPSNTKVDKKVEPKSCDKTHTCPPCPAPE

<u>AAGA</u>PSVFLFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTISKAKGQPREP

QVYTLPPSRDELTKNQVSLTCLVKGFYPSDIAVEWESNGQPENNYKTTPPVLDSDGS

FFLYSKLTVDKSRWQQGNVFSCSVMHEALHNHYTQKSLSLSPGKLEDYKDDDDK* rAb09-3-33 Heavy Chain Sequence (Variable Region) Protein (SEQ ID NO: 17):
VTTGVHSEVQLVESGGGVVQPGGSLRLSCTASGFNLDDYDIHWVRQAPGKGLQWV

AILQPEESHQDYINSVRGRFSVSRDSSRDTIDLQMHSLRPEDTAIYYCTRSPGLMTTLR

GMVTRRHFHYFTMDVWGKGTTVIVSS rAb09-3-33 Heavy Chain Sequence (Variable Region) Nucleic Acid
(SEQ ID NO: 18):
GTAACTACAGGTGTCCACTCCGAGGTGCAGCTGGTGGAGTCTGGGGGAGGCGTG

GTCCAGCCTGGGGGGTCCCTAAGACTCTCCTGTACAGCGTCTGGTTTCAACTTAG

ATGACTATGACATTCACTGGGTCCGCCAGGCGCCCGGCAAGGGGCTGCAGTGGG

TGGCAATTTTGCAGCCTGAAGAAAGTCATCAAGACTATATAAATTCCGTGAGGG

GCCGATTCTCCGTCTCCAGAGACAGTTCGAGGGACACAATAGATCTGCAAATGC

ACAGTCTTAGACCTGAAGACACGGCTATATATTACTGTACGCGATCTCCGGGCCT

CATGACTACGCTGCGGGAATGGTGACCAGGAGGCACTTTCACTACTTCACCATG

GACGTCTGGGGCAAAGGGACCACGGTCATCGTCTCCTCA rAb09-3-33 Light Chain Sequence (Variable Region + IgK Constant Region)
Protein (SEQ ID NO: 19):
VLGLLLLWLTDARCDIVMTQSPLSLPVTPGEPASISCRSSQSLRHTITGYNYINWYLQ

KPGQSPQLLIFLASSRATGVPDRFSGSGAGTDFTLKISRVEAEDVGIYYCMQALHTPP

TFGQGTKLEIKR<u>TVAAPSVFIFPPSDEQLKS GTASVVCLLNNFYPREAKVQWKVDNA</u>

```
LQSGNSQESVTEQDSKDSTYSLSSTLTLSKADYEKHKLYACEVTHQGLSSPVTKSFN

RGEC rAb09-3-33 Light Chain Sequence (Variable Region + IgK Constant Region)
Nucleic Acid (SEQ ID NO: 20):
GTCCTGGGGTTGCTGCTGCTGTGGCTTACAGATGCCAGATGTGATATTGTGATGA

CTCAGTCTCCACTCTCCCTGCCCGTCACCCCTGGAGAGCCGGCCTCTATCTCCTGC

AGGTCTAGTCAGAGCCTCCGCCACACCATCACTGGATACAACTATATCAATTGGT

ACCTGCAGAAGCCAGGGCAGTCTCCACAACTCCTGATCTTTTTGGCCTCTTCTCG

GGCCACCGGGGTCCCTGACAGGTTCAGTGGCAGTGGAGCAGGCACAGATTTTAC

ACTGAAAATCAGCAGAGTGGAGGCTGAGGATGTTGGAATTTATTACTGCATGCA

AGCTCTACACACTCCGCCCACTTTTGGCCAGGGGACCAAACTGGAGATCAAACG

AACTGTGGCTGCACCATCTGTCTTCATCTTCCCGCCATCTGATGAGCAGTTGAAA

TCTGGAACTGCCTCTGTTGTGTGCCTGCTGAATAACTTCTATCCCAGAGAGGCCA

AAGTACAGTGGAAGGTGGATAACGCCCTCCAATCGGGTAACTCCCAGGAGAGTG

TCACAGAGCAGGACAGCAAGGACAGCACCTACAGCCTCAGCAGCACCCTGACGC

TGAGCAAAGCAGACTACGAGAAACACAAACTCTACGCCTGCGAAGTCACCCATC

AGGGCCTGAGTTCGCCCGTCACAAAGAGCTTCAACAGGGGAGAGTGTTAA
```

Furthermore, the antibodies sequences may vary from the sequences provided above, optionally using methods discussed in greater detail below. For example, nucleic acid sequences may vary from those set out above in that (a) the variable regions may be segregated away from the constant domains of the light chains, (b) the nucleic acids may vary from those set out above while not affecting the residues encoded thereby, (c) the nucleic acids may vary from those set out above by a given percentage, e.g., 70%, 75%, 80%, 85%, 90%, 91%, 92%, 93%, 94%, 95%, 96%, 97%, 98% or 99% homology, (d) the nucleic acids may vary from those set out above by virtue of the ability to hybridize under high stringency conditions, e.g., 65° C., 50% formamide, 0.1× SSC, 0.1% SDS, (e) the amino acids may vary from those set out above by a given percentage, e.g., 80%, 85%, 90%, 91%, 92%, 93%, 94%, 95%, 96%, 97%, 98% or 99% homology, or (f) the amino acids may vary from those set out above by permitting conservative substitutions (discussed below).

C. Engineering of Antibody Sequences

In various embodiments, one may choose to engineer sequences of the identified antibodies for a variety of reasons, such as improved expression, improved cross-reactivity, diminished off-target binding or abrogation of one or more natural effector functions, such as activation of complement or recruitment of immune cells (e.g., T cells, monocytes or NK cells). The following is a general discussion of relevant techniques for antibody engineering.

Hybridomas may cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy vector, then sequenced by automated DNA sequencing using standard vector primers. Assay of binding and neutralization may be performed using antibodies collected from hybridoma supernatants and purified by FPLC, using Protein G columns.

Recombinant full length IgG antibodies may be generated by subcloning heavy and light chain Fv DNAs from the cloning vector into a Lonza pConIgG1 or pConK2 plasmid vector, transfected into 293 Freestyle cells or Lonza CHO cells, and antibodies were collected an purified from the CHO cell supernatant. Other methods are described in Bennett et al. (2009).

The rapid availability of antibody produced in the same host cell and cell culture process as the final cGMP manufacturing process has the potential to reduce the duration of process development programs. Lonza has developed a generic method using pooled transfectants grown in CDACF medium, for the rapid production of small quantities (up to 50 g) of antibodies in CHO cells. Although slightly slower than a true transient system, the advantages include a higher product concentration and use of the same host and process as the production cell line. Example of growth and productivity of GS-CHO pools, expressing a model antibody, in a disposable bioreactor: in a disposable bag bioreactor culture (5 L working volume) operated in fed-batch mode, a harvest antibody concentration of 2 g/L was achieved within 9 weeks of transfection.

pCon Vectors™ are an easy way to re-express whole antibodies. The constant region vectors are a set of vectors offering a range of immunoglobulin constant region vectors cloned into the pEE vectors. These vectors offer easy construction of full length antibodies with human constant regions and the convenience of the GS System™.

Antibody molecules will comprise fragments (such as F(ab'), F(ab')$_2$) that are produced, for example, by the proteolytic cleavage of the mAbs, or single-chain immunoglobulins producible, for example, via recombinant means. Such antibody derivatives are monovalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

It may be desirable to "humanize" antibodies produced in non-human hosts in order to attenuate any immune reaction when used in human therapy. Such humanized antibodies may be studied in an in vitro or an in vivo context. Humanized antibodies may be produced, for example by replacing an immunogenic portion of an antibody with a corresponding, but non-immunogenic portion (i.e., chimeric antibodies). PCT Application PCT/US86/02269; EP Application 184,187; EP Application 171,496; EP Application 173,494; PCT Application WO 86/01533; EP Application 125,023; Sun et al. (1987); Wood et al. (1985); and Shaw et al. (1988); all of which references are incorporated herein by reference. General reviews of "humanized" chimeric antibodies are provided by Morrison (1985); also incorporated herein by reference. "Humanized" antibodies can alternatively be produced by CDR or CEA substitution. Jones et al. (1986); Verhoeyen et al. (1988); Beidler et al. (1988); all of which are incorporated herein by reference.

In related embodiments, the antibody is a derivative of the disclosed antibodies, e.g., an antibody comprising the CDR sequences identical to those in the disclosed antibodies (e.g., a chimeric, humanized or CDR-grafted antibody). In yet a further embodiment, the antibody is a fully human recombinant antibody.

Alternatively, one may wish to make modifications, such as introducing conservative changes into an antibody molecule. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (−0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (−0.4), sulfur containing amino acids: cysteine (−1.0) and methionine (−1.3); hydrophobic, nonaromatic amino acids: valine (−1.5), leucine (−1.8), isoleucine (−1.8), proline (−0.5±1), alanine (−0.5), and glycine (0); hydrophobic, aromatic amino acids: tryptophan (−3.4), phenylalanine (−2.5), and tyrosine (−2.3).

It is understood that an amino acid can be substituted for another having a similar hydrophilicity and produce a biologically or immunologically modified protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

The present invention also contemplates isotype modification. By modifying the Fc region to have a different isotype, different functionalities can be achieved. For example, changing to $IgG_4$ can reduce immune effector functions associated with other isotypes.

Modified antibodies may be made by any technique known to those of skill in the art, including expression through standard molecular biological techniques, or the chemical synthesis of polypeptides. Methods for recombinant expression are addressed elsewhere in this document.

D. Chemical Modifications

Another approach to impairing IgG function in the Fc region is to carbamylate, amidate or benzylate the antibodies. Techniques for these modifications are presented in Thrasher and Cohen, *J. Immunol.*, 107:672-677 (1971).

E. Single Chain Antibodies

A Single Chain Variable Fragment (scFv) is a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide. Alternatively, scFv can be created directly from subcloned heavy and light chains derived from a hybridoma. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alaine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. $5 \times 10^6$ different members) was displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the $V_H$ C terminus and an abundance of arginines and prolines at other positions as the only common features of the selected tethers.

The recombinant antibodies of the present invention may also involve sequences or moieties that permit dimerization or multimerization of the receptors. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stabilizing and coagulating agent. However, it is contemplated that dimers or multimers of the same analog or heteromeric complexes comprised of different analogs can be created. To link two different compounds in a step-wise manner, hetero-bifunctional cross-linkers can be used that eliminate unwanted homopolymer formation.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

F. Purification

In certain embodiments, the antibodies of the present invention may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present invention, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens my be used to simultaneously purify and select appropriate antibodies. Such methods often utilize the selection agent bound to a support, such as a column, filter or bead. The antibodies is bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

III. Treatment or Prevention of NMO

A. Formulation and Administration The present invention provides pharmaceutical compositions comprising anti-AQP4 antibodies and antigens for generating the same. Such compositions comprise a prophylactically or therapeutically effective amount of an antibody or a fragment thereof, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a particular carrier when the pharmaceutical composition is administered intravenously. Saline solutions and aqueous dextrose and glycerol solutions can also be employed as liquid carriers, particularly for injectable solutions. Other suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc. Examples of suitable pharmaceutical agents are described in "Remington's Pharmaceutical Sciences." Such compositions will contain a prophylactically or therapeutically effective amount of the antibody or fragment thereof, preferably in purified form, together with a suitable amount of carrier so as to provide the form for proper administration to the patient. The formulation should suit the mode of administration, which can be oral, intravenous, intraarterial, intrabuccal, intranasal, nebulized, bronchial inhalation, or delivered by mechanical ventilation.

Passive transfer of antibodies, known as artificially acquired passive immunity, generally will involve the use of intravenous or intramuscular injections. The forms of antibody can be human or animal blood plasma or serum, as pooled human immunoglobulin for intravenous (IVIG) or intramuscular (IG) use, as high-titer human IVIG or IG from immunized or from donors recovering from disease, and as monoclonal antibodies (MAb). Such immunity generally lasts for only a short period of time, and there is also a potential risk for hypersensitivity reactions, and serum sickness, especially from gamma globulin of non-human origin. However, passive immunity provides immediate protection. The antibodies will be formulated in a carrier suitable for injection, i.e., sterile and syringeable.

Generally, the ingredients of compositions are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

B. Combination Therapy

In order to increase the effectiveness of the antibody therapy of the present invention, it may be desirable to combine this treatment with other agents effective at treating or preventing NMO. This process may involve administering to the patient the antibody of the present invention the other agent(s) at the same time. This may be achieved by use of a single pharmaceutical composition that includes both agents, or by administering two distinct compositions at the same time, wherein one composition includes the antibody of the present invention and the other includes the second agent(s).

The two therapies may be given in either order and may precede or follow the other treatment by intervals ranging from minutes to weeks. In embodiments where the other agents are applied separately, one would generally ensure that a significant period of time did not expire between the time of each delivery, such that the agents would still be able to exert an advantageously combined effect on the patient. In such instances, it is contemplated that one may administer both modalities within about 12-24 h of each other and, more preferably, within about 6-12 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

Various combinations may be employed, the antibody treatment of the present invention is "A" and the secondary treatment is "B":

A/B/A B/A/B B/B/A A/A/B A/B/B B/A/A A/B/B/B

B/A/B/B B/B/B/A B/B/A/B A/A/B/B A/B/A/B A/B/B/A

B/B/A/A B/A/B/A B/A/A/B A/A/A/B B/A/A/A A/B/A/A

A/A/B/A

Administration of the secondary agent will follow general protocols for that drug, taking into account the toxicity, if any. It is expected that the treatment cycles would be repeated as necessary. Secondary treatments are discussed below.

i. Immunosuppressive Agents

Corticosteroids (high dose for acute attacks; low dose for chronic therapy) such as prednisone are the main line therapy for NMO and thus are readily applied as a combined therapy with the anti-AQP4 antibodies of the present invention. Immunosuppressant treatments that can be used in combination with anti-AQP4 antibodies include azathioprine (Imuran) plus prednisone, mycophenolate mofetil plus prednisone, Rituximab, Mitoxantrone, intravenous immunoglobulin (WIG), and cyclophosphamide.

ii. Plasmapheresis

Plasmapheresis is the removal, treatment, and return of (components of) blood plasma from blood circulation. It is thus an extracorporeal therapy (a medical procedure which is performed outside the body). The method can also be used to collect plasma for further manufacturing into a variety of medications. The procedure is used to treat a variety of disorders, including those of the immune system, such as Myasthenia gravis, Guillain-Barré syndrome, lupus, thrombotic thrombocytopenic purpura and NMO. During plasmapheresis, blood is initially taken out of the body through a needle or previously implanted catheter. Plasma is then removed from the blood by a cell separator. Three procedures are commonly used to separate the plasma from the blood cells:

Discontinuous flow centrifugation: One venous catheter line is required. Typically, a 300 ml batch of blood is removed at a time and centrifuged to separate plasma from blood cells.

Continuous flow centrifugation: Two venous lines are used. This method requires slightly less blood volume to be out of the body at any one time as it is able to continuously spin out plasma.

Plasma filtration: Two venous lines are used. The plasma is filtered using standard hemodialysis equipment. This continuous process requires less than 100 ml of blood to be outside the body at one time.

Each method has its advantages and disadvantages. After plasma separation, the blood cells are returned to the person undergoing treatment, while the plasma, which contains the antibodies, is first treated and then returned to the patient in traditional plasmapheresis. (In plasma exchange, the removed plasma is discarded and the patient receives replacement donor plasma, albumin, or a combination of albumin and saline (usually 70% albumin and 30% saline). Rarely, other replacement fluids, such as hydroxyethyl starch, may be used in individuals who object to blood transfusion but these are rarely used due to severe side-effects. Medication to keep the blood from clotting (an anticoagulant) is given to the patient during the procedure.

An important use of plasmapheresis is in the therapy of autoimmune disorders, where the rapid removal of disease-causing autoantibodies from the circulation is required in addition to other medical therapy. It is important to note that plasma exchange therapy in and of itself is useful to temper the disease process, where simultaneous medical and immunosuppressive therapy is required for long-term management. Plasma exchange offers the quickest short-term answer to removing harmful autoantibodies; however, the production of autoantibodies by the immune system must also be suppressed, usually by the use of medications such as prednisone, cyclophosphamide, cyclosporine, mycophenolate mofetil, rituximab or a mixture of these.

IV. Antibody Conjugates

Antibodies may be linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., immunosuppression/anti-inflammation. Non-limiting examples of such molecules are set out above. Such molecules are optionally attached via cleavable linkers designed to allow the molecules to be released at or near the target site.

By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, photoaffinity molecules, colored particles or ligands, such as biotin.

Antibody conjugates are generally preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Many appropriate imaging agents are known in the art, as are methods for their attachment to antibodies (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNCl$_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugates contemplated are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds. The use of such labels is well known to those of skill in the art and are described, for example, in U.S. Pat. Nos. 3,817,837, 3,850,752, 3,939,350, 3,996,345, 4,277,437, 4,275,149 and 4,366,241.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. No. 4,472,509 and U.S. Pat. No. 4,938,948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

V. Immunodetection Methods

In still further embodiments, there are immunodetection methods for binding, purifying, removing, quantifying and otherwise generally detecting AQP4 and its associated antigens. Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. In particular, a competitive assay for the detection and quantitation of AQP4 antibodies also is provided. The steps of various useful immunodetection methods have been described in the scientific literature, such as, e.g., Doolittle and Ben-Zeev (1999), Gulbis and Galand (1993), De Jager et al. (1993), and Nakamura et al. (1987). In general, the immunobinding methods include obtaining a sample and contacting the sample with a first antibody in accordance with embodiments discussed herein, as the case may be, under conditions effective to allow the formation of immunocomplexes.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to AQP4 present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

1. ELISAs

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the invention are immobilized onto a selected surface exhibiting protein affinity, such as a well in a polystyrene microtiter plate. Then, a test composition suspected of containing the AQP4 is added to the wells. After binding and washing to remove non-specifically bound immune complexes, the bound antigen may be detected. Detection may be achieved by the addition of another anti-AQP4 antibody that is linked to a detectable label. This type of ELISA is a simple "sandwich ELISA." Detection may also be achieved by the addition of a second anti-AQP4 antibody, followed by the addition of a third antibody that has binding affinity for the second antibody, with the third antibody being linked to a detectable label.

In another exemplary ELISA, the samples suspected of containing the AQP4 antigen are immobilized onto the well surface and then contacted with anti-AQP4 antibody. After binding and washing to remove non-specifically bound immune complexes, the bound anti-AQP4 antibodies are detected. Where the initial anti-AQP4 antibodies are linked to a detectable label, the immune complexes may be detected directly. Again, the immune complexes may be detected using a second antibody that has binding affinity for the first anti-AQP4 antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

2. Western Blot

The Western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that bacteria, virus or environmental samples can be the source of protein and thus Western blotting is not restricted to cellular studies only. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF, but are far more fragile and do not stand up well to repeated probings. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

3. Immunohistochemistry

The antibodies may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

4. Immunodetection Kits

In still further embodiments, there are immunodetection kits for use with the immunodetection methods described above. The immunodetection kits will thus comprise, in suitable container means, a first antibody that binds to AQP4 antigen, and optionally an immunodetection reagent.

In certain embodiments, the AQP4 antibody may be pre-bound to a solid support, such as a column matrix and/or well of a microtitre plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with embodiments discussed herein.

The kits may further comprise a suitably aliquoted composition of the AQP4 antigen, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits will also include a means for containing the antibody, antigen, and any other reagent containers in close confinement for commercial sale. Such containers may include injection or blow-molded plastic containers into which the desired vials are retained.

VI. Examples

The following examples are included to demonstrate preferred embodiments. It should be appreciated by those of skill in the art that the techniques disclosed in the examples which follow represent techniques discovered by the inventors to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Materials and Methods

DNA Constructs, Cell Culture and Transfections.

DNA constructs encoding full-length human AQP4 (M1 and M23 isoforms) were generated by PCR-amplification using whole brain cDNA as template. For some studies a Myc epitope (NH$_2$-EQKLISEEDL-COOH; SEQ ID NO:13) was inserted in the second extracellular loop by PCR-amplification using the non-tagged constructs as template. Mutants of M1 and M23 were generated by PCR-amplification using either tagged or non-tagged templates. All PCR fragments were ligated into mammalian expression vector pcDNA3.1 and fully sequenced.

U87MG cell cultures (ATCC HTB-14) were maintained at 37° C. in 5% CO$_2$/95% air in EMEM medium containing 10% fetal bovine serum, 100 U/mL penicillin and 100 μg/mL streptomycin. Cells were grown on glass coverslips and transfected with DNA in antibiotic-free medium using Lipofectamine 2000 (Invitrogen, Carlsbad, Calif.) according to the manufacturer's protocol. Stable AQP4-expressing clones were selected following enrichment in Geneticin (Invitrogen) and plating in 96-well plates at very low density.

NMO Patient Sera and Recombinant AQP4 Autoantibodies.

NMO serum was obtained from four NMO-IgG seropositive individuals who met the revised diagnostic criteria for clinical disease (Wingerchuk et al., 2006). Control (non-NMO) human serum was purchased from the UCSF cell culture facility. Recombinant monoclonal NMO antibodies were generated from clonally-expanded cerebrospinal fluid plasma blasts as described previously (Bennett et al., 2009). Heavy- and light-chain constructs were co-transfected into HEK293 cells, the supernatant harvested, centrifuged to remove any cells and debris, and incubated overnight with protein A-Sepharose (Sigma-Aldrich, St. Louis, Mo.) at 4° C. The rAb was eluted in 0.1 M glycine/1 M NaCl (pH 3.0) and adjusted to pH 7.5 with 0.1 M Tris-HCl, pH 8.0. Recombinant IgG was subsequently exchanged and concentrated in PBS containing 0.1% protease-free bovine serum albumin using Ultracel YM-30 microconcentrators (Millipore, Billerica, Mass.). Fab fragments were generated by digestion of whole IgG with immobilized papain, and purified by removal of undigested IgG and Fc fragments by protein-A (Thermo Fisher Scientific, Rockford, Ill.). Antibody integrity was confirmed by denaturing and native gel electrophoresis, and IgG concentration was assayed using a human IgG-capture ELISA.

Quantitative Immunofluorescence.

AQP4-expressing U87MG cells were incubated for 20 min in live-cell blocking buffer (PBS containing 6 mM glucose, 1 mM pyruvate, 1% bovine serum albumin, 2% goat serum), and then for 30 min with NMO patient serum or recombinant NMO-IgG in blocking buffer. Cells were then rinsed extensively with PBS, fixed in 4% paraformaldehyde for 15 min, and permeabilized with 0.1% Triton X-100. Cells were then blocked again and incubated for 30 min with 0.4 μg/mL polyclonal, C-terminal specific rabbit anti-AQP4 antibody (Santa Cruz Biotechnology, Santa Cruz, Calif.), then rinsed with PBS. Finally, cells were incubated for 30 min with 4 μg/mL goat anti-human IgG-conjugated Alexa Fluor 488 and goat anti-rabbit IgG-conjugated Alexa Fluor 555 (Invitrogen) in blocking buffer. After incubation with secondary antibodies, cells were rinsed extensively in PBS, and coverglasses were mounted with VectaMount hard-set medium (Vector Laboratories, Burlingame, Calif.). In some experiments, U87MG cells were labeled as described above, but with a monoclonal mouse anti-Myc IgG (Covance, Emeryville, Calif.) or purified Fab fragments instead of whole NMO-IgG. Anti-Myc was stained with goat anti-mouse IgG-conjugated Alexa Fluor 488 (Invitrogen), while Fab fragments were stained with Dylight 488-linked F(ab')$_2$-specific secondary antibodies (Jackson Immunoresearch, West Grove, Pa.). Quantitative analysis of AQP4-antibody binding was done on a Nikon Eclipse TE2000S inverted epifluorescence microscope (Nikon, Melville, N.Y.) equipped with a Nikon 10× air objective (numerical aperture 0.3). Green and red dyes were excited and observed through Chroma filter sets #41001 and #42001 (Chroma, Rockingham, Vt.), respectively. Images were recorded by a CCD camera (Hamamatsu Orca, Bridgewater, N.J.), and intensities determined using custom software.

Total Internal Reflection Fluorescence Microscopy.

TIRFM was done using a Nikon Eclipse TE2000E microscope with a through-objective TIRF attachment and a 100×TIRF oil immersion objective (numerical aperture 1.49) mounted on a perfect focus module (Nikon). Alexa Fluor 555-labeled AQP4 was excited using an argon-ion laser through a Z514/10× excitation filter and Z514RDC dichroic mirror, and detected through an ET605/40 m emission filter (Chroma). Images were acquired using a QuantEM 512SC deep-cooled CCD camera (Photometrics, Tucson, Ariz.).

Single Particle Tracking.

Prior to labeling of AQP4 with quantum dots (Qdots), cells expressing Myc-tagged AQP4 were washed with 2 mL PBS containing 6 mM glucose and 1 mM pyruvate (GP buffer) and incubated for 5 min in blocking buffer. Cells were then incubated for 5 min with 70 ng/mL mouse anti-Myc antibody (Covance) in blocking buffer, rinsed, and incubated for 5 min with 0.1 nM goat F(ab')$_2$ anti-mouse IgG-conjugated Qdot 655 (Invitrogen) in blocking buffer. Cells were rinsed extensively and maintained throughout experiments in GP buffer. SPT was performed on a Nikon Eclipse TE2000S inverted epifluorescence microscope equipped with a Nikon 100×TIRF oil immersion objective (numerical aperture 1.45) and a deep-cooled CCD camera (Hamamatsu EM-CCD, Bridgewater, N.J.). Qdot fluorescence was excited using an E460SPUV excitation filter and 475DCXRU dichroic mirror, and detected through a D655/40m emission filter (Chroma). Data were acquired continuously at 11 ms per frame (91 Hz) for 6 s. Image sequences were analyzed and trajectories constructed as described in detail previously (Crane and Verkman, 2008). Diffusion data are reported in the form of cumulative distributions of ranges at 1 s, where P(range) is defined as the probability that a particle's range is less than or equal to a given distance at t=1 s.

Electrophoresis and Immunoblotting.

Cell cultures were lysed with NativePAGE sample buffer (Invitrogen) containing 0.5% dodecyl-β-D-maltoside (EMD chemicals, Gibbstown, N.J.) for 10 min on ice. Lysates were centrifuged at 20,000 g for 30 min at 4° C. and the pellet discarded. For Blue-Native gel electrophoresis (BN-PAGE), polyacrylamide native gradient gels (3-9%) were prepared as previously described (Wittig et al., 2006). 10 µg of protein was mixed with 5% Coomassie Blue G-250 (Invitrogen) and loaded in each lane. Ferritin was used as the molecular mass standard (440 and 880 kDa). Running buffers were: 25 mM imidazole, pH 7 (anode buffer) and 50 mM Tricine, 7.5 mM imidazole, 0.02% Coomassie Blue G-250, pH 7 (cathode buffer). Tricine SDS-PAGE was performed as previously described (Schagger and Tricine, 2006) with a 12% running gel and 3% stacking gel. Samples were not heated prior to loading. SeeBlue Plus2 Pre-Stained Standard (Invitrogen) was used as a molecular weight marker. Proteins were blotted onto polyvinyl difluoride membranes (Bio-Rad, Hercules, Calif.). For immunoblot analysis, membranes were blocked with 3% BSA and incubated with rabbit anti-AQP4 primary antibodies (Santa Cruz) for 2 h. Membranes were then rinsed and incubated for 1 h with horseradish peroxidase-conjugated goat anti-rabbit IgG (Jackson ImmunoResearch), rinsed extensively, and labeled proteins were detected using the ECL Plus enzymatic chemiluminescence kit (Amersham Biosciences, Pittsburgh, Pa.).

Example 2—Results

Approach for Quantitative Analysis of NMO-IgG Binding to AQP4.

Figure 1A:
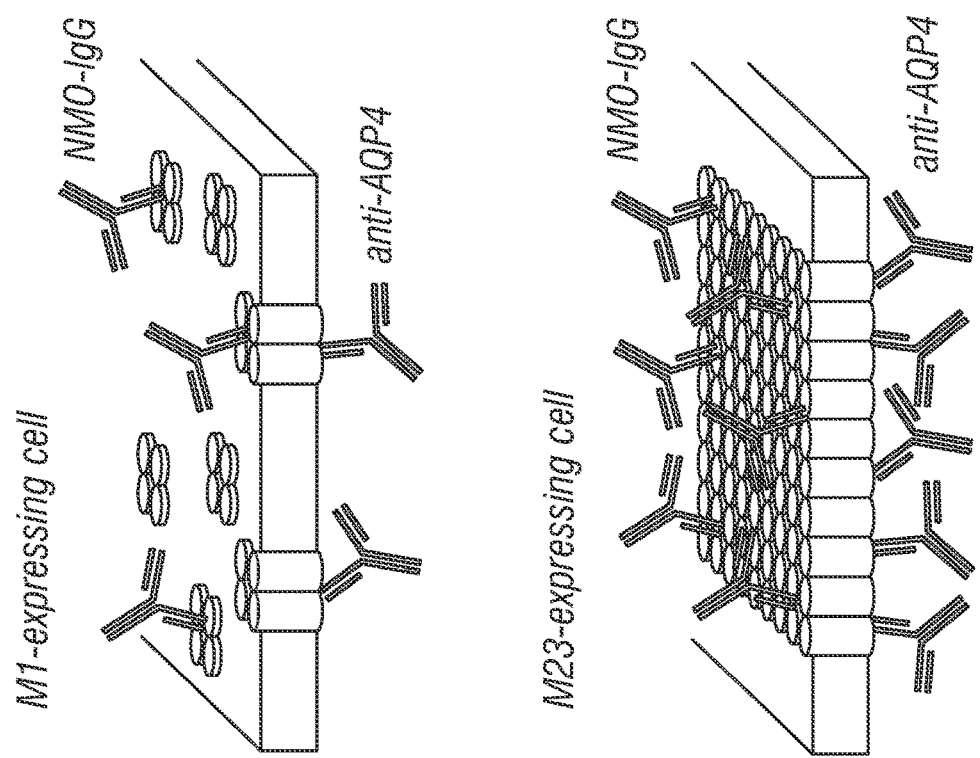

FIG. 1 diagrams the approach used for quantitative analysis of NMO-IgG binding to AQP4. Cells expressing specified AQP4 isoform(s) at their plasma membrane were incubated with NMO-IgG (NMO patient serum or recombinant monoclonal antibody), fixed, permeabilized, and then incubated with anti-AQP4 antibody (FIG. 1A). The anti-AQP4 antibody recognizes the AQP4 C-terminus, which is common to all AQP4 isoforms (FIG. 1B). Fluorescent secondary antibodies were used to detect NMO-IgG by green fluorescence and AQP4 by red fluorescence. NMO-IgG binding to AQP4 was quantified by green-to-red (G/R) fluorescence ratio. Binding affinity and stoichometry was determined by titration with increasing NMO-IgG concentration. In contrast to measurements done at a single NMO-IgG concentration, measurement of full, concentration-dependent binding provides a quantitative, unbiased description of NMO-IgG binding to AQP4.

Figure 2A:
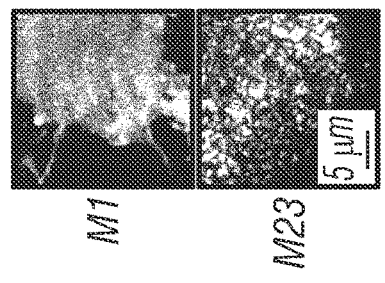
FIGS. 2A-D. Characterization of stably transfected, AQP4-expressing U87MG cells.
Figure 2B:
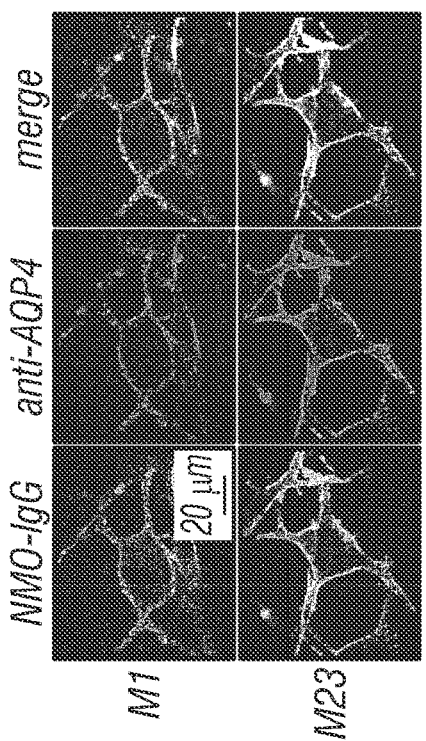
Figure 2C:
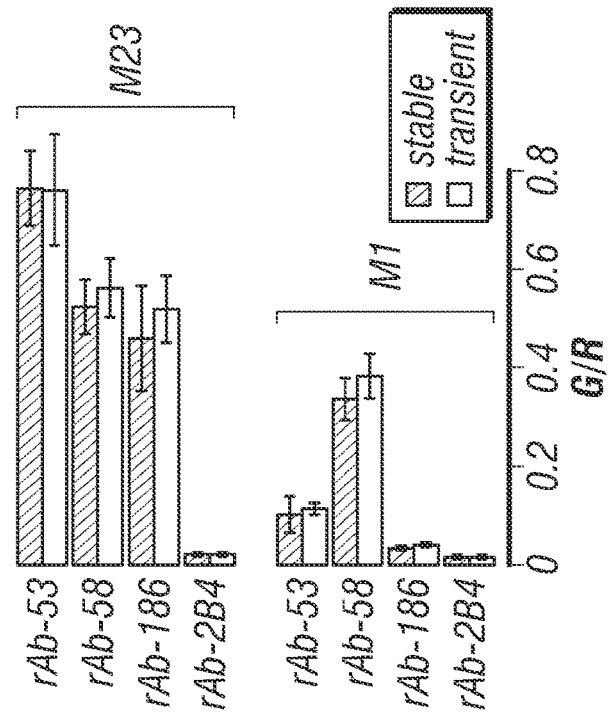
Figure 2D:
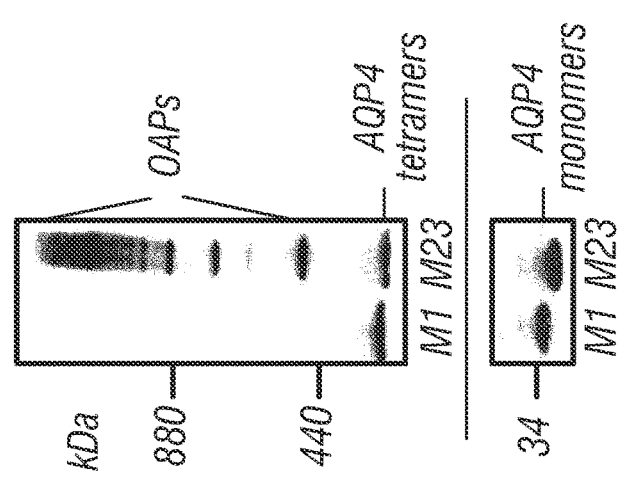

A cell line for analysis of NMO-IgG binding to AQP4 was selected that showed efficient plasma membrane targeting of AQP4 isoforms following stable or transient transfections, as well as human glial cell origin, rapid growth, and strong adherence to coverglass supports. The selected cell line, U87MG, was originally derived from a human astrocytoma (Ponten and Macintyre, 1968). FIG. 2A shows high-magnification confocal microscopy of U87MG cells stably expressing M1 or M23 AQP4, and stained with a recombinant monoclonal NMO-IgG (green) and an anti-AQP4 antibody (red). AQP4 was localized to the cell plasma membrane, with little intracellular red fluorescence. FIG. 2B shows TIRFM of the anti-AQP4 antibody-stained AQP4-expressing cells. A smooth pattern of fluorescence was seen for M1-AQP4 and a punctate pattern for M23-AQP4, as found in other cell types (Crane et al., 2008), confirming that M23-AQP4 forms OAPs in transfected U87MG cells whereas M1-AQP4 does not. Immunoblot analysis of cell homogenates showed the expected molecular sizes of the M1 and M23 isoforms of AQP4 (FIG. 2C, bottom). BN-PAGE of cells expressing M23 alone showed multiple high molecular weight bands corresponding to the expected formation of large supramolecular aggregates (OAPs), whereas M1-expressing cells showed only the expected ~300 kDa band corresponding to individual AQP4 tetramers (FIG. 2C, top). FIG. 2D shows examples of measured green-to-red ratios (G/R) after binding recombinant monoclonal NMO-IgGs (rAb-53, rAb-58, and rAb-186) or control antibody (rAb-2B4) (each at 20 µg/mL) to M1 or M23 AQP4-expressing cells. These initial measurements show considerable diversity of NMO-IgG to M1 vs. M23 AQP4 isoforms, with similar results found in both stably and transiently transfected U87MG cells.

Heterogeneous NMO-IgG Binding to AQP4 Isoforms in NMO Serum Samples.

Binding of NMO-IgG in human NMO sera to the M1 and M23 AQP4 isoforms was measured by the fluorescence ratio imaging method. Initial measurements done on 10 serum specimens from NMO patients studied at a 1:100 dilution showed a wide range of relative M1:M23 binding from 0.14 to 0.67. FIG. 3A shows representative fluorescence micrographs for serum specimens from four NMO patients. Each serum specimen showed strong NMO-IgG binding to M23 AQP4, but variable binding to M1 AQP4. FIG. 3B shows concentration-dependent NMO-IgG binding in which background-corrected R/G ratios were determined as a function of serum concentration. NMO-IgG binding to AQP4 was saturable, with relative M23:M1 binding affinities of 0.11 (serum 1), 0.26 (serum 2), 0.03 (serum 3) and 0.21 (serum 4). Interestingly, the binding data fitted well to a single-site, saturable binding model with near unity Hill coefficient, despite the presumed polyclonal composition of NMO serum. It is not possible to determine absolute binding affinity of NMO-IgG to AQP4 using serum because the fraction of NMO-IgG in total serum IgG is not known, nor is the polyclonal NMO-IgG composition.

Quantitative Binding of Recombinant Monoclonal NMO-IgGs to AQP4 Isoforms.

Figure 4A:
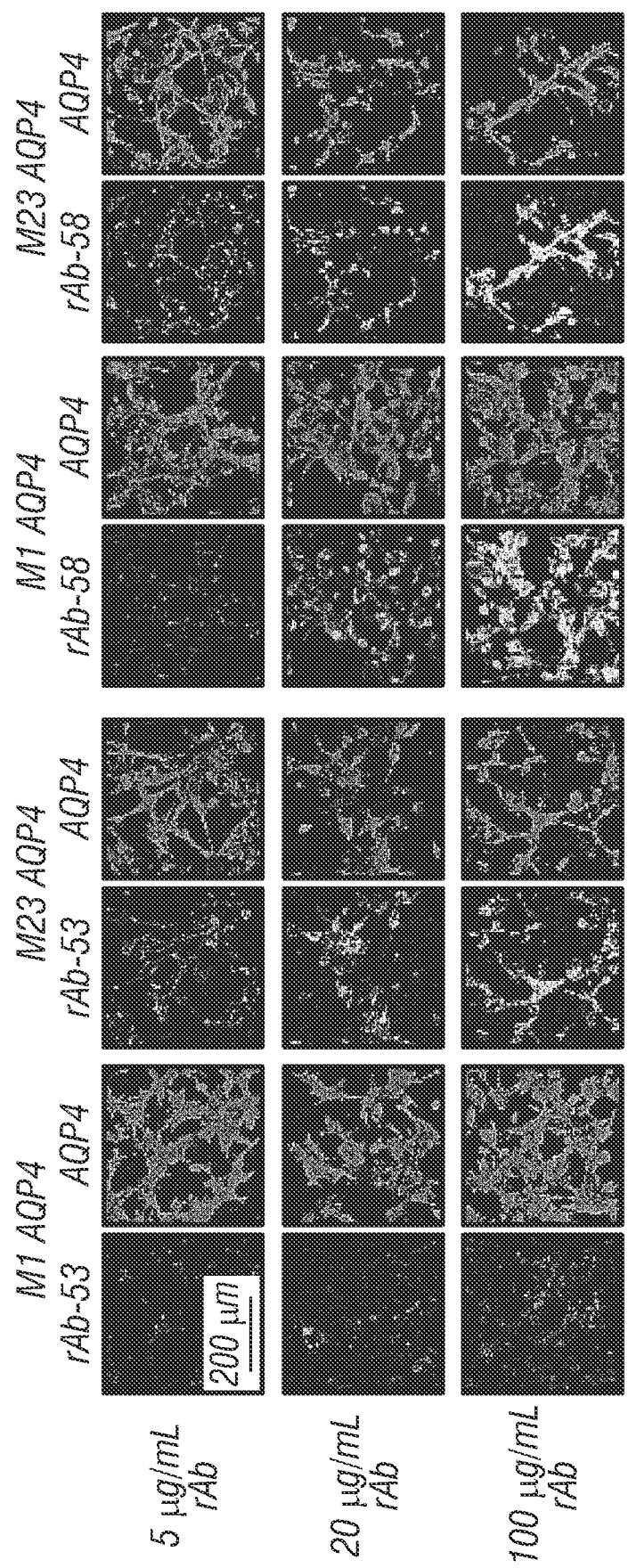
FIGS. 4A-B. Differential binding of purified monoclonal NMO-IgGs to M1 vs. M23 AQP4.
Figure 4B:
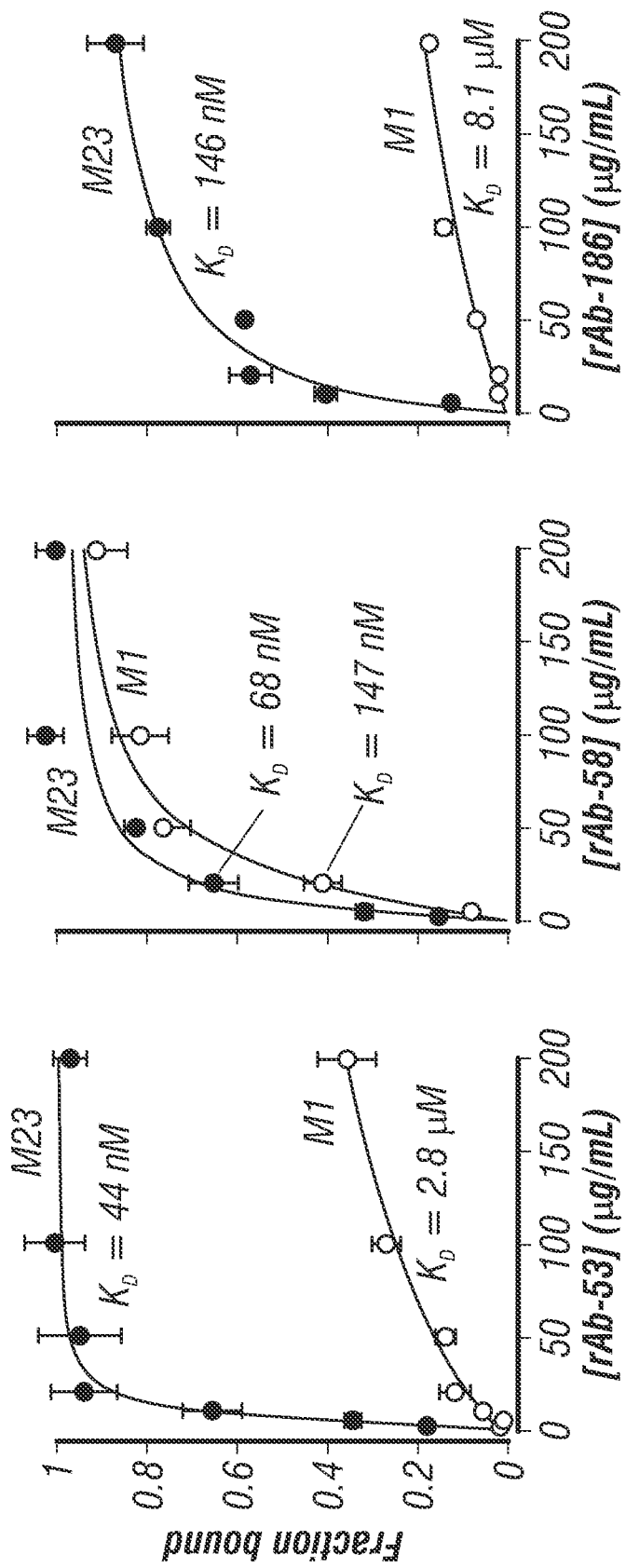

NMO-IgG in serum from a single NMO patient is polyclonal, consisting of a pool of monoclonal NMO-IgGs. A similar binding analysis was done using monoclonal recombinant NMO-IgGs derived from a single NMO patient in order to determine: (i) absolute binding affinities; (ii) whether differential M23:M1 is heterogeneous in a single NMO patient; and (iii) whether differential M23:M1 binding is due to differences in NMO-IgG binding affinity and/or stoichiometry. FIG. 4A shows fluorescence micrographs of two recombinant monoclonal NMO-IgGs (rAb-53 and rAb-58) from a single NMO patient. The monoclonal antibodies used in this study were derived from the CSF of a single NMO patient (corresponding to 'serum 1' in FIG. 3). Though strong monoclonal antibody binding to M23 AQP4 was seen in each case, binding to M1 AQP4 was variable. FIG. 4B summarizes concentration-dependence binding curves for three recombinant NMO-IgGs, together with curve fits for a single-site binding model. In each case the data fitted well to a single-site model with near unity Hill coefficient. The lowest dissociation constant was 44 nM, which was found for binding of rAb-53 to M23 AQP4. Marked heterogeneity was found for monoclonal NMO-IgGs from a single NMO patient, with relative M23:M1 binding affinities of 0.02 (rAb-53), 0.46 (rAb-58) and 0.02 (rAb-186). The binding curves in FIG. 4B also support the conclusion that differences in M23:M1 binding are due to differences in binding affinity rather than to binding capacity.

Mechanism of AQP4 Isoform-Specific Binding of NMO-IgG.

The inventors investigated whether differences in NMO-IgG binding affinity to M23 vs. M1 AQP4 are due to formation of OAPs by M23 AQP4 and/or to the different N-termini of M23 vs. M1. Measurements were made of NMO-IgG binding to cells expressing: (i) different ratios of M23:M1 AQP4; (ii) an M1 mutant that has a diminished ability to disrupt OAPs when coexpressed with M23; and (iii) M23 AQP4 mutants that have diminished ability to form OAPs. For these studies, the inventors used transiently transfected U87MG cells. The suitability of transiently transfected cells was validated above by showing comparable binding in stably vs. transiently transfected cells by NMO-IgG at a fixed concentration (FIG. 2D).

Figure 5A:
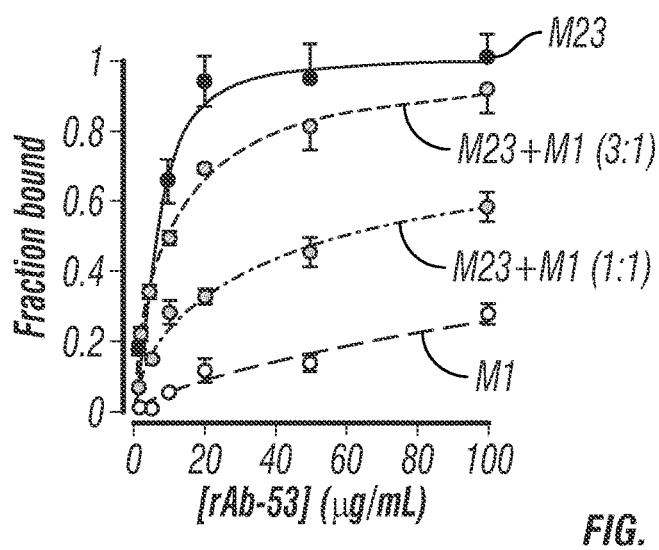
FIGS. 5A-C. Binding of NMO-IgG to mixtures of M1 and M23 AQP4, and to M23 mutants containing OAP-disrupting mutations.
Figure 5A:
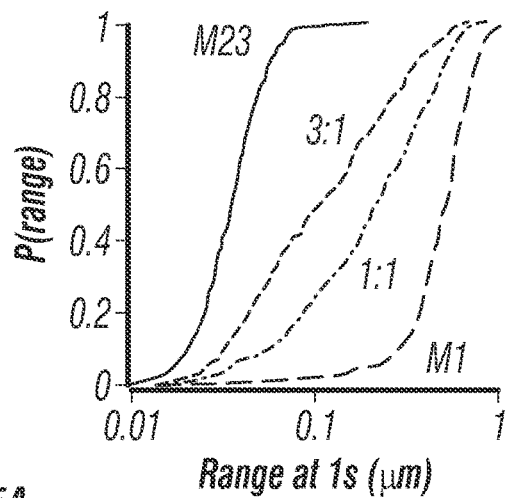

FIG. 5A shows concentration-dependent binding of NMO-IgG (rAb-53) to U87MG cells co-expressing different ratios of M23:M1 AQP4. The fraction of AQP4 in OAPs and average OAP size are directly related to the M23:M1 AQP4 ratio. Quantum dot single-particle tracking measurements were done to determine the characteristics of OAPs formed at different M23:M1 ratios. FIG. 5A (right) shows increased AQP4 diffusion with higher M1 content, as previously shown (Crane et al., 2009). This increase in AQP4 diffusion is due to active disruption of OAP growth by M1 AQP4. Not surprisingly, as compared to binding M23 alone, rAb-53 showed incrementally reduced AQP4 binding in 3:1 and 1:1 mixtures of M23:M1 (FIG. 5A, left).

Figure 5B:
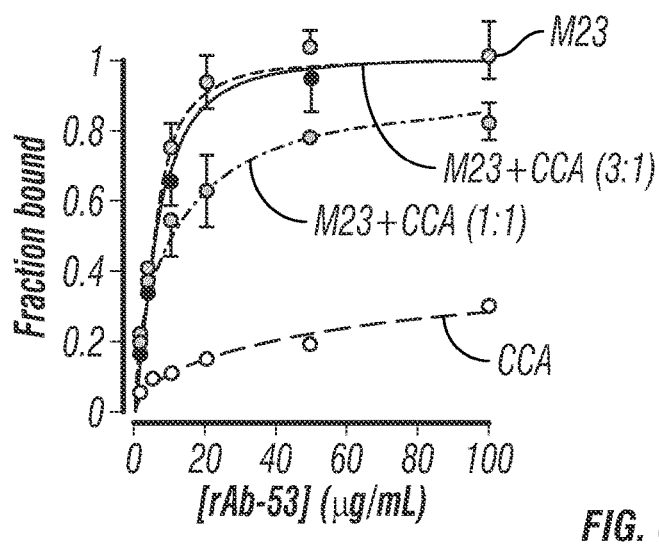
Figure 5B:
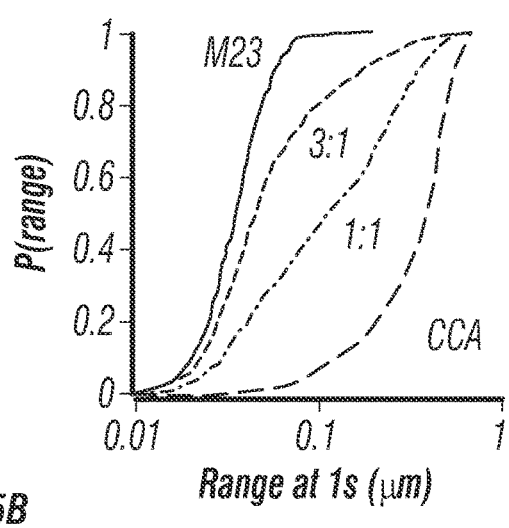

FIG. 5B shows data from similar experiments as in FIG. 5A, except that native M1 was substituted by the double-cysteine mutant M1-C13A/C17A (CCA). CCA AQP4 does not form OAPs on its own, but when co-expressed with M23 has greatly reduced ability to disrupt OAPs (Crane et al., 2009). Therefore, at the same M23:M1 ratio, cells expressing the CCA mutant in place of native M1 have greater OAP content, as confirmed by single particle tracking (FIG. 5B, right). Concentration-dependent binding of rAb-53 showed greater binding to M23:CCA mixtures than to M23:M1 mixtures (FIG. 5B, left). Binding of rAb-53 to cells expressing a 3:1 ratio of M23:CCA was identical to cells expressing M23 alone.

Figure 5C:
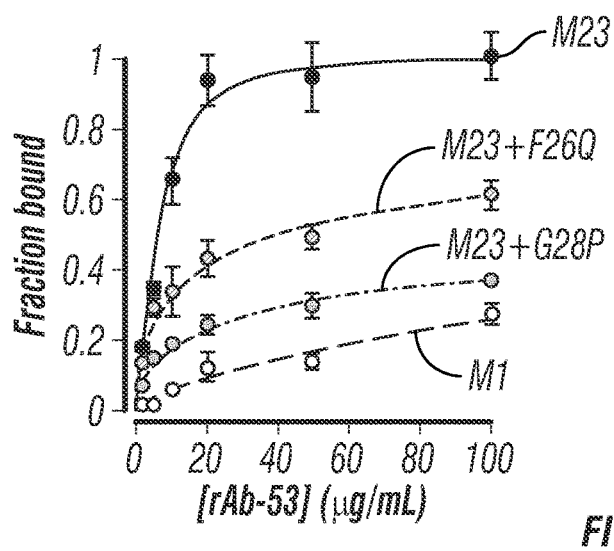
Figure 5C:
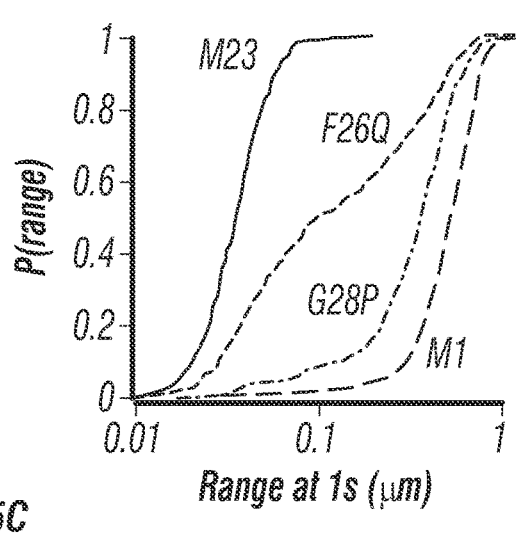

As an independent approach to address the binding specificity issue, the inventors measured NMO-IgG binding to U87MG cells expressing M23 mutants containing an OAP-disrupting point mutation. The OAP-disrupting effect of these mutations was confirmed by quantum dot single-particle tracking FIG. 5C (right) shows that mutations F26Q and G28P in the M23 AQP4 N-terminus greatly reduce OAP content, similar to the inventors' previous findings with corresponding rat isoforms of AQP4 (Crane and Verkman, 2009). FIG. 5C (left) shows greatly reduced concentration-dependent binding of rAb-53 to cells expressing these M23 mutants when compared to native M23. Together, the results in FIGS. 5A-C indicate that OAP formation is responsible for the increased affinity of NMO-IgG to M23 vs. M1 AQP4.

Figure 6A:
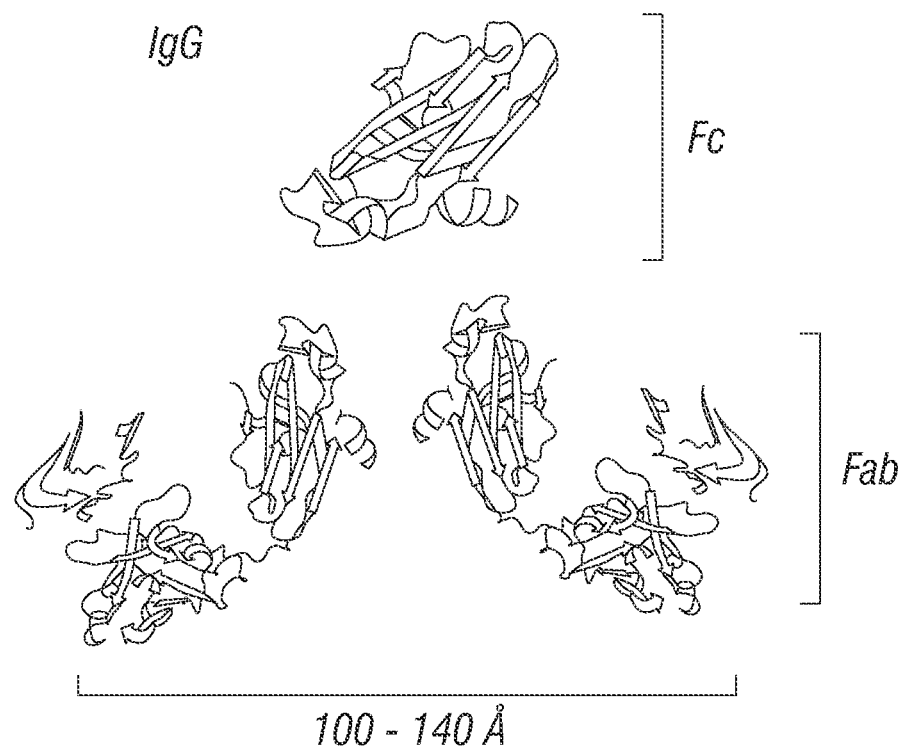
Figure 6A:
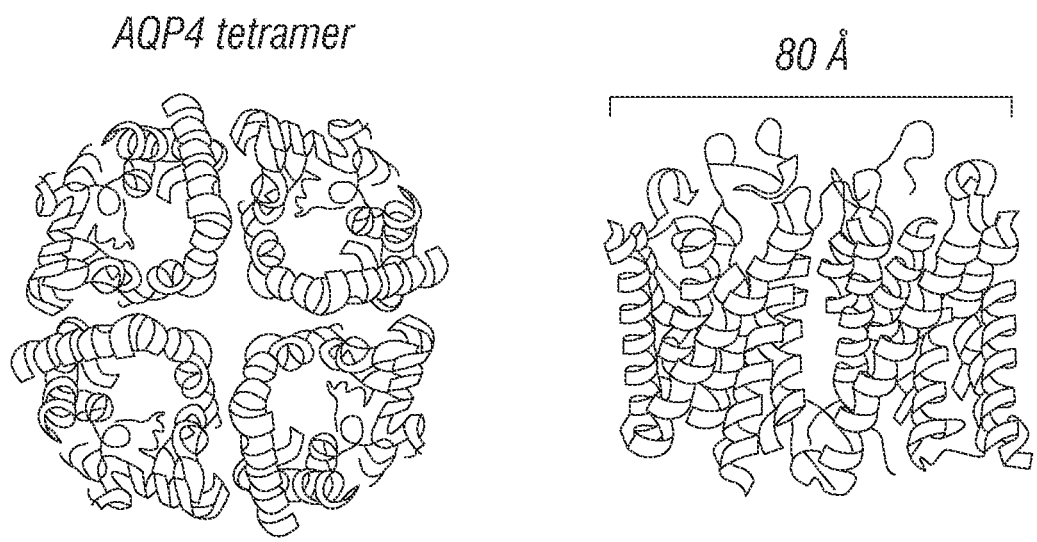

Two potential mechanisms, bivalent vs. monovalent NMO-IgG binding, could account for the greater affinity of NMO-IgG to OAP vs. non-OAP associated AQP4. FIG. 6A shows a comparison of the distance between adjacent Fab binding sites in $IgG_1$ (Sosnick et al., 1992; Harris et al., 1998), and the size of the AQP4 tetramer (Ho et al., 2009). FIG. 6B diagrams possible opposing binding mechanisms. First is bivalent binding. Strong NMO-IgG binding requires a bivalent interaction in which both Fab sites must bind to AQP4 monomers or tetramers. For rAb-53, in which M23 binding is much stronger than M1 binding, the positions of the binding epitopes in AQP4 monomers are spaced such that a bivalent interaction between the Fab sites is not possible within a single tetramer, but is optimal for cross-linking of adjacent tetramers in OAPs. For rAb-58, the epitopes may be located at positions in which bivalent binding in a single tetramer can occur, resulting in similar binding to M1 and M23 AQP4. Second is monovalent binding. NMO-IgG binding involves classical monovalent interactions, and is controlled primarily by affinities of individual Fab' s to their respective epitopes. For rAb-53, a structural change in the epitope site upon OAP formation results in higher affinity. For rAb-58, the epitope site is not altered by OAP formation, resulting in similar affinity for M1 vs. M23 AQP4.

Fab binding to M1 and M23 AQP4 was measured to test these competing mechanisms. NMO-IgGs were digested with papain and purified to yield Fab' s. The bivalent binding mechanism predicts little binding by Fab' s, and no difference between Fab binding to M1 vs. M23 AQP4. The monovalent binding mechanism predicts that the increased binding of rAb-53 to M23 AQP4 would also be observed for its individual Fab' s. As a control, the inventors measured binding of Fab' s generated from a mouse monoclonal anti-Myc antibody to external Myc-tagged AQP4 isoforms. As expected, whole anti-Myc IgG bound Myc-tagged M1 and M23 AQP4 equally, with $K_D$~10 nM (FIG. 6C). FIG. 6D shows the binding of Fab fragments to M1 vs. M23 AQP4. Whole IgG and Fab' s from rAb-53 showed significantly greater binding to M23 AQP4, while whole IgG and Fab' s from rAb-58 and anti-Myc showed similar M1 vs. M23 binding. These data provide direct support for the second mechanism involving monovalent binding.

Example 3—Discussion

Here, the inventors used fluorescence ratio imaging to quantify the binding of NMO-IgG to AQP4, and to determine the role of AQP4 isoforms and OAPs in NMO-IgG binding. This live-cell system was developed out of a need for a robust method to characterize monoclonal NMO-IgGs and polyclonal NMO patient sera. The inventors found that U87MG cells were suitable for quantitative binding measurements because they efficiently expressed AQP4 at the plasma membrane after stable or transient transfection, with little or no intracellular AQP4 expression. The excellent membrane expression of AQP4 in U87MG cells is likely due to their glial origin, and hence their expression of the same trafficking machinery as that in native human glial cells. Immunoblot analysis of the stably transfected clones used in this study shows exclusive expression of individual AQP4 isoforms, with no detectable M23 in the M1 cell line (FIG. 2C). U87MG cells grow rapidly and adhere well to culture supports, making them suitable for automated and high-throughput assays.

For all monoclonal and polyclonal NMO antibodies tested, NMO-IgG binding to M23-expressing cells was comparable to or greater than to M1-expressing cells, though measurable binding to M1 was found in all cases. NMO-IgG was found to bind to each AQP4 isoform in a concentration-dependent manner that fitted well to a single-site, saturable binding model with near unity Hill coefficient, consistent with apparent single-site, non-cooperative binding. Preferential binding of NMO-IgG to M23 AQP4 was found to be a consequence of greater binding affinity rather than to greater binding capacity. Differences in the binding affinity of monoclonal NMO-IgG rAb-53 to the M23 and M1 isoforms of AQP4 was found to be a consequence of OAP formation by M23 AQP4 rather than to differences in the N-terminal sequences. This was proven using mutants of M1 and M23 AQP4 with altered abilities to form and disrupt OAPs. Using a two-color single particle tracking approach, the inventors recently showed that co-expressed AQP4 isoforms M1 and M23 co-assemble in AQP4 tetramers with differential abilities to assemble into OAPs. They also showed that OAP size and content could be altered by changing the M1:M23 ratio, or by altering the palmitoylation state of M1 AQP4 (Crane et al., 2009). The inventors found here that co-expression of M1 and M23 also affects NMO-IgG binding (FIG. 5A). However, by reducing the ability of M1 to disrupt OAPs through expression of a palmitoylation-null M1 mutant, they found significantly increased NMO-IgG binding in mixtures with identical M23:M1 ratio (FIG. 5B). The inventors previously showed that OAP formation by M23 requires N-terminus hydrophobic interactions at residues 24-26 just downstream of Met-23 (Crane and Verkman, 2009), and discovered M23 mutants with greatly reduced ability to form OAPs (M23-F26Q and M23-G28P). These OAP-disrupting M23 AQP4 mutants greatly reduced NMO-IgG binding (FIG. 5C). In contrast to isotherms for binding of NMO-IgG to individual M1 and M23 isoforms, binding to AQP4 mutants M23-F26Q and M23-G28P produced isotherms that did that not fit to a single-site binding model, probably because expression of these mutants produces heterogeneous populations of OAP-assembled AQP4 and non-assembled AQP4 tetramers.

The mechanism for higher affinity NMO-IgG binding to OAP-assembled AQP4 was examined by comparing whole (bivalent) NMO-IgG to its monovalent Fab' s. OAP assembly resulted in a greater affinity for individual Fab binding sites, rather than enhancement by bivalent IgG binding. The inventors propose, therefore, that the binding epitope for many of the IgGs found in NMO may be located at the tetramer/tetramer interface created upon OAP assembly. However, differences in binding affinities vary, likely depending on the epitope structure, and some NMO-IgGs (rAb-58) have strong affinity for unassembled M1 AQP4.

The widely used assay for serum NMO-IgG immunofluorescence is performed in M1 AQP4-expressing HEK-293 cells (Lennon et al., 2005). The data here indicate that M23 AQP4-expressing cells are superior because NMO-IgG binding to M23 AQP4 is as good as and generally much better than binding to M1 AQP4. The difference in binding is seen at all NMO-IgG concentrations and is often quite marked at low concentrations, as often found in human serum specimens. Up to 30% of serum from patients with NMO, as defined by established clinical criteria, are found to be seronegative as assayed using the conventional method (Wingerchuk et al., 2006). This value is likely substantially lower utilizing more sensitive assays such as the imaging assay established here utilizing human glial cell line strongly expressing the OAP-forming M23 isoform of AQP4. Indeed, a recent study of multiple human serum samples indicated an improvement from 70% to 97% sensitivity for NMO-IgG when using M23-expressing cells instead of M1-expressing cells (Mader et al., 2010). This quantitative binding assay established here should also be useful in correlating serum NMO-IgG binding affinity and specificity with NMO clinical parameters, such as disease activity, treatment status and patient characteristics. Baseline differences in NMO-IgG binding to OAP vs. non-OAP associated AQP4 may have diagnostic significance, and spontaneous and treatment-associated changes in binding may have prognostic significance.

Example 4—Materials and Methods

Recombinant NMO-IgGs and NMO Patient Sera.
Recombinant monoclonal NMO antibodies (rAbs) were generated from clonally-expanded plasma blasts in cerebrospinal fluid (CSF) as described (Bennett et al., 2009). For site-directed mutagenesis, the KpnI-XhoI fragment of the IgG1 heavy chain constant region (IgG1Fc) was cloned into pSp73X. Point mutations were introduced into the IgG1Fc sequence using the GeneTailor Site-Directed Mutagenesis System (Invitrogen) to generate constructs deficient in CDC (mutation K322A), ADCC (mutations K326W/E333S) or both (mutations L234A/L235A) (Baudino et al., 2008; Duncan and Winter, 1988; Hezareh et al., 2001; Idusogie et al., 2001). The AgeI-XhoI fragment of the mutated IgG1Fc sequence was cloned into pIgG1Flag containing the heavy-chain variable region sequence of rAb-53 to generate aquaporumab constructs containing a mutant IgG1 Fc sequence with a C-terminal Flag epitope.

For generation of divalent rAbs and aquaporumab, paired heavy and light chain constructs were co-transfected into HEK293 cells using lipofectamine. After transfection, cells were grown for 7 days in DMEM medium+10% FBS, the supernatant harvested, fresh medium added, and the cells were grown for another 7 days. The cell culture supernatants were combined, centrifuged at 2000 rpm for 10 min to pellet cells and debris, and the cell-free supernatant was adjusted to pH 8.0 with 1M Tris pH 8.0 and incubated overnight with protein A-Sepharose (Sigma-Aldrich) at 4° C. The rAb was eluted from the protein A-Sepharose in 0.1 M glycine/1M NaCl (pH 3.0) and adjusted to pH 7.5 with 0.1M Tris-HCl, pH 8.0. Recombinant IgGs were exchanged and concentrated in PBS containing 0.1% protease-free bovine serum albumin (BSA) using Ultracel YM-30 microconcentrators (Millipore, Billerica, Mass.). BSA was excluded from the storage solution for surface plasmon resonance measurements. Antibody integrity was confirmed by denaturing and native gel electrophoresis, and IgG concentration was assayed using a human IgG-capture ELISA. NMO serum was obtained from a total of ten NMO-IgG seropositive individuals who met the revised diagnostic criteria for clinical disease (Wingerchuk et al., 2006). Control (non- NMO) human serum was obtained from a total of three non-NMO individuals, or purchased from the UCSF cell culture facility. For some studies total IgG was purified and concentrated from serum using a Melon Gel IgG Purification Kit (Thermo Fisher Scientific, Rockford, Ill.) and Amicon Ultra Centrifugal Filter Units (Millipore, Billerica, Mass.).

Cell Culture and Transfections.

DNA constructs encoding human AQP4 were generated by PCR-amplification using whole brain cDNA as template. PCR fragments were ligated into mammalian expression vector pcDNA3.1 and fully sequenced. COS-7 (ATCC CRL-1651), U87MG (ATCC HTB-14) and CHO-K1 (ATCC CCL-61) cell cultures were maintained at 37° C. in 5% $CO_2$/95% air in the appropriate medium containing 10% fetal bovine serum, 100 U/mL penicillin and 100 µg/mL streptomycin. NK-92 cells expressing CD16 (CD16-176V-NK92, obtained from Fox Chase Cancer Center) were cultured at 37° C. in 5% $CO_2$/95% air in a-MEM with deoxyribonucleosides and ribonucleosides containing 10% fetal bovine serum, 10% horse serum, 0.1 mM 2-mercaptoethanol, 2 mM glutamine, 0.2 mM myo-inositol, 2.5 µM folic acid, non-essential amino acid, 110 µg/mL sodium pyruvate, 100 U/mL penicillin and 100 µg/mL streptomycin.

Surface Plasmon Resonance.

Real-time binding of rAbs to AQP4 was measured by surface plasmon resonance at 25° C. using a Biacore T-100 instrument (GE Healthcare Life Sciences, Piscataway, N.J.), based on reported procedures (Patel et al., 2009). Purified recombinant human M1 AQP4 (provided by William Harries and Robert Stroud, UCSF) was reconstituted at 3% (wt/wt) AQP4 in proteoliposomes containing 95:5 L-a-phosphatidylcholine:L-a-phosphatidylserine (Avanti Polar Lipids) ratio. Briefly, lipids (total 37.5 mg, 500 nmol) was dissolved in 375 µL of 40 mM b-octyl glucoside (in PBS) followed by addition of AQP4 (300 ml, 450 mg, 15 nmol). The mixture was dialyzed (10,000 dalton cut-off) against PBS at 4° C. for 48 h. For preparation of AQP4-free liposomes, an equal volume of 40 mM b-octyl glucoside (instead of AQP4) was added to the lipid solution. Proteoliposomes were immobilized on a L1 sensor chip (Biacore) with four injections at 10 min/injection at 2 µl/min to achieve 6000 response units of proteoliposomes immobilization. The surface was then washed with two 20 s injections of 50 mM NaOH at 100 µl/min, and checked for surface quality with a 300 s injection of 0.01 mg/ml BSA at 20 µl/min. Flow channel 1 (Fc 1) was immobilized with 0% AQP4 as reference, and Fc 2 contained the AQP4 proteoliposomes. Binding studies were conducted with PBS at a flow rate of 15 µl/min. rAbs in PBS were injected for 80 s followed by a post-injection period of 240 s. Regeneration was performed by injection of 50 mM NaOH at 100 µl/min for 20 s. Binding studies were done in duplicate. Data were analyzed using Biacore T100 Evaluation software.

NMO-IgG Binding to AQP4 in Cells.

The kinetics of rAb-53 binding to AQP4 was measured in U87MG cells stably expressing human AQP4-M23 by quantitative imaging as described (Crane et al., 2011). Cells were incubated for 20 min in live-cell blocking buffer (PBS containing 6 mM glucose, 1 mM pyruvate, 1% bovine serum albumin, 2% goat serum), and then for specified times with NMO-IgG. Cells were then rinsed, fixed in 4% paraformaldehyde for 15 min, and permeabilized with 0.1% Triton X-100. Cells were then blocked again and incubated for 30 min with 0.4 µg/mL polyclonal, C-terminal specific rabbit anti-AQP4 antibody (Santa Cruz Biotechnology, Santa Cruz, Calif.), then rinsed with PBS. Finally, cells were incubated for 30 min with 4 µg/mL goat anti-human IgG-conjugated Alexa Fluor 488 and goat anti-rabbit IgG-conjugated Alexa Fluor 555 (Invitrogen) in blocking buffer. NMO-IgG binding was quantified by ratio image analysis as described (39). In some studies rAb-53 was fluorescently labeled with Cy3 using standard succinimidyl chemistry.

Assays of Complement-Dependent Cytotoxicity (CDC) and Antibody-Dependent Cell-Mediated Cytotoxicity (ADCC).

For assay of CDC, CHO cells expressing human AQP4 were pre-incubated for 30 min with 12.5 µg/ml aquaporumab (or control IgG), then for 90 min at 37° C. with NMO-IgG (2.5 µg/ml) or control-IgG and 5% human complement. Calcein-AM and ethidium-homodimer (Invitrogen) were then added to stain live cells green and dead cells red. Complement-mediated cytotoxicity by 1-2% NMO patient sera (and control non-NMO sera) and 5% human complement were was measured similarly without vs. with 50-100 µg/ml aquaporumab. For assay of ADCC, NK-92 cells expressing CD16 were used as the effector cells. The AQP4-expressing CHO cells were pre-incubated for 30 min with 15 µg/ml aquaporumab (or control-IgG), then for 3 h at 37° C. with NMO-IgG (5 µg/ml) or control-IgG and effector cells (effector:target ratio 30:1). Cells were rinsed with PBS before adding calcein-AM and ethidium-homodimer.

In Vivo NMO Model.

Adult mice (30-35 g) were anaesthetized with 2,2,2-tribromoethanol (125 mg/kg i.p.) and mounted in a stereotactic frame. Mice were injected intracerebrally, as described (Saadoun et al., 2010), with purified total IgG (14 µA, 6-38 mg/mL) isolated NMO patient serum (5 different NMO seropositive patients studied) plus human complement (10 µL), without or with aquaporumab (10 µg). Controls included non-NMO human IgG (3 different control sera studied), use of AQP4 null mice, and injection of aquaporumab alone. Mice were killed at 24 h after injection and brains were fixed in formalin, processed into paraffin, and sectioned coronally at 1.6 mm from the frontal poles. Sections were stained with hematoxylin/eosin, Luxol Fast Blue (for myelin) or immunostained with antibodies against AQP4 (Millipore, Watford, UK) and C5b-9 (Abcam, Cambridge, UK). Micrographs were quantified for loss of AQP4 immunoreactivity and myelin as described (Saadoun et al., 2010; Crane et al., 2011).

Ex Vivo NMO Model.

Organotypic spinal cord slice cultures were prepared using a modified interface-culture method. Postnatal day 7 mouse pups were decapitated and the spinal cord was rapidly removed and placed in ice-cold Hank's balanced salt solution (HBSS, pH 7.2). Transverse slices of cervical spinal cord of thickness 300 µm were cut using a vibratome (Leica VT-1000S; Leica). Individual slices were placed on transparent, non-coated membrane inserts (Millipore, Millicell-CM 0.4 µm pores, 30 mm diameter) in 6-well (35 mm) plates containing 1 mL culture medium, with a thin film of culture medium covering the slices. Slices were cultured in 5% $CO_2$ at 37° C. for 10 days in 50% minimum essential medium (MEM), 25% HBSS, 25% horse serum, 1% penicillin-streptomycin, glucose (0.65%) and HEPES (25 mM) (changed every 3 days). On day 7, purified IgG (isolated from NMO patient or control sera, 300 µg/ml) and human complement (10%) were added to the culture medium without or with aquaporumab (L234A/L235A or K322A, 10 µg/ml). The slices were cultured for another 3 days, and fixed for AQP4, GFAP and MBP immunofluorescence. Sections were scores as follows: 0, intact slice with uniform and intact GFAP and AQP4 staining; 1, intact slice with some astrocyte swelling seen by GFAP staining, with reduced AQP4 staining; 2, at least one lesion in the slice with loss of GFAP and AQP4 staining; 3, multiple lesions affecting >30% of slice area with loss of GFAP and AQP4 staining; 4, extensive loss of GFAP and AQP4 staining affecting >80% of slice area. Slices from AQP4 null mice scored from GFAP immunofluorescence only.

Example 5—Results

Figure 7A:
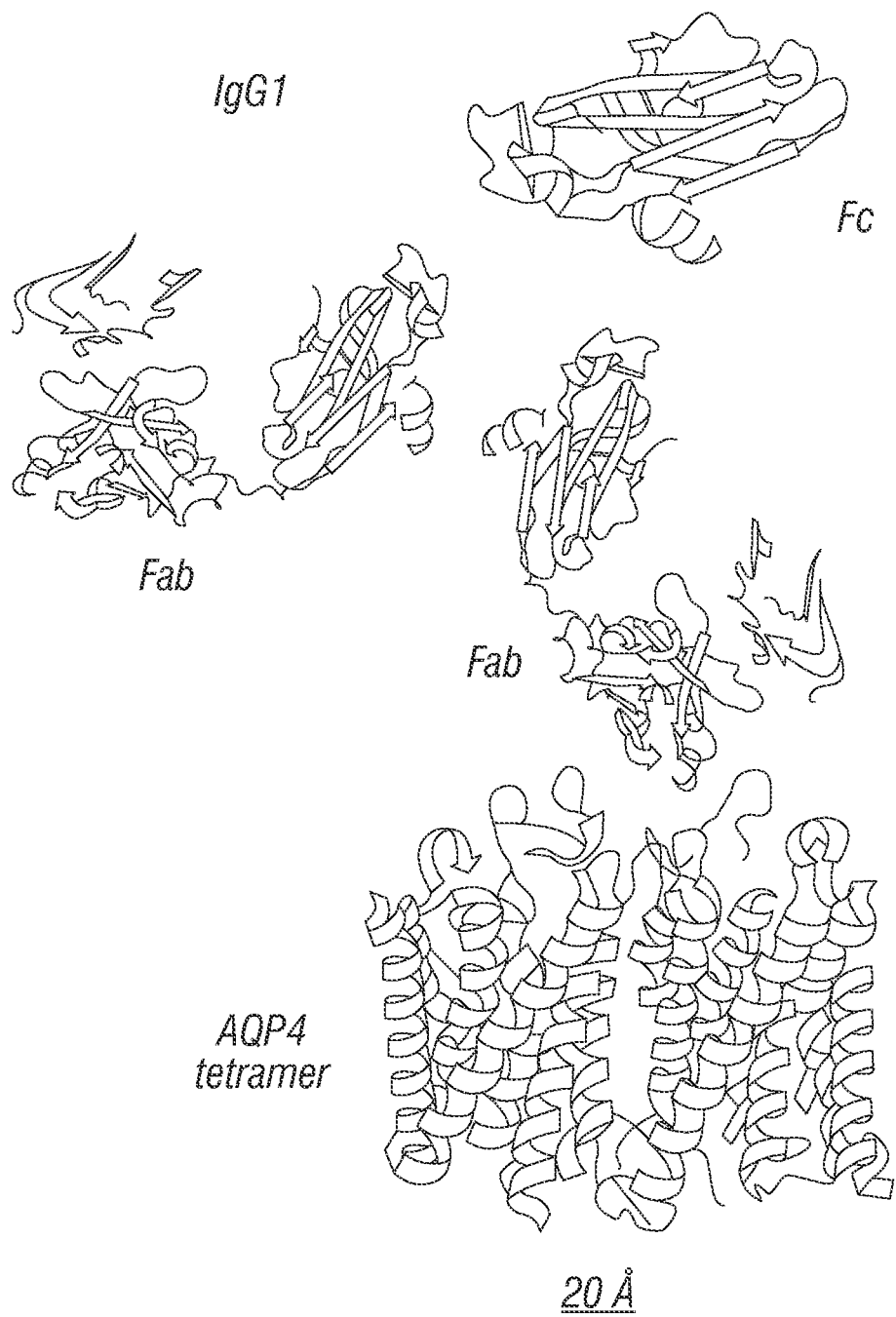
FIGS. 7A-C High-affinity monoclonal, recombinant anti-AQP4 antibody for aquaporumab therapy.

The rationale for aquaporumab therapy of NMO is depicted in FIG. 7A. Pathogenic autoantibodies that bind to extracellular epitopes on AQP4 (NMO-IgG) are substantially larger than AQP4 tetramers, preventing the simultaneous binding of more than one antibody. The inventors reasoned, therefore, that a non-pathogenic antibody with high binding affinity and slow washout would compete with the binding of pathogenic antibodies and thus block downstream astrocyte damage and neuroinflammation.

Figure 7B:
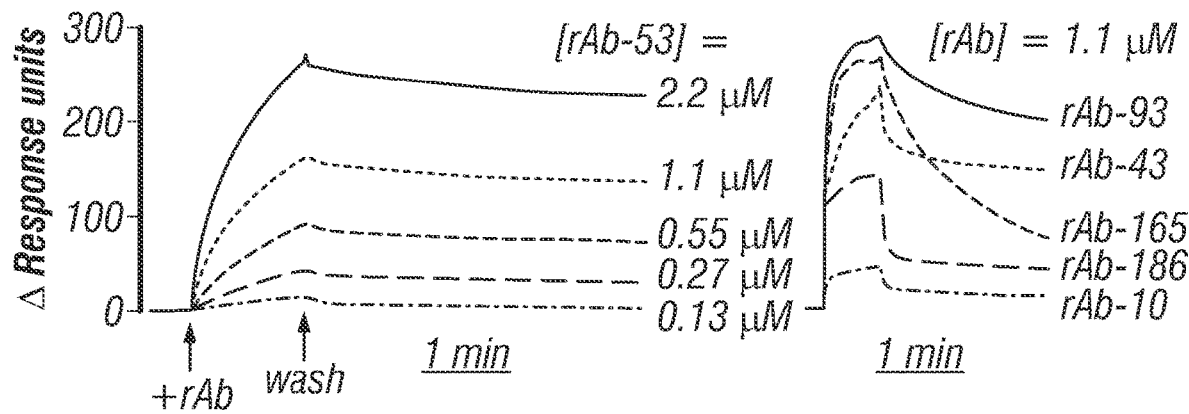
Figure 7C:
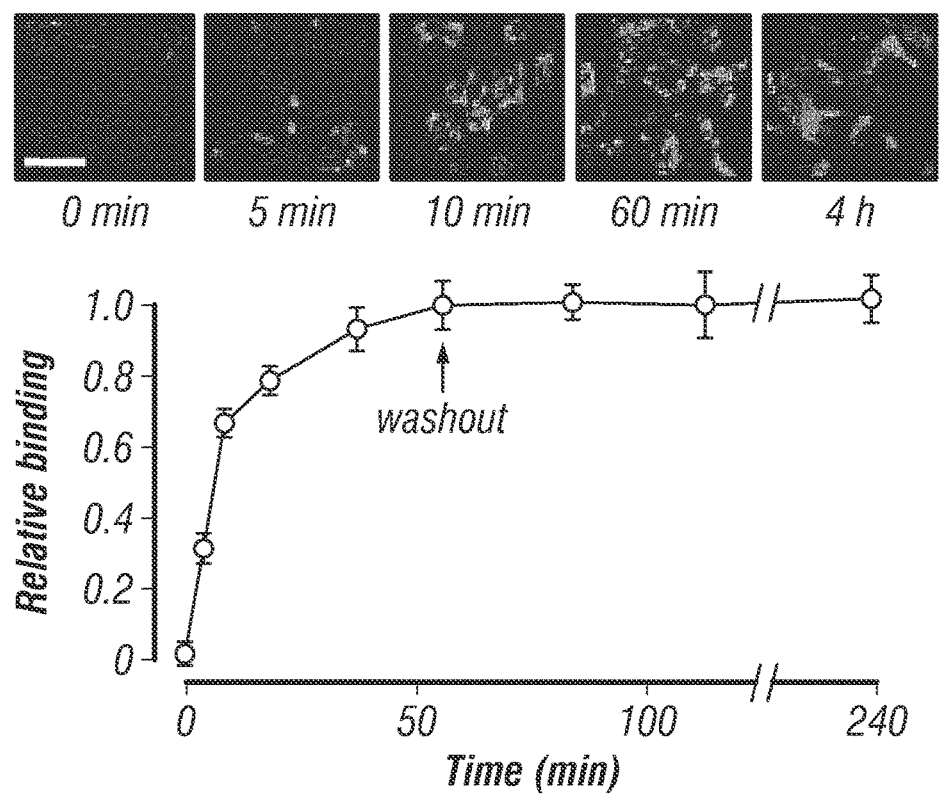

In order to engineer suitable non-pathogenic AQP4 antibodies, the inventors generated and screened ten recombinant monoclonal NMO-IgGs that were derived from clonally expanded plasma blast populations in the CSF of three NMO patients. Paired heavy and light chain variable region sequences from single cells were PCR-amplified, cloned into expression vectors containing heavy and light chain constant region sequences, coexpressed in HEK293 cells, and the recombinant IgG purified from supernatants. Binding of each monoclonal recombinant antibody to AQP4 in reconstituted proteoliposomes was measured by surface plasmon resonance. Of ten recombinant antibodies tested, the inventors found highest affinity and slowest washout for antibody rAb-53 (FIG. 7B, left). Binding of rAb-53 to AQP4-proteoliposomes occurred within a few minutes (binding rate constant $1.4 \times 10^4$ $M^{-1}s^{-1}$) and washout over many hours (off rate constant $3.8 \times 10^{-4}$ $s^{-1}$), with an apparent binding affinity of 27 nM. Other recombinant NMO antibodies had substantially rapid washout and reduced binding affinity (examples shown in FIG. 7B, right). Slow rAb-53 washout was verified in live cells expressing AQP4. FIG. 7C shows rAb-53 binding over 5-10 minutes, without measurable washout over 3 hours.

Figure 8A:
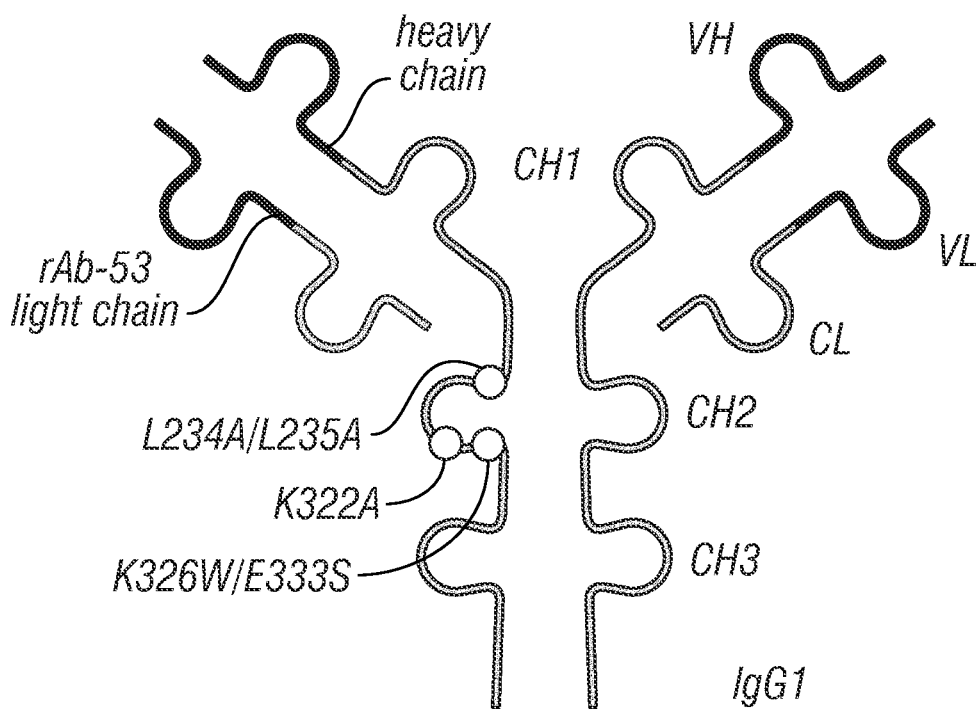
FIGS. 8A-D. Mutated, non-pathogenic rAb-53 (aquaporumab) blocks binding of pathogenic NMO-IgG to AQP4.
Figure 8B:
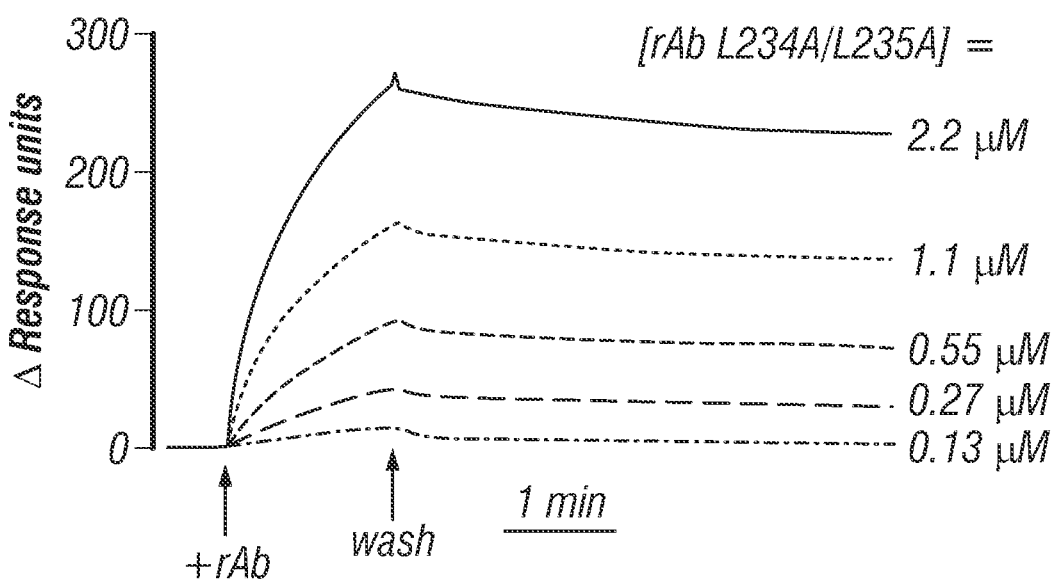

Point mutations in the Fc portion of rAb-53 were introduced in order to inhibit CDC (K322A), ADCC (K326W/E333S) or both (L234A/L235A), while preserving the AQP4-binding Fab sequences (FIG. 8A). Introduction of these mutations did not affect antibody binding to AQP4, with representative surface plasmon resonance data for one of the mutated antibodies shown in FIG. 8B. As expected, the Fc mutations did not significantly alter on or off binding rate constants or reduce binding affinities.

Figure 8C:
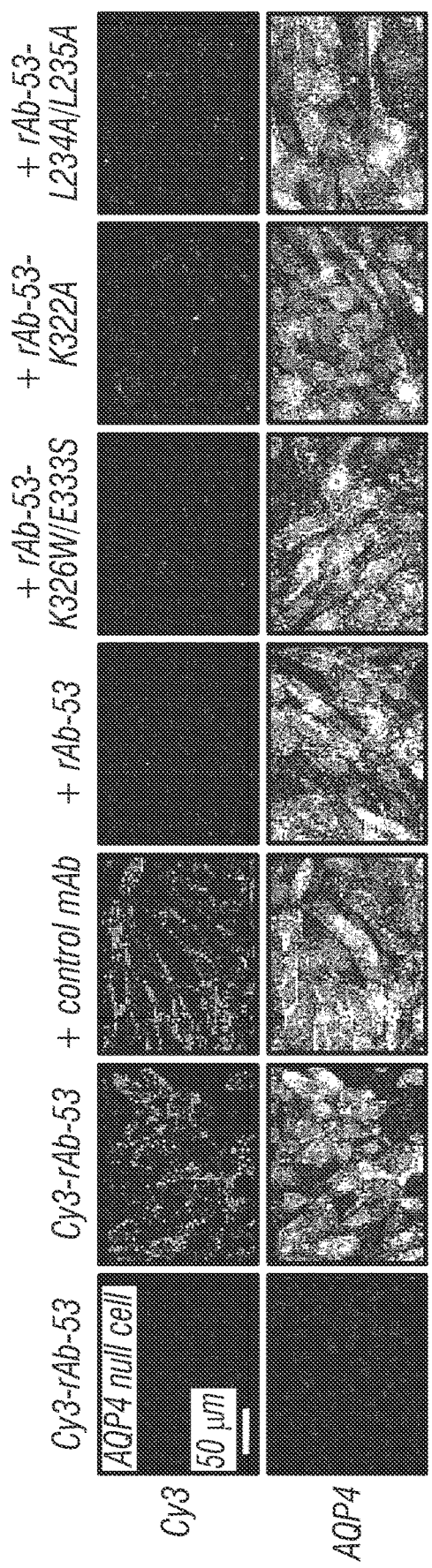
Figure 8D:
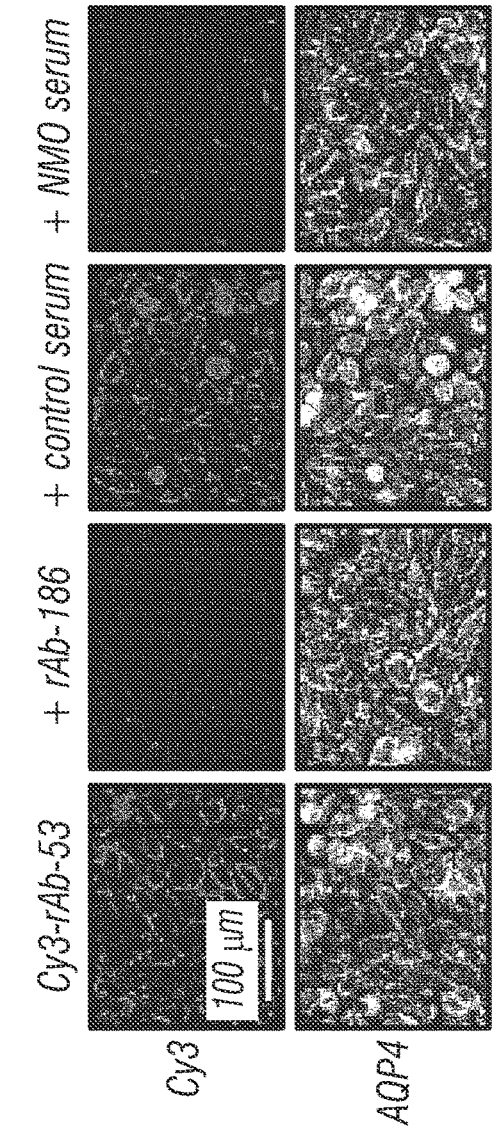

To determine whether the mutated rAb-53 antibodies blocked binding of non-mutated rAb-53, rAb-53 was fluorescently labeled with Cy3 under conditions that did not affect binding to AQP4. FIG. 8C shows that a 5-fold excess of each of the mutated antibodies, as well as non-mutated rAb-53, blocked the binding of Cy3-labeled rAb-53 to AQP4-expressing cells. A non-AQP4-specific (isotype control) monoclonal recombinant antibody had no effect. Importantly, human NMO serum, which contains a polyclonal mixture of NMO-IgGs, blocked binding of Cy3-labeled rAb-53 (one of five representative human NMO sera shown in FIG. 8D), as did other monoclonal NMO antibodies (rAb-186 shown in FIG. 8D). Non-NMO (control) human serum had no effect. These data suggest competition among NMO autoantibodies for binding to surface epitopes on AQP4.

Figure 9A:
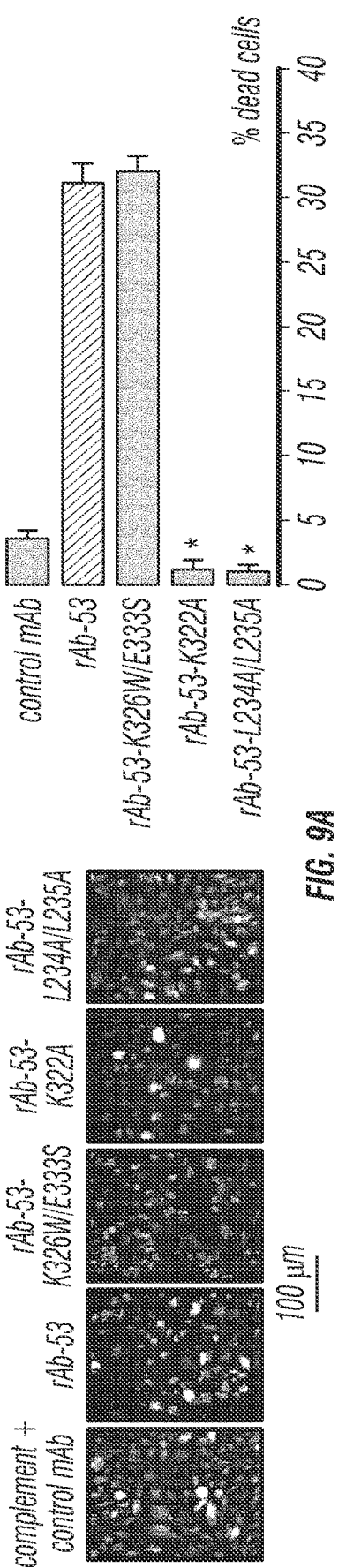
FIGS. 9A-D. Mutated non-pathogenic rAb-53 aquaporumabs prevents CDC and ADCC in NMO-IgG-exposed AQP4-expressing cells.
Figure 9B:
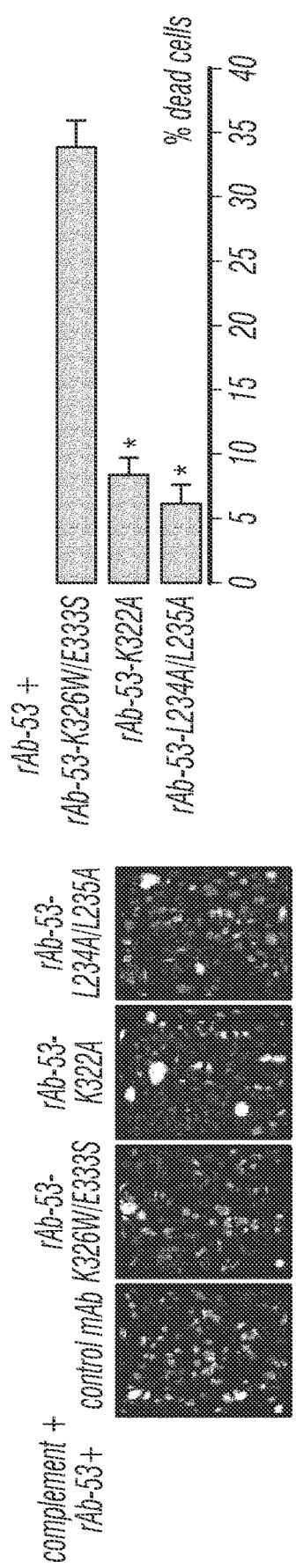

A major downstream consequence of NMO-IgG binding to cell surface AQP4 is complement-mediated cell killing. FIG. 9A shows a live/dead cell assay in which live cells are stained green and dead cells red. Incubation of AQP4-expressing cells with rAb-53 and complement together caused extensive cell killing. The rAb-53 mutants K322A and L234A/L235A, which are deficient in complement C1q activation, caused little cell killing, whereas K326W/E333S, which has intact complement binding, caused cell killing. In control studies, complement or rAb-53 alone did not cause cell killing, nor did rAb-53 and complement together when incubated with AQP4 null cells (not shown). FIG. 9B shows that a five-fold molar excess of K322A or L234A/L235A greatly reduced cell killing by rAb-53 with complement.

Figures 9C, 9D:
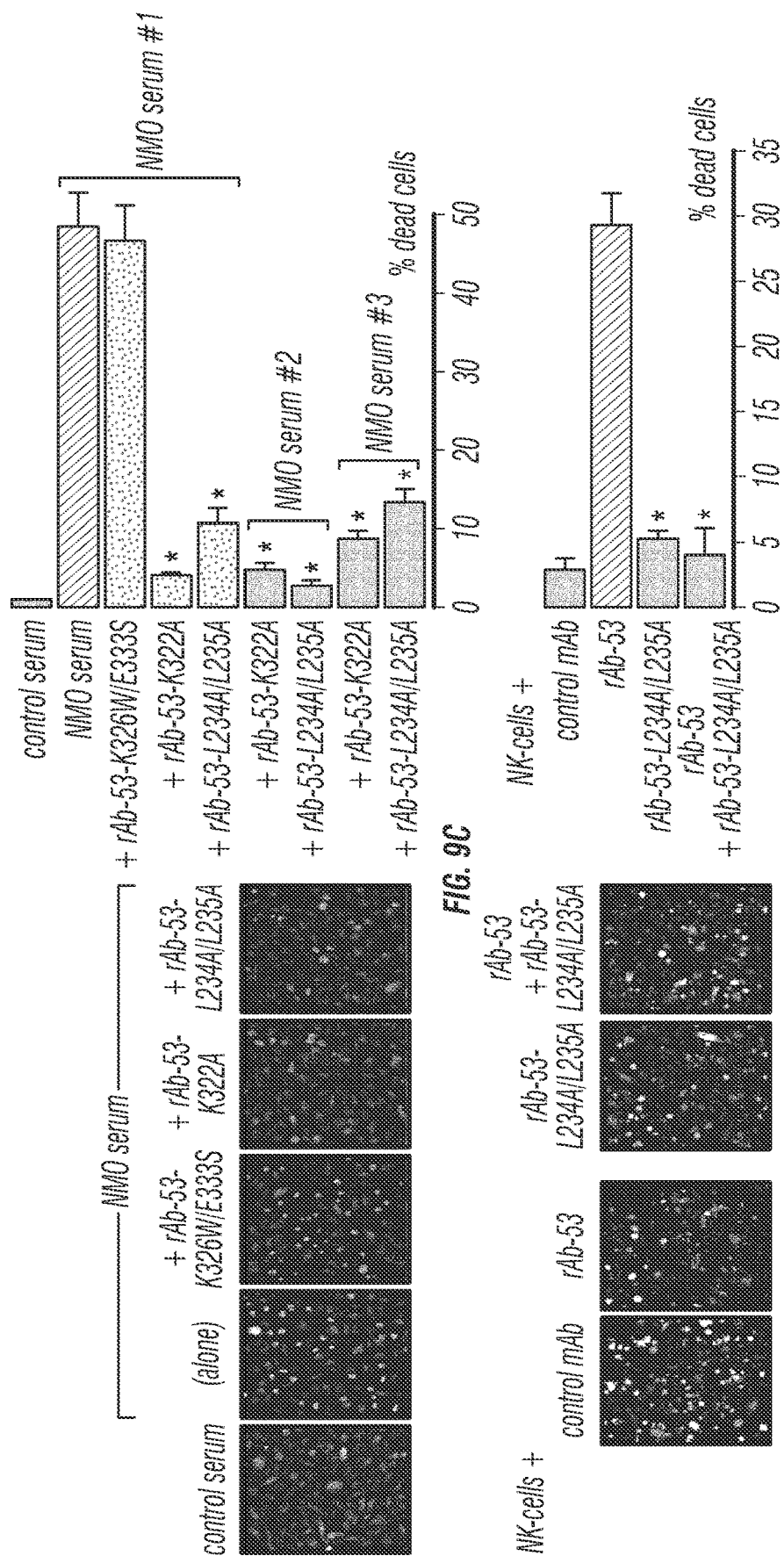

The polyclonal mixture of NMO-IgGs in NMO patient serum is thought to recognize various overlapping 3-dimensional epitopes on the extracellular surface of AQP4. FIG. 9C shows that rAb-53 mutants K322A and L234A/L235A blocked complement-mediated cell killing by NMO sera from different NMO patients (representative data from 3 of 6 patient sera shown). Control (non-NMO) serum did not cause cell killing. Therefore, the aquaporumabs rAb53-K322A and L234A/L235A block binding of different NMO-IgGs and consequent cell killing, probably by steric hindrance at the AQP4 surface.

The ability of aquaporumab to reduce NMO-IgG-dependent ADCC was also verified. AQP4-expressing cells were incubated with NK-cells in the absence or presence of rAb-53 and in the absence or presence of rAb-53 mutant L234A/L235A. FIG. 9D shows marked killing by NK-cells in the presence of rAb-53, with little killing by NK-cells in the presence of control antibody or aquaporumab. Inclusion of aquaporumab L234A/L235A during the incubation with NK-cells and rAb-53 greatly reduced cell killing.

Figure 10A:
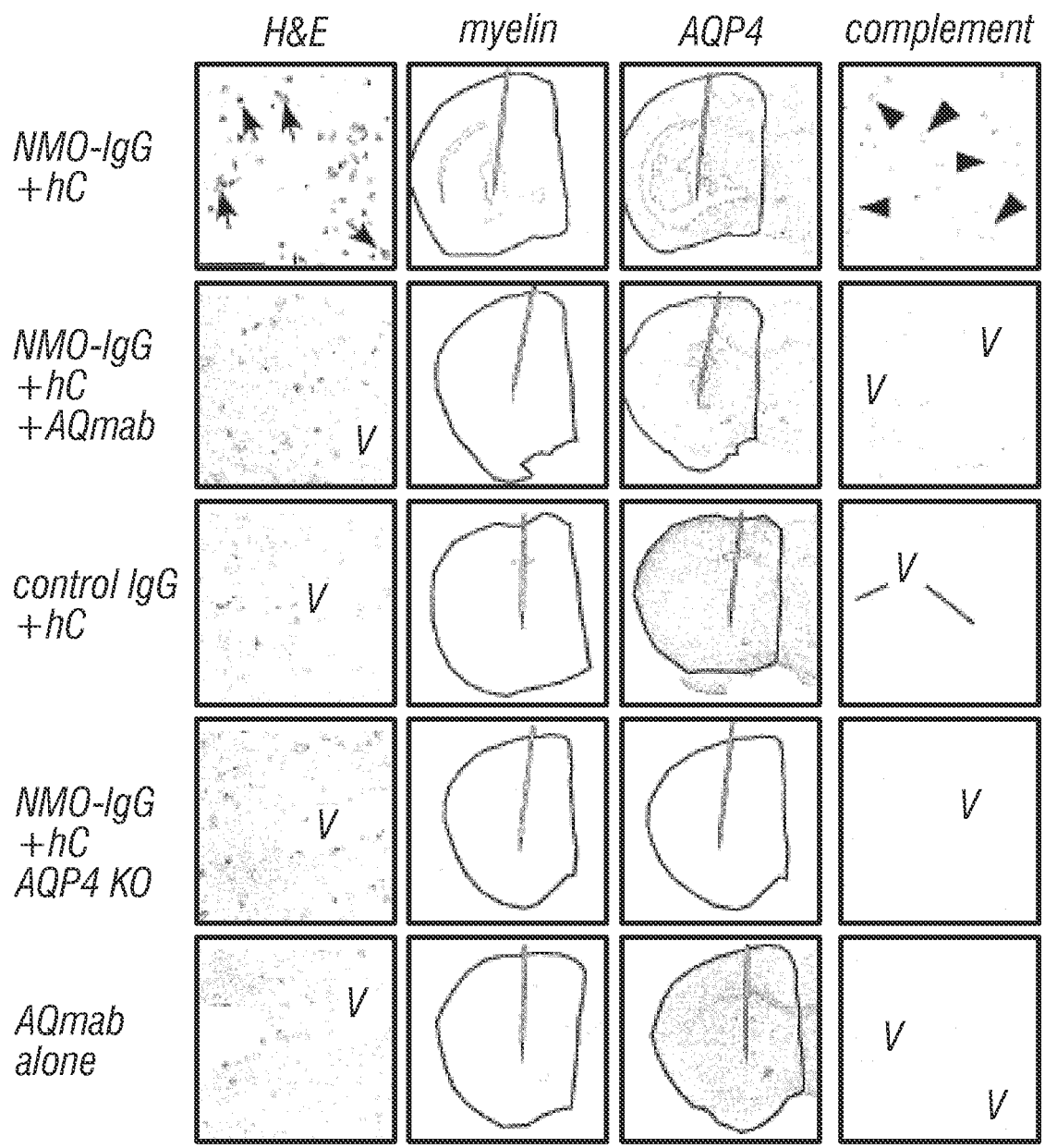
FIGS. 10A-C. Aquaporumab reduces NMO-like lesions in mouse brain in vivo produced by intracerebral injection of NMO-IgG and human complement.
Figure 10B:
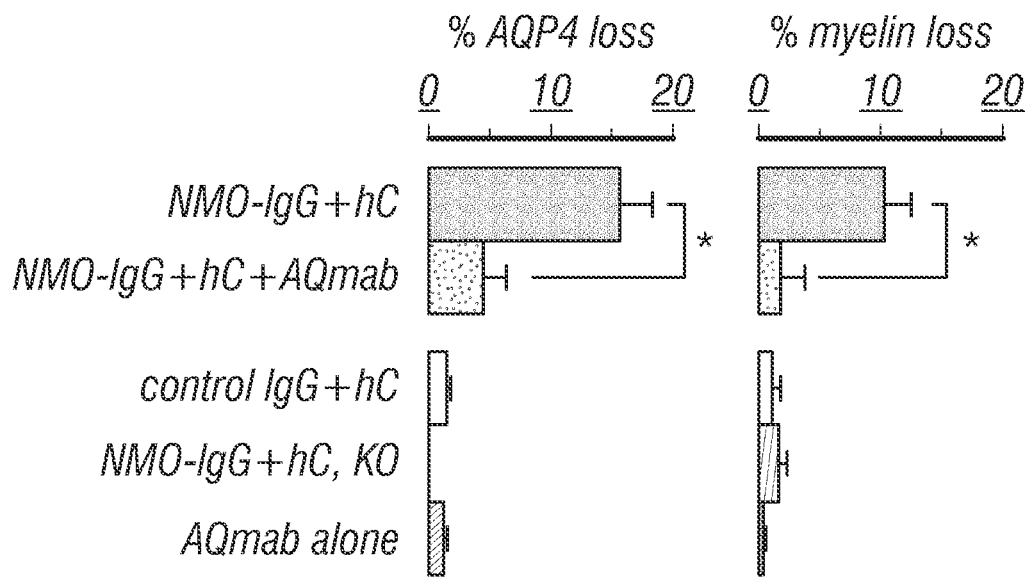
Figure 10C:
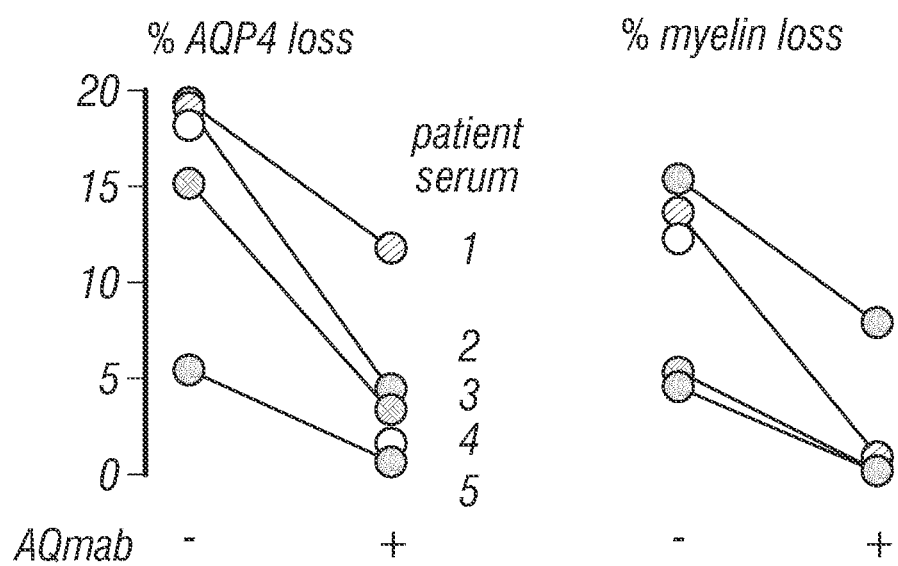

Proof-of-concept studies were done in in vivo and ex vivo NMO models to investigate the efficacy of aquaporumab in reducing NMO lesions. NMO lesions were created in mouse brain in vivo by intraparenchymal injection of IgG purified from NMO serum, together with human complement. At 24 h after injection, there was marked inflammatory cell infiltration (primarily neutrophils), loss of AQP4 and myelin, and vasculocentric complement activation in the injected hemisphere (FIG. 10A). In control experiments, there was little or no inflammatory cell infiltration, loss of myelin, loss of AQP4 or complement activation following intracerebral injection of: (i) control (non-NMO) human IgG with complement; (ii) NMO-IgG with complement in AQP4 null mice; or (iii) aquaporumab alone. Coinjection of NMO-IgG and complement with aquaporumub greatly reduced AQP4 and myelin loss, as quantified for a series mice in FIG. 10B. FIG. 10C shows data from five pairs of mice in which NMO-IgG from different seropositive NMO patients was injected with or without aquaporumab. Aquaporumab greatly reduced lesion size.

Figure 11A:
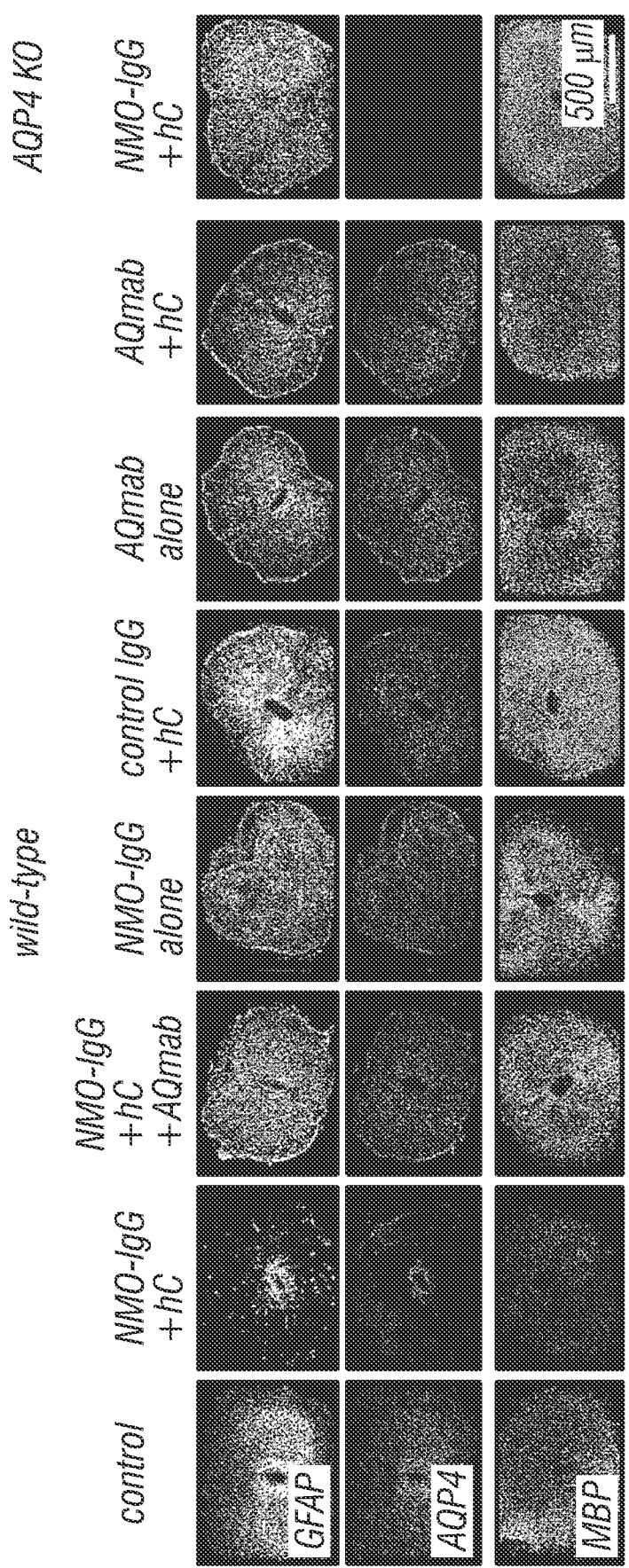
FIGS. 11A-B. Aquaporumab reduces NMO-like lesions produced by NMO-IgG and human complement in ex vivo spinal cord slice cultures.
Figure 11B:
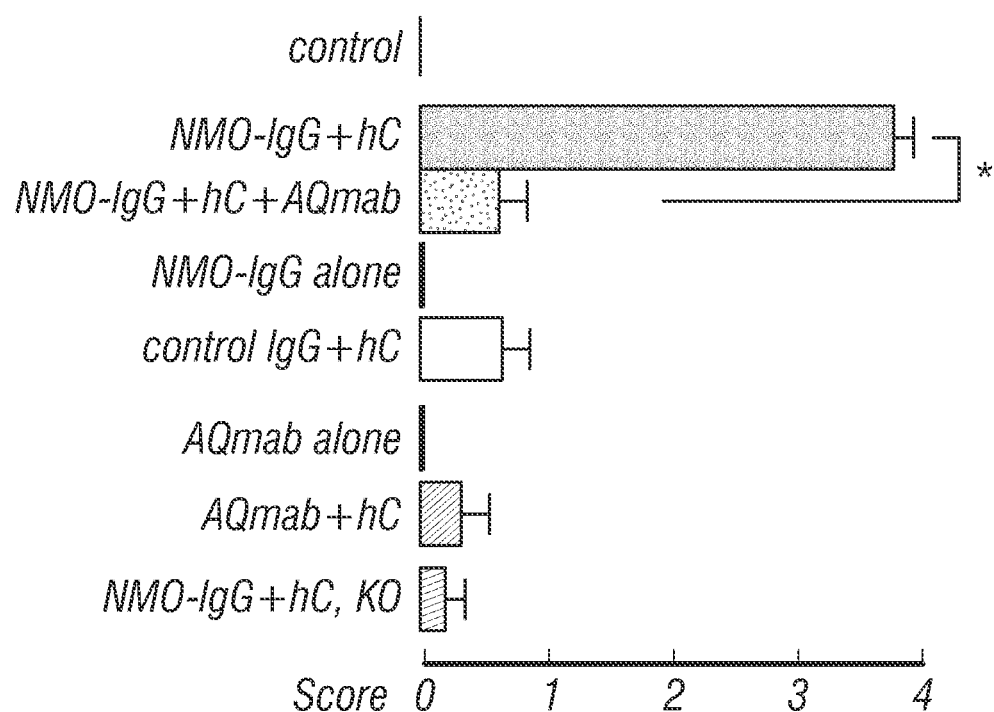

Studies were also performed in an ex vivo spinal cord slice model of NMO in which spinal cord slices from mice were cultured for 7 days, and then incubated for 3 days with NMO-IgG (purified IgG from NMO patient serum) and human complement. This ex vivo model allows for exposure of CNS tissue to antibodies and complement under defined conditions. As shown in FIG. 11A, NMO-IgG and complement produced characteristic NMO lesions with marked loss of AQP4, GFAP and myelin immunofluorescence, which was not seen in the absence of complement or in spinal cord slices from AQP4 null mice. Inclusion of aquaporimub greatly reduced the severity of NMO lesions, with preservation of AQP4, GFAP and myelin. Incubation with aquaporimab alone or with complement produced little or no pathology. FIG. 11B summarizes histological scores of NMO lesion severity. Similar protection by aquaporimub was found for rAb-53, and for NMO-IgG from two other NMO patients.

Example 6—Discussion

The data presented here provide evidence of the utility of aquaporumab blocking antibodies for NMO therapy. The engineered high-affinity, non-pathogenic, recombinant monoclonal antibodies blocked cell surface AQP4 binding of polyclonal NMO-IgG in NMO patient sera in cell culture, ex vivo spinal cord and in vivo mouse models of NMO, preventing downstream cytotoxicity and NMO lesions. Though monoclonal antibody therapy has been used for a wide variety of targets and diseases, the idea of a non-pathogenic blocking monoclonal antibody is novel, as is the idea of targeting an autoantibody-antigen interaction for therapy of an autoimmune disease. NMO is a unique disease ideal for monoclonal antibody blocker therapy because the single target of pathogenic autoantibodies, AQP4, is a plasma membrane protein having a small extracellular footprint compared to antibody size, and pathology is dependent on antibody effector function.

Though mutated, complete IgG1 antibodies were used here for initial proof-of-concept studies, many modifications are possible to augment the therapeutic efficacy of aquaporumab. Variations in antibody design, such as the use of single-chain antibodies or antibody conjugates (Hagemeyer et al., 2009), may increase aquaporumab stability and CNS penetration (Kontermann, 2009), and mutagenesis of the variable domains may increase AQP4 binding avidity (Igawa et al., 2011; Nieri et al., 2009). Alternative antibody isotypes, such as IgG4, may increase therapeutic efficacy by eliminating residual effector function in the IgG1 Fc region (Kaneko and Niwa, 2011). Intravenous aquaporumab therapy for NMO is potentially useful during acute disease exacerbations to reduce NMO pathology when the blood-brain barrier at the lesion site is open, and perhaps for maintenance therapy to reduce the frequency and severity of exacerbations. Intravitreal administration of aquaporumab may be efficacious in limiting retinal ganglion cell loss following optic neuritis in NMO.

It is important that aquaporumab itself not produce CNS pathology. Pathology was not seen following aquaporumab incubation with spinal cord slices or direct intracerebral injection. Although the NMO attack severity has been correlated with the degree of complement activation (Hinson et al., 2009), the possibility of complement- and cell-independent NMO pathology has been proposed (Marignier et al., 2010). It has been suggested from data in a transfected cell model that NMO-IgG causes AQP4 and EAAT2 internalization (Hinson et al., 2008), which may contribute to NMO pathology. If correct, similar internalization by aquaporumab is possible. However, the inventors have found little or no NMO-IgG-induced loss or internalization of AQP4 in astrocytes in the intact CNS (Ratelade et al., 2011). Indeed, the complete absence of AQP4 in mice does not cause baseline abnormalities in CNS anatomy or function; only significant stresses produced phenotypes of altered water balance (Manley et al., 2000; Papadopoulos et al., 2004), neuroexcitation (Binder et al., 2006; Padmawar et al., 2005), glial scarring (Auguste et al., 2007; Saadoun et al., 2005) and neuroinflammation (Li et al., 2011). Though AQP4 is also expressed outside of the CNS in kidney, lung, stomach, skeletal muscle and exocrine glands, its deletion in mice does not produce pathology or significant functional impairment (Verkman, 2008). It is thus unlikely that aquaporumab therapy would itself produce toxicity, though a full, formal evaluation of toxicity is needed for further pre-clinical development.

In conclusion, blocking of NMO-IgG interaction with AQP4 by aquaporumab non-pathogenic antibodies represents a novel approach for NMO therapy. Non-pathogenic blocking antibodies may have therapeutic utility in other autoimmune diseases as well.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VIII. References

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,472,509
U.S. Pat. No. 4,554,101
U.S. Pat. No. 4,680,338
U.S. Pat. No. 4,816,567
U.S. Pat. No. 4,867,973
U.S. Pat. No. 4,938,948
U.S. Pat. No. 5,021,236
U.S. Pat. No. 5,141,648
U.S. Pat. No. 5,196,066
U.S. Pat. No. 5,563,250
U.S. Pat. No. 5,565,332
U.S. Pat. No. 5,856,456
U.S. Pat. No. 5,880,270
"Antibodies: A Laboratory Manual," CHS Press, Cold Spring Harbor, N.Y., 1988.
Abbondanzo et al., *Am. J. Pediatr. Hematol. Oncol.*, 12(4), 480-489, 1990.
Allred et al., *Arch. Surg.*, 125(1), 107-113, 1990.
Atherton et al., *Biol. of Reproduction*, 32, 155-171, 1985.
Auguste et al., *FASEB J.*, 21:108-116, 2007.
Baudino et al., *J. Immunol.*, 181:4107-4112, 2008.
Beidler et al., *J. Immunol.*, 141(11):4053-4060, 1988.
Bennett et al., *Ann. Neurol.*, 66:617-629, 2009.
Binder et al., *Acta Neurochir. Suppl.*, 96:389-392, 2006.
Binder et al., *Glia*, 53:631-636, 2006.
Bradl et al., *Ann. Neurol.*, 66:630-643, 2009.

Brown et al., *J. Immunol. Meth.*, 12; 130(1), :111-121, 1990.
Campbell, In: *Monoclonal Antibody Technology, Laboratory Techniques in Biochemistry and Molecular Biology*, Vol. 13, Burden and Von Knippenberg, Eds. pp. 75-83, Amsterdam, Elsevier, 1984.
Capaldi et al., *Biochem. Biophys. Res. Comm.*, 74(2):425-433, 1977.
Crane and Verkman, *Biophys. J.*, 94:702-713, 2008.
Crane and Verkman, *J. Cell Sci.*, 122:813-821, 2009.
Crane et al., *J. Biol. Chem.*, 2011 (Epub ahead of print).
Crane et al., *J. Biol. Chem.*, 284:35850-35860, 2009.
Crane et al., *Mol. Biol. Cell*, 19:3369-3378, 2008.
De Jager et al., *Semin. Nucl. Med.* 23(2), 165-179, 1993.
Dholakia et al., *J. Biol. Chem.*, 264, 20638-20642, 1989.
Doolittle and Ben-Zeev, *Methods Mol. Biol.*, 109, :215-237, 1999.
Duncan and Winter, *Nature*, 332:738-740, 1988.
EP Application 125,023
EP Application 171,496
EP Application 173,494
EP Application 184,187
Furman et al., *Proc. Natl. Acad. Sci. USA*, 100:13609-13614, 2003.
Gefter et al., *Somatic Cell Genet.*, 3:231-236, 1977.
Goding, In: *Monoclonal Antibodies: Principles and Practice*, 2d ed., Orlando, Fla., Academic Press, 60-61, 65-66, 71-74, 1986.
Gulbis and Galand, *Hum. Pathol.* 24(12), 1271-1285, 1993.
Hagemeyer et al., *Thromb. Haemost.*, 101:1012-1019, 2009.
Harris et al., *J. Mol. Biol.*, 275:861-872, 1998.
Hasegawa et al., *J. Biol. Chem.*, 269:5497-5500, 1994.
Hezareh et al., *J. Virol.*, 75:12161-12168, 2001.
Hinson et al., *Arch Neurol.*, 66:1164-1167, 2009.
Hinson et al., *J. Exp. Med.*, 205:2473-2481, 2008.
Hinson et al., *Neurology*, 69:2221-2231, 2007.
Ho et al., *Proc. Natl. Acad. Sci. USA*, 106:7437-7442, 2009.
Idusogie et al., *J. Immunol.*, 166:2571-2575, 2001.
Igawa et al., *MAbs.*, 3(3), 2011 (Epub ahead of print).
Jujus et al., *Brain*, 131:3072-3080, 2008.
Jones et al., *Nature*, 321:522-525, 1986.
Jung et al., *Proc. Natl. Acad. Sci. USA*, 91:13052-13056, 1994.
Kaneko and Niwa, *BioDrugs*, 25:1-11, 2011.
Khatoon et al., *Ann. of Neurology*, 26, 210-219, 1989.
King et al., *J. Biol. Chem.*, 269, 10210-10218, 1989.
Kinoshita et al., *Biochem. Biophys. Res. Commun.*, 394:205-210, 2010.
Kohler and Milstein, *Eur. J. Immunol.*, 6, 511-519, 1976.
Kohler and Milstein, *Nature*, 256, 495-497, 1975.
Kontermann, *BioDrugs*, 23:93-109, 2009.
Kyte and Doolittle, *J. Mol. Biol.*, 157(1):105-132, 1982.
Landis and Reese, *J. Cell Biol.*, 60:316-320, 1974.
Lennon et al., *J. Exp. Med.*, 202:473-477, 2005.
Li and Verkman, *J. Biol. Chem.*, 276:31233-31237, 2001.
Li et al., *FASEB J.*, 2011 (Epub ahead of print).
Lu et al., *FASEB J.*, 22:3216-3223, 2008.
Lu et al., *Proc. Natl. Acad. Sci. USA*, 93:10908-10912, 1996.
Mader et al., *PLoS One*, 5:e10455, 2010.
Manley et al., *Nat. Med.*, 6:159-163, 2000.
Marignier et al., *Brain*, 133:2578-2591, 2010.
Martinez and Cossart, *J. Cell Sci.*, 117:5097-5106, 2004.
Martinez et al., *Cell*, 123:1013-1023, 2005.
Matiello et al., *Neurology*, 70:2197-2200, 2008.
Morrison, *Science*, 229(4719):1202-1207, 1985.
Nakamura et al., In: *Enzyme Immunoassays: Heterogeneous and Homogeneous Systems*, Chapter 27, 1987.
Neely et al., *Biochemistry*, 38:11156-11163, 1999.
Nicchia et al., *Glia*, 57:1363-1373, 2009.
Nieri et al., *Curr. Med. Chem.*, 16:753-779, 2009.
O'Shannessy et al., *J. Immun. Meth.*, 99, 153-161, 1987.
Owens and Haley, *J. Biol. Chem.*, 259, 14843-14848, 1987.
Padmawar et al., *Nat. Methods*, 2:825-827, 2005.
Papadopoulos et al., *FASEB J.*, 18:1291-1293, 2004.
Patel et al., *Anal. Chem.*, 81:6021-6029, 2009.
PCT Application PCT/US86/02269
PCT Application WO 86/01533
Ponten and Macintyre, *Acta Pathol. Microbiol. Scand.*, 74:465-486, 1968.
Posner et al., *Hybridoma* 6, 611-625, 1987.
Potter and Haley, *Meth. Enzymol.*, 91, 613-633, 1983.
Ratelade et al., *J. Biol. Chem.*, 286(52), 45156-45164, 2011.
Saadoun et al., *Brain*, 131:1087-1098, 2008.
Saadoun et al., *Brain*, 133:349-361, 2010.
Saadoun et al., *J. Cell Sci.*, 118:5691-5698, 2005.
Schagger and Tricine, *Nat. Protoc.* 1:16-22, 2006.
Shaw et al., *J. Natl. Cancer Inst.*, 80(19):1553-1559, 1988.
Sosnick et al., *Biochemistry*, 31:1779-1786, 1992.
Sun et al., *J. Steroid Biochem.*, 26(1):83-92, 1987.
Tajima et al., *J. Biol. Chem.*, 285:8163-8170, 2010.
Tang et al., *J. Biol. Chem.*, 271(26):15682-15686, 1996.
Verhoeyen et al., *Science*, 239(4847):1534-1536, 1988.
Verkman, *Expert Rev. Mol. Med.*, 10:e13, 2008.
Wawrzynczak & Thorpe, *Cancer Treat Res.*, 37:239-51, 1988.
Wingerchuk et al., *Neurology*, 66:1485-1489, 2006.
Wittig et al., *Nat. Protoc.*, 1:418-428, 2006.
Wolburg, *J. Hirnforsch.*, 36:239-258, 1995.
Wood et al., *J. Clin. Lab. Immunol.*, 17(4):167-171, 1985.
Yang et al., *J. Biol. Chem.*, 270:22907-22913, 1995.

What is claimed is:

1. A method of treating a subject with neuromyelitis optica (NMO) spectrum disease comprising administering to said subject a reagent comprising an anti-aquaporin-4 (AQP4) antibody or an antigen binding fragment thereof, wherein said AQP4 antibody or an antigen binding fragment thereof comprises a mutated Fc region of IgG1 antibody which lacks effector functions of an intact antibody, wherein the effector functions are activation of complement and recruitment of immune cells, and wherein said AQP4 antibody or an antigen binding fragment thereof comprises i) a light chain variable region comprising SEQ ID NO: 6, and a heavy chain variable region comprising SEQ ID NO: 8;

ii) a light chain variable region comprising SEQ ID NO: 10, and a heavy chain variable region comprising SEQ ID NO: 12; or iii) a light chain variable region comprising SEQ ID NO: 19, and a heavy chain variable region comprising SEQ ID NO: 17.

2. The method of claim 1, wherein i) said light chain variable region is encoded by the nucleotide sequence comprising SEQ ID NO: 5, and said heavy variable chain region is encoded by the nucleotide sequence comprising SEQ ID NO: 7;

ii) said light chain variable region encoded by the nucleotide sequence comprising SEQ ID NO: 9, and said heavy chain variable region is encoded by the nucleotide sequence comprising SEQ ID NO: 11; or iii) said light chain variable region is encoded by the nucleotide sequence comprising SEQ ID NO: 20, and said heavy chain variable region is encoded by the nucleotide sequence comprising SEQ ID NO: 18.

3. The method of claim 1, wherein said subject is a human subject.

4. The method of claim 1, wherein administering comprises intraocular, intraatertial, subcutaneous, intravenous administration or intrathecal route of administration.

5. The method of claim 1, wherein said mutated Fc region comprises an IgG1 sequence having L234A/L235A substitutions.

6. The method of claim 1, wherein said mutated Fc region comprises an IgG1 sequence having a K322A substitution.

7. The method of claim 1, wherein said mutated Fc region comprises an IgG1 sequence having a G237A amino acid substitution.

8. The method of claim 1, wherein said mutated Fc region comprises an IgG1 sequence having L234A/L235A/G237A substitutions.

9. The method of claim 1, wherein said mutated Fc region comprises a chemically modified Fc region, an antibody Fab fragment and lacks an Fc region, an antibody Fab fragment fused to a non-antibody protein segment, or a single chain antibody or F(ab)$_2$.

10. The method of claim 1, wherein treating comprises reducing one or more of retinal ganglion cell death, optic nerve injury, spinal cord injury, axonal transection, optic nerve demyelination, spinal cord demyelination, astrocyte death or oligodendrocyte death.

11. The method of claim 1, wherein said reagent is administered upon onset of or following an NMO attack.

12. The method of claim 11, wherein said reagent is administered within about 1 hour, 6 hours, 12 hours, 24 hours or two days of an NMO attack.

13. The method of claim 1, further comprising administering to said subject a second agent that treats one or more aspect of NMO.

14. The method of claim 1, further comprising assessing said patient for positive NMO-IgG (AQP4) serology.

15. The method of claim 1, wherein said subject exhibits positive NMO-IgG (AQP4) serology.

16. The method of claim 1, wherein said subject exhibits one or more of transverse myelitis, optic neuritis or other unrelated neurologic dysfunction.

17. The method of claim 16, wherein unrelated neurologic dysfunction comprises protracted nausea or vomiting.

18. A method to reduce exacerbations of neuromyelitis optica (NMO) spectrum disease in a subject comprising administering to said subject a reagent comprising an anti-aquaporin-4 (AQP4) antibody or an antigen binding fragment thereof, wherein said AQP4 antibody or an antigen binding fragment thereof comprises a mutated Fc region of IgG1 antibody which lacks effector functions of an intact antibody, wherein the effector functions are activation of complement and recruitment of immune cells, and wherein said AQP4 antibody or an antigen binding fragment thereof comprises i) a light chain variable region comprising SEQ ID NO: 6, and a heavy chain variable region comprising SEQ ID NO: 8;

ii) a light chain variable region comprising SEQ ID NO: 10, and a heavy chain variable region comprising SEQ ID NO: 12; or iii) a light chain variable region comprising SEQ ID NO: 19, and a heavy chain variable region comprising SEQ ID NO: 17.

19. The method of claim 18, wherein i) said light chain variable region is encoded by the nucleotide sequence comprising SEQ ID NO: 5, and said heavy variable chain region is encoded by the nucleotide sequence comprising SEQ ID NO: 7;

ii) said light chain variable region encoded by the nucleotide sequence comprising SEQ ID NO: 9, and said heavy chain variable region is encoded by the nucleotide sequence comprising SEQ ID NO: 11; or iii) said light chain variable region is encoded by the nucleotide sequence comprising SEQ ID NO: 20, and said heavy chain variable region is encoded by the nucleotide sequence comprising SEQ ID NO: 18.

20. A method of reducing the progression of neuromyelitis optica (NMO) spectrum disease in a subject comprising administering to said subject a reagent comprising an anti-aquaporin-4 (AQP4) antibody or an antigen binding fragment thereof, wherein said AQP4 antibody or an antigen binding fragment thereof comprises a mutated Fc region of IgG1 antibody which lacks effector functions of an intact antibody, wherein the effector functions are activation of complement and recruitment of immune cells, and wherein said AQP4 antibody or an antigen binding fragment thereof comprises i) a light chain variable region comprising SEQ ID NO: 6, and a heavy chain variable region comprising SEQ ID NO: 8;

ii) a light chain variable region comprising SEQ ID NO: 10, and a heavy chain variable region comprising SEQ ID NO: 12; or iii) a light chain variable region comprising SEQ ID NO: 19, and a heavy chain variable region comprising SEQ ID NO: 17.

21. The method of claim 20, wherein i) said light chain variable region is encoded by the nucleotide sequence comprising SEQ ID NO: 5, and said heavy variable chain region is encoded by the nucleotide sequence comprising SEQ ID NO: 7;

ii) said light chain variable region encoded by the nucleotide sequence comprising SEQ ID NO: 9, and said heavy chain variable region is encoded by the nucleotide sequence comprising SEQ ID NO: 11; or iii) said light chain variable region is encoded by the nucleotide sequence comprising SEQ ID NO: 20, and said heavy variable chain region is encoded by the nucleotide sequence comprising SEQ ID NO: 18.

22. A reagent comprising an anti-aquaporin-4 (AQP4) antibody or an antigen binding fragment thereof, wherein said AQP4 antibody or an antigen binding fragment thereof comprises a mutated Fc region of IgG1 antibody which lacks effector functions of an intact antibody, wherein the effector functions are activation of complement and recruitment of immune cells, and wherein said AQP4 antibody or an antigen binding fragment thereof comprises i) a light chain variable region comprising SEQ ID NO: 6, and a heavy chain variable region comprising SEQ ID NO: 8;

ii) a light chain variable region comprising SEQ ID NO: 10, and a heavy chain variable region comprising SEQ ID NO: 12; or iii) a light chain variable region comprising SEQ ID NO: 19, and a heavy chain variable region comprising SEQ ID NO: 17.

23. The reagent of claim 22, wherein
 i) said light chain variable region is encoded by the nucleotide sequence comprising SEQ ID NO: 5, and said heavy variable chain region is encoded by the nucleotide sequence comprising SEQ ID NO: 7;
 ii) said light chain variable region encoded by the nucleotide sequence comprising SEQ ID NO: 9, and said heavy chain variable region is encoded by the nucleotide sequence comprising SEQ ID NO: 11; or
 iii) said light chain variable region is encoded by the nucleotide sequence comprising SEQ ID NO: 20, and said heavy chain variable region is encoded by the nucleotide sequence comprising SEQ ID NO: 18.

24. The reagent of claim 22, wherein said mutated Fc region comprises an IgG1 sequence having one or more substitutions selected from the group consisting of L234A/L235A substitutions, a K322A substitution, and a G237A amino acid substitution.

\* \* \* \* \*

UNITED STATES PATENT AND TRADEMARK OFFICE
CERTIFICATE OF CORRECTION

| | |
|---|---|
| PATENT NO. | : 10,654,916 B2 |
| APPLICATION NO. | : 14/113061 |
| DATED | : May 19, 2020 |
| INVENTOR(S) | : Jeffrey L. Bennett et al. |

It is certified that error appears in the above-identified patent and that said Letters Patent is hereby corrected as shown below:

In the Specification

Column 1, Lines 10-13, delete "This invention was made with government support under grant numbers EY13574, EB00415, DK35124, HL73856, DK86125 and DK72517 awarded by the National Institutes of Health (NIH)." and insert therefor -- This invention was made with government support under grant numbers EY13574, EB00415, DK35124, HL73856 and DK86125 awarded by the National Institutes of Health (NIH). --

Signed and Sealed this
Fifth Day of November, 2024

Katherine Kelly Vidal
*Director of the United States Patent and Trademark Office*

SEQUENCE LISTING

<160> NUMBER OF SEQ ID NOS: 20

<210> SEQ ID NO 1
<211> LENGTH: 1023
<212> TYPE: DNA
<213> ORGANISM: Homo sapiens

<400> SEQUENCE: 1

```
gcctccacca agggcccatc ggtcttcccc ctggcgccct gctccaggag cacctccgag      60
agcacagcgg ccctgggctg cctggtcaag gactacttcc ccgaaccggt gacggtgtcg     120
tggaactcag gcgccctgac cagcggcgtg cacaccttcc cggctgtcct acagtcctca     180
```

```
ggactctact ccctcagcag cgtggtgacc gtgccctcca gcagcttggg cacccagacc    240
tacatctgca acgtgaatca caagcccagc aacaccaagg tggacaagaa agttgagccc    300
aaatcttgtg acaaaactca cacatgccca ccgtgcccag cacctgaagc cgcggggga    360 ccgtcagtct tcctcttccc cccaaaaccc aaggacaccc tcatgatctc ccggacccct    420
gaggtcacat gcgtggtggt ggacgtgagc cacgaagacc ctgaggtcaa gttcaactgg    480
tacgtggacg gcgtggaggt gcataatgcc aagacaaagc cgcgggagga gcagtacaac    540
agcacgtacc gtgtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag ggcagccccg agaaccacag gtgtacaccc tgcccccatc ccgggatgag    720
ctgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctac agcaagctca ccgtggacaa gagcaggtgg    900
cagcagggga acgtcttctc atgctccgtg atgcatgagg ctctgcacaa ccactacacg    960
cagaagagcc tctccctgtc tccgggtaaa ctcgaggact acaaggacga tgacgataag   1020
tga                                                                 1023

<210> SEQ ID NO 2
<211> LENGTH: 340
<212> TYPE: PRT
<213> ORGANISM: Homo sapiens

<400> SEQUENCE: 2

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220
```

```
Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys Leu Glu Asp Tyr Lys Asp
                325                 330                 335

Asp Asp Asp Lys
            340

<210> SEQ ID NO 3
<211> LENGTH: 1023
<212> TYPE: DNA
<213> ORGANISM: Homo sapiens

<400> SEQUENCE: 3
gcctccacca agggcccatc ggtcttcccc ctggcgccct gctccaggag cacctccgag      60
agcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaact cctgggggga     360
ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacaac     540
agcacgtacc gtgtggtcag cgtcctcacc gtcctgcacc aggactggct gaatggcaag     600
gagtacaagt gcgcggtctc caacaaagcc ctcccagccc ccatcgagaa aaccatctcc     660
aaagccaaag gcagccccg agaaccacag gtgtacaccc tgcccccatc ccgggatgag     720
ctgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctac agcaagctca ccgtggacaa gagcaggtgg     900
cagcagggga acgtcttctc atgctccgtg atgcatgagg ctctgcacaa ccactacacg     960
cagaagagcc tctccctgtc tccgggtaaa ctcgaggact acaaggacga tgacgataag    1020
tga                                                                 1023

<210> SEQ ID NO 4
<211> LENGTH: 340
<212> TYPE: PRT
<213> ORGANISM: Homo sapiens

<400> SEQUENCE: 4

Ala Ser Thr Lys Gly Pro Ser Val Phe Pro Leu Ala Pro Cys Ser Arg
1               5                   10                  15
```

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Ala Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys Leu Glu Asp Tyr Lys Asp
                325                 330                 335

Asp Asp Asp Lys
            340

<210> SEQ ID NO 5
<211> LENGTH: 645
<212> TYPE: DNA
<213> ORGANISM: Homo sapiens

<400> SEQUENCE: 5
gaaattgtgt tgacacagtc tccaggcacc ctgtctttgt ctccagggga aagagccacc        60
ctctcctgca gggccagtca gactgttcgc accaactact tagcctggtt ccagcagaaa       120
cctggccagg ctcccaggct cctcatcttt ggtgcatcca gcagggccac tggcatccca       180
gacaggttca gtggcagtgg gtctgggaca gacttcactc tcaccatcag cagactggag       240

```
cctgaagatt ttgcagtgta ttactgtcag cagtatggta gctcaccgtg gacgttcggc    300
caagggacca aggtggaaat caaacgaact gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag acagcacct acagcctcag cagcaccctg    540
acgctgagca agcagacta cgagaaacac aaagtctacg cctgcgaagt cacccatcag    600
ggcctgagtt cgcccgtcac aaagagcttc aacaggggag agtgt                   645
```

```
<210> SEQ ID NO 6
<211> LENGTH: 215
<212> TYPE: PRT
<213> ORGANISM: Homo sapiens

<400> SEQUENCE: 6

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Thr Val Arg Thr Asn
            20                  25                  30

Tyr Leu Ala Trp Phe Gln Gln Lys Pro Gly Gln Ala Pro Arg Leu Leu
        35                  40                  45

Ile Phe Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 7
<211> LENGTH: 372
<212> TYPE: DNA
<213> ORGANISM: Homo sapiens

<400> SEQUENCE: 7
caggtgcagc tgcaggagtc gggcgcagga ctggtgaagc cttcggagac cctgtccctc    60
acctgcactg tctctggtgg ctccatcagt ggtcactact ggaactggat ccggcagccc    120
ccagggaagg gactggagtg gattgggtac atccattaca gtgggagcac caactacaac    180
```

```
ccctccctca agagtcgagt caccatatca gtggacacgt ccaagaacca gttctccctg    240
aagctgagct ctgtgaccgc tgcggacacg gccgtgtatt actgtgcgag agcagagggg    300
agaggatgga gtgctttcta ctactactac atggaagtct ggggcaaagg gtccacggtc    360
tccgtctcct ca                                                       372
```

<210> SEQ ID NO 8
<211> LENGTH: 124
<212> TYPE: PRT
<213> ORGANISM: Homo sapiens

<400> SEQUENCE: 8

```
Gln Val Gln Leu Gln Glu Ser Gly Ala Gly Leu Val Lys Pro Ser Glu
 1               5                  10                  15

Thr Leu Ser Leu Thr Cys Thr Val Ser Gly Gly Ser Ile Ser Gly His
            20                  25                  30

Tyr Trp Asn Trp Ile Arg Gln Pro Pro Gly Lys Gly Leu Glu Trp Ile
        35                  40                  45

Gly Tyr Ile His Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Glu Gly Arg Gly Trp Ser Ala Phe Tyr Tyr Tyr Met Glu
            100                 105                 110

Val Trp Gly Lys Gly Ser Thr Val Ser Val Ser Ser
        115                 120
```

<210> SEQ ID NO 9
<211> LENGTH: 642
<212> TYPE: DNA
<213> ORGANISM: Homo sapiens

<400> SEQUENCE: 9

```
gacatccaga tgacccagtc tccatccgcc ctgtctgcat ctgtaggaga cacagtcacc     60
atcacttgcc gggccagtca gagtattagg agctggttgg cctggtatca gcagaaacca    120
gggaaagccc ctaaactcct gatctataag gcgtctgatt tacaaagtgg ggtcccatca    180
agattcagcg gcagtggatc tgggacagac ttcactctca ccatcagcgg cctgcagcct    240
gatgattttg caacttatta ctgccaacac tataatagtt acccgtacac ttttggccag    300
gggaccaagg tggagatcag acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagttcgc ccgtcacaaa gagcttcaac aggggagagt gt                      642
```

<210> SEQ ID NO 10
<211> LENGTH: 214
<212> TYPE: PRT
<213> ORGANISM: Homo sapiens

<400> SEQUENCE: 10

Asp Ile Gln Met Thr Gln Ser Pro Ser Ala Leu Ser Ala Ser Val Gly

Asp Thr Val Thr Ile Thr Cys Arg Ala Ser Gln Ser Ile Arg Ser Trp
1               5                   10                  15

Leu Ala Trp Tyr Gln Gln Lys Pro Gly Lys Ala Pro Lys Leu Leu Ile
            20                  25                  30

Tyr Lys Ala Ser Asp Leu Gln Ser Gly Val Pro Ser Arg Phe Ser Gly
        35                  40                  45

Ser Gly Ser Gly Thr Asp Phe Thr Leu Thr Ile Ser Gly Leu Gln Pro
50                  55                  60

Asp Asp Phe Ala Thr Tyr Tyr Cys Gln His Tyr Asn Ser Tyr Pro Tyr
65                  70                  75                  80

Thr Phe Gly Gln Gly Thr Lys Val Glu Ile Arg Arg Thr Val Ala Ala
            85                  90                  95

Pro Ser Val Phe Ile Phe Pro Pro Ser Asp Glu Gln Leu Lys Ser Gly
        100                 105                 110

Thr Ala Ser Val Val Cys Leu Leu Asn Asn Phe Tyr Pro Arg Glu Ala
    115                 120                 125

Lys Val Gln Trp Lys Val Asp Asn Ala Leu Gln Ser Gly Asn Ser Gln
130                 135                 140

Glu Ser Val Thr Glu Gln Asp Ser Lys Asp Ser Thr Tyr Ser Leu Ser
145                 150                 155                 160

Ser Thr Leu Thr Leu Ser Lys Ala Asp Tyr Glu Lys His Lys Val Tyr
            165                 170                 175

Ala Cys Glu Val Thr His Gln Gly Leu Ser Ser Pro Val Thr Lys Ser
        180                 185                 190

Phe Asn Arg Gly Glu Cys
    195                 200                 205

210

<210> SEQ ID NO 11
<211> LENGTH: 345
<212> TYPE: DNA
<213> ORGANISM: Homo sapiens

<400> SEQUENCE: 11
gtgcagctgg tggagtctgg gggtggcttg gttcagccgg ggggtccct gagactctcc      60 tgtgcagcct ctggattcac ctttagaggt tatgccatga actgggtccg ccaggcccca    120
gggaaggggc tggagtgggt cgcaagtatc agtggcagtg gtagtatcac acagtacgca    180
gactccgcga agggccgctt caccatcacc agagacaact ccaagagcac gctctatgcg    240
catgtgagta gcctgagagc cgatgacacg gccgtatatt actgtgcgaa aggggactac    300
gtctttgact actggggaca gggaaccctg gtcaccgtct cctca                    345

<210> SEQ ID NO 12
<211> LENGTH: 115
<212> TYPE: PRT
<213> ORGANISM: Homo sapiens

<400> SEQUENCE: 12

Val Gln Leu Val Glu Ser Gly Gly Gly Leu Val Gln Pro Gly Gly Ser
1               5                   10                  15

Leu Arg Leu Ser Cys Ala Ala Ser Gly Phe Thr Phe Arg Gly Tyr Ala
            20                  25                  30

Met Asn Trp Val Arg Gln Ala Pro Gly Lys Gly Leu Glu Trp Val Ala
        35                  40                  45

Ser Ile Ser Gly Ser Gly Ser Ile Thr Gln Tyr Ala Asp Ser Ala Lys

```
                  50                  55                  60
Gly Arg Phe Thr Ile Thr Arg Asp Asn Ser Lys Ser Thr Leu Tyr Ala
 65                  70                  75                  80

His Val Ser Ser Leu Arg Ala Asp Asp Thr Ala Val Tyr Tyr Cys Ala
                 85                  90                  95

Lys Gly Asp Tyr Val Phe Asp Tyr Trp Gly Gln Gly Thr Leu Val Thr
                100                 105                 110

Val Ser Ser
       115

<210> SEQ ID NO 13
<211> LENGTH: 10
<212> TYPE: PRT
<213> ORGANISM: Artificial Sequence
<220> FEATURE:
<223> OTHER INFORMATION: Synthetic peptide

<400> SEQUENCE: 13

Glu Gln Lys Leu Ile Ser Glu Glu Asp Leu
1               5                   10

<210> SEQ ID NO 14
<211> LENGTH: 1023
<212> TYPE: DNA
<213> ORGANISM: Homo sapiens

<400> SEQUENCE: 14
gcctccacca agggcccatc ggtcttcccc ctggcgccct gctccaggag cacctccgag      60
agcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaagc cgcgggggca     360
ccgtcagtct tcctcttccc cccaaaaccc aaggacaccc tcatgatctc ccggaccccc     420
gaggtcacat gcgtggtggt ggacgtgagc cacgaagacc ctgaggtcaa gttcaactgg     480
tacgtggacg gcgtggaggt gcataatgcc aagacaaagc cgcggaggga gcagtacaac     540
agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag gcagccccg agaaccacag gtgtacaccc tgcccccatc ccgggatgag     720
ctgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctac agcaagctca ccgtggacaa gagcaggtgg     900
cagcagggga acgtcttctc atgctccgtg atgcatgagg ctctgcacaa ccactacacg     960
cagaagagcc tctccctgtc tccgggtaaa ctcgaggact acaaggacga tgacgataag    1020
tga                                                                 1023

<210> SEQ ID NO 15
<211> LENGTH: 340
<212> TYPE: PRT
<213> ORGANISM: Homo sapiens

<400> SEQUENCE: 15
```

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys Leu Glu Asp Tyr Lys Asp
                325                 330                 335

Asp Asp Asp Lys
            340

<210> SEQ ID NO 16
<211> LENGTH: 10
<212> TYPE: PRT
<213> ORGANISM: Artificial
<220> FEATURE:
<223> OTHER INFORMATION: Synthetic oligonucleotide

<400> SEQUENCE: 16

Leu Glu Asp Tyr Lys Asp Asp Asp Asp Lys
1               5                   10
```

<210> SEQ ID NO 17
<211> LENGTH: 140
<212> TYPE: PRT
<213> ORGANISM: Homo sapiens

<400> SEQUENCE: 17

Val Thr Thr Gly Val His Ser Glu Val Gln Leu Val Glu Ser Gly Gly
1               5                   10                  15

Gly Val Val Gln Pro Gly Gly Ser Leu Arg Leu Ser Cys Thr Ala Ser
            20                  25                  30

Gly Phe Asn Leu Asp Asp Tyr Asp Ile His Trp Val Arg Gln Ala Pro
        35                  40                  45

Gly Lys Gly Leu Gln Trp Val Ala Ile Leu Gln Pro Glu Glu Ser His
    50                  55                  60

Gln Asp Tyr Ile Asn Ser Val Arg Gly Arg Phe Ser Val Ser Arg Asp
65                  70                  75                  80

Ser Ser Arg Asp Thr Ile Asp Leu Gln Met His Ser Leu Arg Pro Glu
                85                  90                  95

Asp Thr Ala Ile Tyr Tyr Cys Thr Arg Ser Pro Gly Leu Met Thr Thr
            100                 105                 110

Leu Arg Gly Met Val Thr Arg Arg His Phe His Tyr Phe Thr Met Asp
        115                 120                 125

Val Trp Gly Lys Gly Thr Thr Val Ile Val Ser Ser
    130                 135                 140

<210> SEQ ID NO 18
<211> LENGTH: 420
<212> TYPE: DNA
<213> ORGANISM: Homo sapiens

<400> SEQUENCE: 18
gtaactacag gtgtccactc cgaggtgcag ctggtggagt ctgggggagg cgtggtccag      60
cctggggggt ccctaagact ctcctgtaca gcgtctggtt tcaacttaga tgactatgac     120
attcactggg tccgccaggc gcccggcaag gggctgcagt gggtggcaat tttgcagcct     180
gaagaaagtc atcaagacta tataaattcc gtgaggggcc gattctccgt ctccagagac     240
agttcgaggg acacaataga tctgcaaatg cacagtctta gacctgaaga cacggctata     300
tattactgta cgcgatctcc gggcctcatg actacgctgc ggggaatggt gaccaggagg     360
cactttcact acttcaccat ggacgtctgg ggcaaaggga ccacggtcat cgtctcctca     420

<210> SEQ ID NO 19
<211> LENGTH: 234
<212> TYPE: PRT
<213> ORGANISM: Homo sapiens

<400> SEQUENCE: 19

Val Leu Gly Leu Leu Leu Leu Trp Leu Thr Asp Ala Arg Cys Asp Ile
1               5                   10                  15

Val Met Thr Gln Ser Pro Leu Ser Leu Pro Val Thr Pro Gly Glu Pro
            20                  25                  30

Ala Ser Ile Ser Cys Arg Ser Gln Ser Leu Arg His Thr Ile Thr
            35                  40                  45

Gly Tyr Asn Tyr Ile Asn Trp Tyr Leu Gln Lys Pro Gly Gln Ser Pro
    50                  55                  60

Gln Leu Leu Ile Phe Leu Ala Ser Ser Arg Ala Thr Gly Val Pro Asp
65                  70                  75                  80

```
Arg Phe Ser Gly Ser Gly Ala Gly Thr Asp Phe Thr Leu Lys Ile Ser
                85                  90                  95

Arg Val Glu Ala Glu Asp Val Gly Ile Tyr Tyr Cys Met Gln Ala Leu
            100                 105                 110

His Thr Pro Pro Thr Phe Gly Gln Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Leu Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 20
<211> LENGTH: 705
<212> TYPE: DNA
<213> ORGANISM: Homo sapiens

<400> SEQUENCE: 20
gtcctggggt tgctgctgct gtggcttaca gatgccagat gtgatattgt gatgactcag      60
tctccactct ccctgcccgt cacccctgga gagccggcct ctatctcctg caggtctagt     120
cagagcctcc gccacaccat cactggatac aactatatca attggtacct gcagaagcca     180
gggcagtctc cacaactcct gatcttttg gcctcttctc gggccaccgg ggtccctgac      240
aggttcagtg gcagtggagc aggcacagat tttacactga aaatcagcag agtggaggct     300
gaggatgttg gaatttatta ctgcatgcaa gctctacaca ctccgccac ttttggccag      360 gggaccaaac tggagatcaa acgaactgtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgccc tccaatcggg taactcccag     540
gagagtgtca cagagcagga cagcaaggac agcacctaca gcctcagcag caccctgacg     600
ctgagcaaag cagactacga gaaacacaaa gtctacgcct gcgaagtcac ccatcagggc     660
ctgagttcgc ccgtcacaaa gagcttcaac aggggagagt gttaa                    705
```